(12) United States Patent
Atkinson et al.

(10) Patent No.: US 6,897,290 B1
(45) Date of Patent: May 24, 2005

(54) MODIFIED RCA PROTEINS

(75) Inventors: John P. Atkinson, St. Louis, MO (US);
Dennis Hourcade, Creve Coeur, MO (US); Malgorzata Krych, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/126,505

(22) Filed: Sep. 24, 1993

Related U.S. Application Data

(63) Continuation-in-part of application No. 07/695,514, filed on May 3, 1991, now abandoned.

(51) Int. Cl.[7] ............................................. C07K 19/00

(52) U.S. Cl. .................... 530/350; 435/69.1; 435/69.6; 536/23.4; 536/23.5

(58) Field of Search ........................ 530/350; 435/69.1, 435/69.6; 536/23.4, 23.5

(56) References Cited

U.S. PATENT DOCUMENTS

| | | | | |
|---|---|---|---|---|
| 4,883,784 A | * | 11/1989 | Kaneko ........................... | 514/8 |
| 4,935,233 A | * | 6/1990 | Bell et al. .................. | 424/85.5 |
| 5,212,071 A | | 5/1993 | Fearon et al. .............. | 435/69.1 |
| 5,256,642 A | * | 10/1993 | Fearon et al. .................. | 514/8 |
| 5,545,619 A | * | 8/1996 | Atkinson et al. ............. | 514/12 |

FOREIGN PATENT DOCUMENTS

| | | | |
|---|---|---|---|
| JP | PCT/JP93/00207 | | 9/1993 |
| WO | WO 89/01041 | * | 2/1989 |
| WO | WO 89/09220 | | 10/1989 |
| WO | WO 91/05047 | | 4/1991 |

OTHER PUBLICATIONS

Lowell et al. J. Exp. Med. 170, 1931–1946, 1989.*
Dykman, et al., "Structural Heterogeneity of the C3b/C4b Receptor (CR1) on Human Peripheral Blood Cells," *J. Exp. Med.* 157:2160–2165 (1983).
Farries, et al., "Competition for Binding Sites on C3b by CR1, CR2, MCP, Factor B and Factor H," *Complement Inflamm* 7:30–41 (1990).
Fodor, et al., "A Novel Bifunctional Chimeric Complement Inhibitor That Regulates C3 Convertase and Formation of the Membrane Attack Complex," *J. of Immunol,* 4135–4138 (1995).
Ghebrehiwet, B., et al., "Purification and Immunochemical of Soluble Forms of the Two Types of C10 Receptors," *Complement and Complement Receptors* Abstract 2751 (1994).

Gouiet–Zalc, et al., "Marmoset Red Blood Cell Receptor for Membrane–Associated Complement Components Is Not Related to Human CR1: Partial Characterization of the C3–Binding Proteins Responsible for the Spontaneous Rosette Formation between Marmoset Red Blood Cells and Human Leukocytes," *Cell Immun.* 109:282–294 (1987).
Hillaro, A., and Dahlback, B., "Cloning of cDNA coding for the β chain of the human complement component C4b–binding protein: Sequene homology with the α chain," *Proc. Natl. Acad. Sci. USA* 87:1183 (1990).
Himmelfarb, et al., "Soluble complement receptor 1 inhibits both complement and granulocyte activation during ex vivo hemodialysis," *J. Lab. Clin. Med.* 126:392–400 (1995).
Hogg, N., et al., "Identification of an anti–moniclonal antibody that is specific for membrane complement receptor type one ($CR_1$)," *Eur. J. Immunol.* 14:236–243 (1984).
Holers, et al., "Human C3b– and C4b–regulator proteins: a new multi–gene family," *Immun. Today* 6:188 (1985).
Hourcade, et al., "Duplication and Divergence of the Aminterminal Coding Region of the Complement Receptor 1 (CR1) Gene," *J. of Biol. Chem.* 265:974–980 (1990).
Hourcade, D., et al., "Analysis of the Human Regulators of Complement Activation (RCA) Gene Cluster with Yeast Artificial Chromosomes (YACs)," *Genomics* 12:289–300 (1992).
Hourcade and Atkinson, "The Regulators of Complement Activation (RCA) Gene Cluster," *Progress in Immun,* VII:171 (1989).
Janatova, et al., "Disulfide Bonds Are Localized within the Short Consensus Repeat Units of Complement Regulatory Proteins: C4b–Binding Protein," *Biochem.* 28:4754–4761 (1989).
Joyner et al., "Production of a mutation in mouse En–2 gene by homologous recombination in embryonic stem cells." *Nature* 338:153–156 (1989).
Kalli, et al., "Interaction of iC3b with Recombinant Isotypic and Chimeric Forms of CR2." *J. Immunology* 147:590–594 (1991).
Kalli, et al., "Mapping of the C3b–binding Site of CR1 and Construction of a $(CR1)_2$–$F(ab)_2$ Chimeric Complement Inhibitor," *J. Exp. Med.* 174:1451–1460 (1991).
Kim, "Isolation and Identification of Trophoblast Lymohoctye Cross–reactive (TLX) Antigens from Human Lymphocytes." *J. of Biol. Chem.* 264:9780–9784 (1989).

(Continued)

*Primary Examiner*—Gary Kunz
(74) *Attorney, Agent, or Firm*—Hamilton, Brook, Smith & Reynolds, P.C.

(57) ABSTRACT

Analogs of regulators of complement activation (RCA) proteins which have altered specificities and affinities for the targets C3b and/or C4b are described. These analogs are obtained by substituting amino acids which affect the complement inhibitory activities of these proteins, substituting, rearranging or adding SCRs (short consensus repeats) or SCR regions to the proteins, deleting amino acid sequences, and combinations thereof.

26 Claims, 3 Drawing Sheets

OTHER PUBLICATIONS

Figure 1:
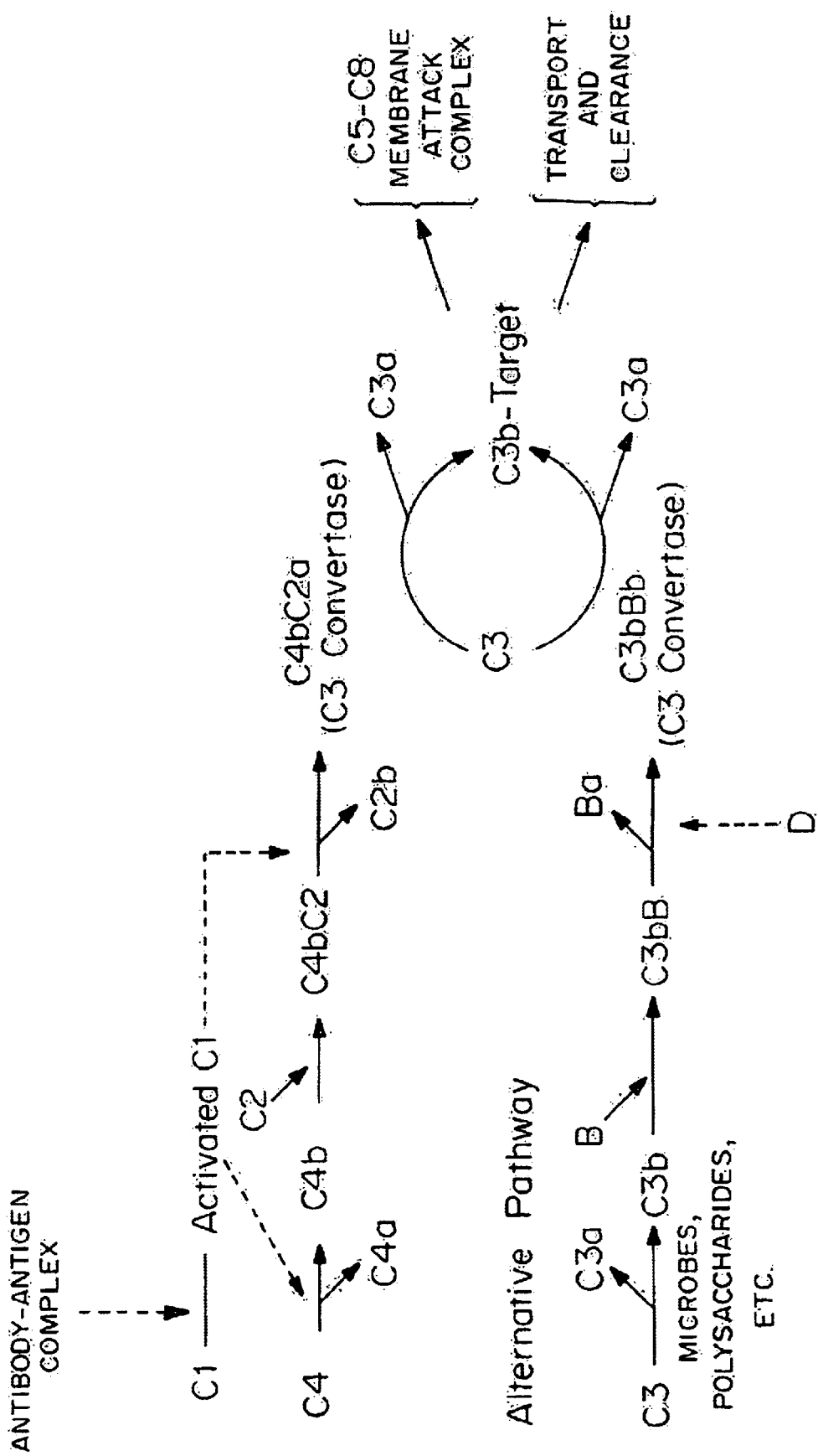

Klickstein, L.B., et al., "Human C3b/C4b Receptor (CR1)," *J. Exp. Med.* 165:1095 (1987).

Krych, et al., "Sites within the complement C3b/C4b receptor important for the specificity of ligand binding." *Proc. Natl. Acad. Sci. USA* 88:4353–4357 (1991).

Krych, et al., "Identification of a C3b Binding Domain of Human Complemet C3B/C4b Receptor (CR1)," *FASEB J.* 4(7) (1990).

Kunkel, T.A., et al., "Rapid and Efficient Site–Specific Mutagenesis without Phenotypic Selection," *Methods Enzymol* 154:367–382 (1987).

Liszewski, M. Kathryn, et al., "Control of the Complement System," *Adv. in Immunol.* 1996 61:201–203. Review.

Lovell–Badge, "Introduction of DNA into embryonic stem cells," *Teratocarcinomas and embryonic stem cells, a practical approach*, 153 (ed. E.J. Robertson, IRL Press, 1987).

Lublin, et al., "The Gene Encoding Decay–Accelerating Factor (DAF) is Located in the Complement–Regulatory Locus on the Long Arm of Chrosome," *J. Exp. Med.* 165:1731–1736 (1987).

Lublin, D.M., et al., "Molecular Cloning and Chrosomal Localization of Human Membrane Cofactor Protein (MCP)," *J. Exp. Med.* 168:181 (1988).

Lublin and Atkinson, "Decay Accelerating Factor: Biochemistry Molecular Biology, and Function," *Ann. Rev. Immunol.* 7:35–38 (1989).

Lublin and Atkinson, "Decay–Accelerating Factor and Membrane Cofactor Protein," *Curr. Topics in Micro. and Immun.* 153:123 (1989).

Makrides, S.C. et al., "Cell Surfaces Expression of the C3b/C4b Receptor (CR1) Protects Chinese Hamster Ovary Cells from Lysis by Human Complement," *J. Biol. Chem.* 267:24754–24761 (1992).

McNearncy, et al., "Membrane Cofactor Protein of Complement is Present on Human Fibroblast, Epithelial, and Endothelial Cells," *J. Clin. Invest.* 84(1989).

Medof, M.E., et al., "Cloning and characterization of cDNAs encoding the complete sequence of decay–accelerating factor of human complement," *Proc. Natl. Acad. Sci. USA* (1987) 84:2007.

Moore, "CRRP: A Guinea Pig Protein, Identified by Sequence Homology to Human CR1, Which Contains Two Short Consenus Repeat Motifs and Appears not to be Transmembrane or Secreted," *J. of Immunol.* 147:3615–3622 (1991).

Moore, M.D., et al., "Molecular cloning of the cDNA encoding the Epstein–Barr virus/C3d Receptor (complement receptor type 2), of human B lymphocytes," *Proc. Natl. Acad. Sci. USA* 84:9194 (1987).

Nickells, et al., "Identification of Complement Receptor Type 1–Related Proteins on Primate Erythrocytes," *J. of Immuol.* 2829 (1995).

Nickells, et al., "Identification of 65–70kDa CR1 Molecules from Primate E," *Complement and Complement Receptors FASEB Journal* Abstract 2749, (1994).

O'Shea, J.J., et al., "Evidence for Distinct Intracellular Pools of Receptors for C3b and C3bi In Human Neutrophils," *J. Immunol.* 134:2580–2587 (1985).

Ogata, et al., "Murine C4b–Binding Protein," *J. Immunology* 150:2273–2280 (1993).

Post, et al., "Membrane Cofactor Protein of the Complement System: Alternative Splicing of Serine/Threonin/Proline–rich Exons and Cytoplasmic Tails Produces Multiple Isoforms that Correlate with Protein Phenotype," *J. Exp. Med.* 174:93–102 (1991).

Potter et al., "Enhancer–dependent expression of human K immunoglobulin genes introducted into mouse pre–B lymphocytes by electroporation," *Proc. Natl. Acad. Sci. USA* 81:161 (1984).

Pruitt, et al., "The Effect of Soluble Complement Receptor Type 1 on Hyperacute Xenograft Rejection," *Transplantation* 52:868–873 (1991).

Purcell, et al., "The human cell–surface glycoproteins HuLy–m5, membrane co–factor protein (MCP) of the complement system and trophoblast leucocyte–common (TLX) antigen, are CD46," *Immun.* 70:155–161 (1990).

*Remington: The Science and Practive of Pharmacy* Nineteenth Edition, vol. I and II, (1995) pp VIII, XI, XVI.

Ripoche, J., et al., "The complete amino acid sequence of human complement factor H." *Biochem. J.* 249:593 (1988).

Seya, T., et al., "Purification and Functional Analysis of the Polymorphic Variants of the C3b/C4b Receptor (CR1) and Comparison with H, C4b–Binding Protein (C4bpl, and Decay Acceleration Factor (DAF)," *J. Immunology* 135:2661 (1985).

Seya and Atkinson, "Functional properties of membrane cofactor protein of complement," *Biochem. J.* 264:581 (1989).

Seya, et al., "Membrane Cofactor Protein (MCP or gp 45–70): A Distinct Complement Regulatory Protein with a Wide Tissue Distribution," XII th Internl. Complement Workshop, Chamonix, France, Sep. 18–21, 1987 Complement (1987) 4:3–4, 225.

Seya, et al., "Distribution of membrane cofactor protein of complement on human peripheral blood cells, An altered form is found on granulcytes," *Eur. J. Immunol.* 18:1289–1294 (1988).

Seya, et al., "Purification and Characterization of a Membrane Protein (gp45–70) that is a Cofactor for Cleavage of C3b and C4b," *J. Exp. Med.* 163:837 (1986).

Seya, "membrane cofactor protein (MCP)," Complement Regulation (1988).

Southern and Bero, "Transformation of Mammalian Cells to Antibiotic Resistance with a Bacterial Gene Under Control of the SV40 Early Region Promoter," *J. Mol. Appl. Gen.* 1:327–341 (1982).

Stafford, et al., "Normal polymorphic variations and transcription of the decay accelerating factor gene in paroxysmal nocturnal hemoglobinuria cells," *Proc. Natl. Acad. Sci. USA* 85:880–884 (1988).

Subramanian, Y., et al., "Ligand Binding by Chimpanzee Erythrocyte Comolement Receptor," *Complement and Completement Receptors, FASEB Journal* Abstract 4447 (1994).

Weiss, J.J., "Structure of the Human B Lymphocyte Receptor for C3d and the Epstein–Barr Virus and Relatedness to Other Members of the Family of C3/C4 Binding Proteins," *J. Exp. Med.* 167:1047 (1988).

Wong and Fearon, "p65: A C3b–Binding Protein on Murine Cells that Shares Antigenic Determinants with the Human C3b Receptor (CR1) and is Distinct from Murine C3b Receptor," *J. Immun.* 134:4048 (1985).

Wong, "Structural and Functional Correlation of the Human Complement Receptor Type 1," *J. of Investigative Dermatology* 94:64S–67S (1990).

Wong, et al., "Identification of a partial cDNA clone for the human receptor for complement fragments C3b/C4b," *Proc. Natl. Acad. Sci. USA* 82:7711–7715 (1985).

Wong and Farrell, "Proposed Structure of tghe F' Allotype of Human CR1," *J. of Immunol*, 146:656–662 (1991).

Yu, et al., "Identification of a Third Component of Complement–binding Glycoprotein of Human Platelets," *J. Clin. Invest.* 78:494–501 (1986).

Zimmer and Gruss, "Production of chimaeric mice containing embryonic stem (ES) cells carrying a homoeobox Hox 1.1 allele mutated by homologous recombination," *Nature* 338:150–153 (1989).

Hourcade et al., *Adv. Immunol.* (1989) 45:381–416.

Klickstein et al., *J. Exp. Med.* (1988) 168:1699–1717.

Hourcade et al., *J. Exp. Med.* (1988) 168:1699–1717.

Ross et al., *Adv. Immunol.* (1985) 37:217–267.

Platt et al., *Immunol. Today* (1990) 11:450–457.

Yeh et al., *J. Immunol.* (1991) 146:250–256.

Weissman et al., *Science* (1990) 249:146–151.

Kotwal et al., *Nature* (1988) 335:176–178.

McNearney, *J. Exp. Med.* (1987) 166:1525–1535.

Bellard, et al., A Polymorphism of the Complement Regulatory Protein MCP (Membrane Cofactor Protein of gp45–70) *J. of Immun.* 138:3850–3855 (1987).

Ballard, et al., "Biochemical Characterization of Membrane Cofactor Protein of the Complement System," *J. of Immun.* 141:3923–3929 (1988).

Birmingham and Cosio, "Characterization of the Baboon Erthrocyte C3b–Binding Protein," *J. of Immun.* 142:3140–3144 (1989).

Birmingham, et al., "Primary Sequence of an Alternatively Spliced Form of CR1," *J. of Immunol.* 691 (1994).

Bora, et al., "Structural Gene for Human Membrane Cofactor Protein (MCP) of Complement Maps to Within 100 kb of the 3' End of the C3b/C4b Receptor Gene," *J. Exp. Med.* 169:597–602 (1989).

Brauer, et al., "Use of C6–Deficient Rats to Evaluate the Mechanism of Hyperacute Rejection of Discordant Cardia Xenografts," *J. of Immunol.* 151:7240–7248 (1993).

Caras, et al., "Signal for Attachment of a Phospholipid Membrane Anchor in Decay Accelerating Factor," *Science* 238:1280 (1987).

Caras, I.W., et al., "Cloning of decay–accelerating factor suggests noval use of splicing to generate two proteins," *Nature* (1987) 325:545.

Carel, et al., "Structural Requirements for C3d.g/Epstein–Barr Virus Receptor (CR21/CD21) Ligand Binding, Internalization and Viral Infection," *J. Biol. Chem.* 265:12293–12299 (1990).

Chung, L.P. et al., "Molecular cloning and characterization of the cDNA coding for C4b–binding protein, a regulatory protein of the classical pathway of the human complement system," *Biochem. J.* 230:133 (1985).

Clemenza, et al., "Generation of a Functional Domain of CR1 with Increased Ligand Binding and Cofactor Activities," Mol. Immunol. 1993 vol. 30, No. Suppl. 1, pp. 4.

Cole, J. L., et al., "Indentification of an additional class of C3–binding membrane proteins of human peripheral blood leukocytes and cell lines," *Proc. Natl. Acad. Sci. USA* 82:859–863 (1985).

Coyne, et al., "Mapping of Epitopes, Glycosylation Sites, and Complement Regulatory Domains in Human Decay Accelerating Factor," *J. Immunology* 149:2906–2913 (1992).

Dykman et al., "Polymorphism of human erythrocyte C3b/C4b receptor," *Proc. Natl. Acad. Sci. USA* 80:1698–1702 (1983).

Adams, et al., "Contribution of the Repeating Domains of Membrane Cofactor Protein (CD46) of the Complement System to Ligand Binding and Cofactor Activity," *J. Immunology* 147:3005–3011 (1991).*

Alsenz, et al., "Localization of the complement–component–C3b–binding site and the cofactor activity for factor I in the 38kDa tryptic fragment of factor H,"*Biochem. J.* 389 (1984).*

Atkinson and Farries, "Separation of self from non–self in the complement system.", Immun. Today 8:212 (1987).*

* cited by examiner

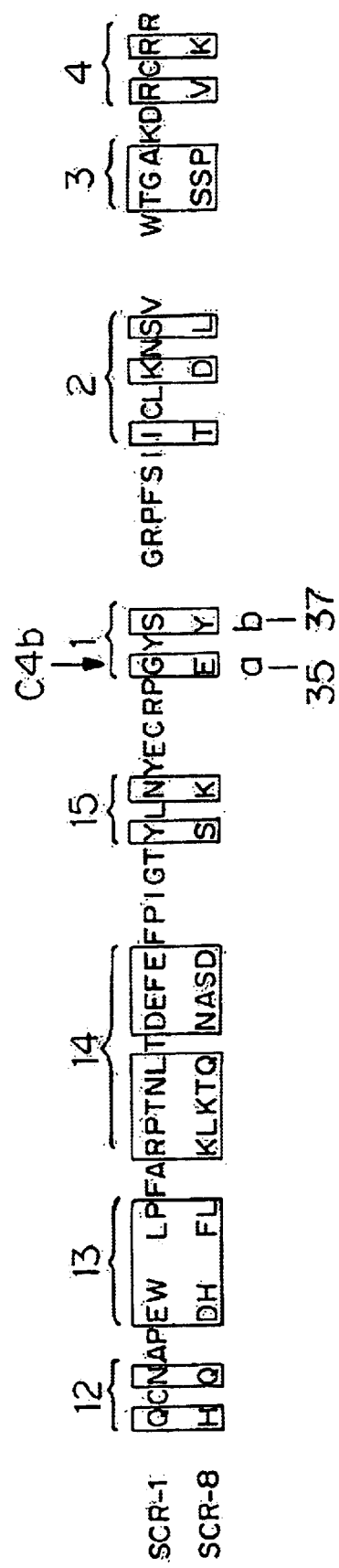
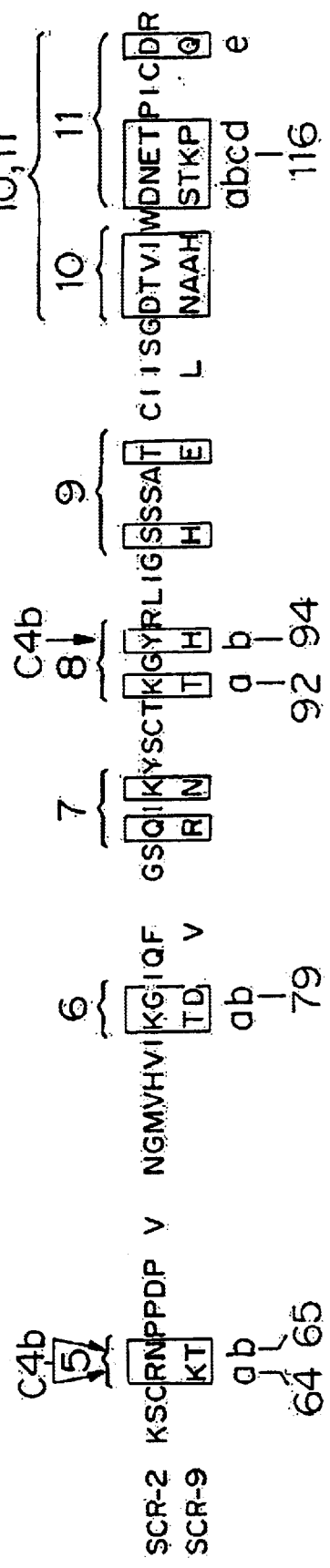
FIG. 2a
FIG. 2b

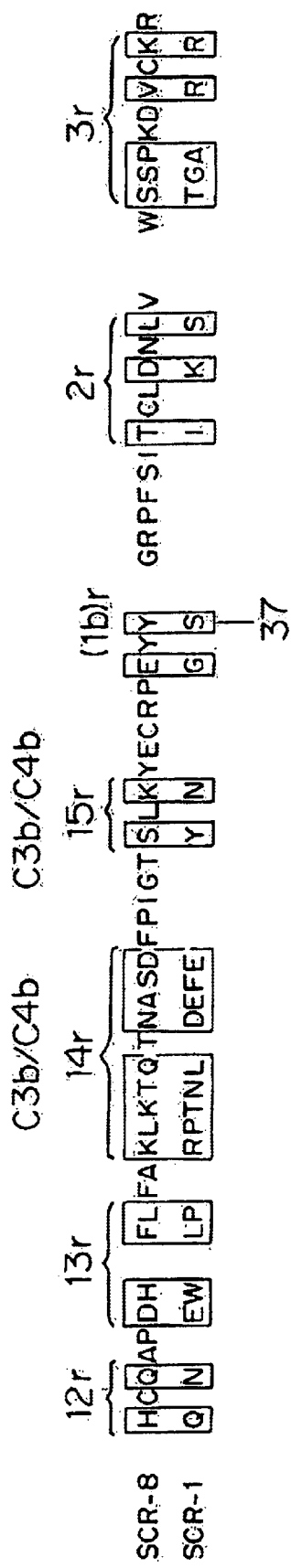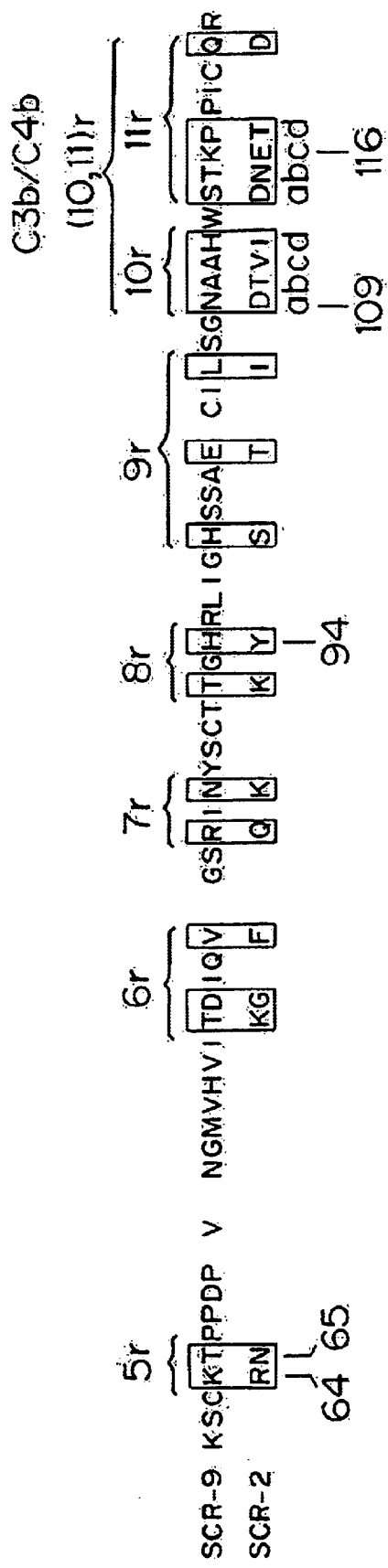
FIG. 3a
FIG. 3b

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 60 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Gln Cys Asn Ala Pro Glu Trp Leu Pro Phe Ala Arg Pro Thr Asn Leu

```
              1               5                  10                 15
Thr Asp Glu Phe Glu Phe Pro Ile Gly Thr Tyr Leu Asn Tyr Glu Cys
                    20                  25                 30
Arg Pro Gly Tyr Ser Gly Arg Pro Phe Ser Ile Ile Cys Leu Lys Asn
                    35                  40                 45
Ser Val Trp Thr Gly Ala Lys Asp Arg Cys Arg Arg
            50                  55                 60
```

(2) INFORMATION FOR SEQ ID NO:2:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
His Cys Gln Ala Pro Asp His Phe Leu Phe Ala Lys Leu Lys Thr Gln
 1               5                  10                 15
Thr Asn Ala Ser Asp Phe Pro Ile Gly Thr Ser Leu Lys Tyr Glu Cys
                    20                  25                 30
Arg Pro Glu Tyr Tyr Gly Arg Pro Phe Ser Ile Thr Cys Leu Asp Asn
                    35                  40                 45
Leu Val Trp Ser Ser Pro Lys Asp Val Cys Lys Arg
            50                  55                 60
```

(2) INFORMATION FOR SEQ ID NO:3:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Lys Ser Cys Arg Asn Pro Pro Asp Pro Val Asn Gly Met Val His Val
 1               5                  10                 15
Ile Lys Gly Ile Gln Phe Gly Ser Gln Ile Lys Tyr Ser Cys Thr Lys
                    20                  25                 30
Gly Tyr Arg Leu Ile Gly Ser Ser Ser Ala Thr Cys Ile Ile Ser Gly
                    35                  40                 45
Asp Thr Val Ile Trp Asp Asn Glu Thr Pro Ile Cys Asp Arg
            50                  55                 60
```

(2) INFORMATION FOR SEQ ID NO:4:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Lys Ser Cys Lys Thr Pro Pro Asp Pro Val Asn Gly Met Val His Val
 1               5                  10                 15
Ile Thr Asp Ile Gln Val Gly Ser Arg Ile Asn Tyr Ser Cys Thr Thr
                    20                  25                 30
```

```
Gly His Arg Leu Ile Gly His Ser Ser Ala Glu Cys Ile Leu Ser Gly
            35                  40                  45

Asn Ala Ala His Trp Ser Thr Lys Pro Pro Ile Cys Gln Arg
            50                  55                  60
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Lys Lys Ala Pro Ile Cys Asp
1               5
```

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ser Asp Pro Leu Pro Glu Cys Arg
1               5
```

(2) INFORMATION FOR SEQ ID NO:7:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ser Ser Val Gln
1
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ser Asp Pro Leu Pro Glu Cys Arg Ser Ser Val Gln
1               5                   10
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear -continued

```
     (ii) MOLECULE TYPE: peptide (xi) SEQUENCE DESCRIPTION: SEQ ID NO:9:

Ser Thr Lys Pro Pro Ile Cys Gln Asn Ala Ala His
1               5                  10

(2) INFORMATION FOR SEQ ID NO:10:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:10:

Gln Pro Tyr Ile Thr Gln Asn Tyr
1               5

(2) INFORMATION FOR SEQ ID NO:11:

(i) SEQUENCE CHARACTERISTICS:
          (A) LENGTH: 43 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:11:

Thr Arg Thr Thr Phe His Leu Gly Arg Lys Cys Ser Thr Ala Val Ser
1               5                  10                  15

Pro Ala Thr Thr Ser Glu Gly Leu Arg Leu Cys Ala Ala His Pro Arg
            20                  25                  30

Glu Thr Gly Ala Leu Gln Pro Pro His Val Lys
        35                  40

(2) INFORMATION FOR SEQ ID NO:12:

(i) SEQUENCE CHARACTERISTICS:
          (A) LENGTH: 6801 base pairs
          (B) TYPE: nucleic acid
          (C) STRANDEDNESS: double
          (D) TOPOLOGY: linear (ii) MOLECULE TYPE: cDNA to mRNA (ix) FEATURE:
          (A) NAME/KEY: CDS
          (B) LOCATION: 1..5994

(xi) SEQUENCE DESCRIPTION: SEQ ID NO:12:

CAA TGC AAT GCC CCA GAA TGG CTT CCA TTT GCC AGG CCT ACC AAC CTA      48
Gln Cys Asn Ala Pro Glu Trp Leu Pro Phe Ala Arg Pro Thr Asn Leu
1               5                  10                  15

ACT GAT GAG TTT GAG TTT CCC ATT GGG ACA TAT CTG AAC TAT GAA TGC      96
Thr Asp Glu Phe Glu Phe Pro Ile Gly Thr Tyr Leu Asn Tyr Glu Cys
            20                  25                  30

CGC CCT GGT TAT TCC GGA AGA CCG TTT TCT ATC ATC TGC CTA AAA AAC     144
Arg Pro Gly Tyr Ser Gly Arg Pro Phe Ser Ile Ile Cys Leu Lys Asn
        35                  40                  45

TCA GTC TGG ACT GGT GCT AAG GAC AGG TGC AGA CGT AAA TCA TGT CGT     192
Ser Val Trp Thr Gly Ala Lys Asp Arg Cys Arg Arg Lys Ser Cys Arg
    50                  55                  60
```

```
                                               -continued

AAT CCT CCA GAT CCT GTG AAT GGC ATG GTG CAT GTG ATC AAA GGC ATC        240
Asn Pro Pro Asp Pro Val Asn Gly Met Val His Val Ile Lys Gly Ile
 65          70                  75                  80

CAG TTC GGA TCC CAA ATT AAA TAT TCT TGT ACT AAA GGA TAC CGA CTC        288
Gln Phe Gly Ser Gln Ile Lys Tyr Ser Cys Thr Lys Gly Tyr Arg Leu
                 85                  90                  95

ATT GGT TCC TCG TCT GCC ACA TGC ATC ATC TCA GGT GAT ACT GTC ATT        336
Ile Gly Ser Ser Ser Ala Thr Cys Ile Ile Ser Gly Asp Thr Val Ile
            100                 105                 110

TGG GAT AAT GAA ACA CCT ATT TGT GAC AGA ATT CCT TGT GGG CTA CCC        384
Trp Asp Asn Glu Thr Pro Ile Cys Asp Arg Ile Pro Cys Gly Leu Pro
        115                 120                 125

CCC ACC ATC ACC AAT GGA GAT TTC ATT AGC ACC AAC AGA GAG AAT TTT        432
Pro Thr Ile Thr Asn Gly Asp Phe Ile Ser Thr Asn Arg Glu Asn Phe
    130                 135                 140

CAC TAT GGA TCA GTG GTG ACC TAC CGC TGC AAT CCT GGA AGC GGA GGG        480
His Tyr Gly Ser Val Val Thr Tyr Arg Cys Asn Pro Gly Ser Gly Gly
145                 150                 155                 160

AGA AAG GTG TTT GAG CTT GTG GGT GAG CCC TCC ATA TAC TGC ACC AGC        528
Arg Lys Val Phe Glu Leu Val Gly Glu Pro Ser Ile Tyr Cys Thr Ser
                165                 170                 175

AAT GAC GAT CAA GTG GGC ATC TGG AGC GGC CCC GCC CCT CAG TGC ATT        576
Asn Asp Asp Gln Val Gly Ile Trp Ser Gly Pro Ala Pro Gln Cys Ile
            180                 185                 190

ATA CCT AAC AAA TGC ACG CCT CCA AAT GTG GAA AAT GGA ATA TTG GTA        624
Ile Pro Asn Lys Cys Thr Pro Pro Asn Val Glu Asn Gly Ile Leu Val
        195                 200                 205

TCT GAC AAC AGA AGC TTA TTT TCC TTA AAT GAA GTT GTG GAG TTT AGG        672
Ser Asp Asn Arg Ser Leu Phe Ser Leu Asn Glu Val Val Glu Phe Arg
    210                 215                 220

TGT CAG CCT GGC TTT GTC ATG AAA GGA CCC CGC CGT GTG AAG TGC CAG        720
Cys Gln Pro Gly Phe Val Met Lys Gly Pro Arg Arg Val Lys Cys Gln
225                 230                 235                 240

GCC CTG AAC AAA TGG GAG CCG GAG CTA CCA AGC TGC TCC AGG GTA TGT        768
Ala Leu Asn Lys Trp Glu Pro Glu Leu Pro Ser Cys Ser Arg Val Cys
                245                 250                 255

CAG CCA CCT CCA GAT GTC CTG CAT GCT GAG CGT ACC CAA AGG GAC AAG        816
Gln Pro Pro Pro Asp Val Leu His Ala Glu Arg Thr Gln Arg Asp Lys
            260                 265                 270

GAC AAC TTT TCA CCT GGG CAG GAA GTG TTC TAC AGC TGT GAG CCC GGC        864
Asp Asn Phe Ser Pro Gly Gln Glu Val Phe Tyr Ser Cys Glu Pro Gly
        275                 280                 285

TAC GAC CTC AGA GGG GCT GCG TCT ATG CGC TGC ACA CCC CAG GGA GAC        912
Tyr Asp Leu Arg Gly Ala Ala Ser Met Arg Cys Thr Pro Gln Gly Asp
    290                 295                 300

TGG AGC CCT GCA GCC CCC ACA TGT GAA GTG AAA TCC TGT GAT GAC TTC        960
Trp Ser Pro Ala Ala Pro Thr Cys Glu Val Lys Ser Cys Asp Asp Phe
305                 310                 315                 320

ATG GGC CAA CTT CTT AAT GGC CGT GTG CTA TTT CCA GTA AAT CTC CAG       1008
Met Gly Gln Leu Leu Asn Gly Arg Val Leu Phe Pro Val Asn Leu Gln
                325                 330                 335

CTT GGA GCA AAA GTG GAT TTT GTT TGT GAT GAA GGA TTT CAA TTA AAA       1056
Leu Gly Ala Lys Val Asp Phe Val Cys Asp Glu Gly Phe Gln Leu Lys
            340                 345                 350

GGC AGC TCT GCT AGT TAC TGT GTC TTG GCT GGA ATG GAA AGC CTT TGG       1104
Gly Ser Ser Ala Ser Tyr Cys Val Leu Ala Gly Met Glu Ser Leu Trp
        355                 360                 365

AAT AGC AGT GTT CCA GTG TGT GAA CAA ATC TTT TGT CCA AGT CCT CCA       1152
Asn Ser Ser Val Pro Val Cys Glu Gln Ile Phe Cys Pro Ser Pro Pro
    370                 375                 380
```

```
GTT ATT CCT AAT GGG AGA CAC ACA GGA AAA CCT CTG GAA GTC TTT CCC        1200
Val Ile Pro Asn Gly Arg His Thr Gly Lys Pro Leu Glu Val Phe Pro
385                 390                 395                 400

TTT GGA AAA GCA GTA AAT TAC ACA TGC GAC CCC CAC CCA GAC AGA GGG        1248
Phe Gly Lys Ala Val Asn Tyr Thr Cys Asp Pro His Pro Asp Arg Gly
                405                 410                 415

ACG AGC TTC GAC CTC ATT GGA GAG AGC ACC ATC CGC TGC ACA AGT GAC        1296
Thr Ser Phe Asp Leu Ile Gly Glu Ser Thr Ile Arg Cys Thr Ser Asp
            420                 425                 430

CCT CAA GGG AAT GGG GTT TGG AGC AGC CCT GCC CCT CGC TGT GGA ATT        1344
Pro Gln Gly Asn Gly Val Trp Ser Ser Pro Ala Pro Arg Cys Gly Ile
        435                 440                 445

CTG GGT CAC TGT CAA GCC CCA GAT CAT TTT CTG TTT GCC AAG TTG AAA        1392
Leu Gly His Cys Gln Ala Pro Asp His Phe Leu Phe Ala Lys Leu Lys
    450                 455                 460

ACC CAA ACC AAT GCA TCT GAC TTT CCC ATT GGG ACA TCT TTA AAG TAC        1440
Thr Gln Thr Asn Ala Ser Asp Phe Pro Ile Gly Thr Ser Leu Lys Tyr
465                 470                 475                 480

GAA TGC CGT CCT GAG TAC TAC GGG AGG CCA TTC TCT ATC ACA TGT CTA        1488
Glu Cys Arg Pro Glu Tyr Tyr Gly Arg Pro Phe Ser Ile Thr Cys Leu
                485                 490                 495

GAT AAC CTG GTC TGG TCA AGT CCC AAA GAT GTC TGT AAA CGT AAA TCA        1536
Asp Asn Leu Val Trp Ser Ser Pro Lys Asp Val Cys Lys Arg Lys Ser
            500                 505                 510

TGT AAA ACT CCT CCA GAT CCA GTG AAT GGC ATG GTG CAT GTG ATC ACA        1584
Cys Lys Thr Pro Pro Asp Pro Val Asn Gly Met Val His Val Ile Thr
        515                 520                 525

GAC ATC CAG GTT GGA TCC AGA ATC AAC TAT TCT TGT ACT ACA GGG CAC        1632
Asp Ile Gln Val Gly Ser Arg Ile Asn Tyr Ser Cys Thr Thr Gly His
    530                 535                 540

CGA CTC ATT GGT CAC TCA TCT GCT GAA TGT ATC CTC TCG GGC AAT GCT        1680
Arg Leu Ile Gly His Ser Ser Ala Glu Cys Ile Leu Ser Gly Asn Ala
545                 550                 555                 560

GCC CAT TGG AGC ACG AAG CCG CCA ATT TGT CAA CGA ATT CCT TGT GGG        1728
Ala His Trp Ser Thr Lys Pro Pro Ile Cys Gln Arg Ile Pro Cys Gly
                565                 570                 575

CTA CCC CCC ACC ATC GCC AAT GGA GAT TTC ATT AGC ACC AAC AGA GAG        1776
Leu Pro Pro Thr Ile Ala Asn Gly Asp Phe Ile Ser Thr Asn Arg Glu
            580                 585                 590

AAT TTT CAC TAT GGA TCA GTG GTG ACC TAC CGC TGC AAT CCT GGA AGC        1824
Asn Phe His Tyr Gly Ser Val Val Thr Tyr Arg Cys Asn Pro Gly Ser
        595                 600                 605

GGA GGG AGA AAG GTG TTT GAG CTT GTG GGT GAG CCC TCC ATA TAC TGC        1872
Gly Gly Arg Lys Val Phe Glu Leu Val Gly Glu Pro Ser Ile Tyr Cys
    610                 615                 620

ACC AGC AAT GAC GAT CAA GTG GGC ATC TGG AGC GGC CCG GCC CCT CAG        1920
Thr Ser Asn Asp Asp Gln Val Gly Ile Trp Ser Gly Pro Ala Pro Gln
625                 630                 635                 640

TGC ATT ATA CCT AAC AAA TGC ACG CCT CCA AAT GTG GAA AAT GGA ATA        1968
Cys Ile Ile Pro Asn Lys Cys Thr Pro Pro Asn Val Glu Asn Gly Ile
                645                 650                 655

TTG GTA TCT GAC AAC AGA AGC TTA TTT TCC TTA AAT GAA GTT GTG GAG        2016
Leu Val Ser Asp Asn Arg Ser Leu Phe Ser Leu Asn Glu Val Val Glu
            660                 665                 670

TTT AGG TGT CAG CCT GGC TTT GTC ATG AAA GGA CCC CGC CGT GTG AAG        2064
Phe Arg Cys Gln Pro Gly Phe Val Met Lys Gly Pro Arg Arg Val Lys
        675                 680                 685

TGC CAG GCC CTG AAC AAA TGG GAG CCG GAG CTA CCA AGC TGC TCC AGG        2112
Cys Gln Ala Leu Asn Lys Trp Glu Pro Glu Leu Pro Ser Cys Ser Arg
```

```
              690                 695                 700
GTA TGT CAG CCA CCT CCA GAT GTC CTG CAT GCT GAG CGT ACC CAA AGG      2160
Val Cys Gln Pro Pro Pro Asp Val Leu His Ala Glu Arg Thr Gln Arg
705                 710                 715                 720

GAC AAG GAC AAC TTT TCA CCC GGG CAG GAA GTG TTC TAC AGC TGT GAG      2208
Asp Lys Asp Asn Phe Ser Pro Gly Gln Glu Val Phe Tyr Ser Cys Glu
                    725                 730                 735

CCC GGC TAT GAC CTC AGA GGG GCT GCG TCT ATG CGC TGC ACA CCC CAG      2256
Pro Gly Tyr Asp Leu Arg Gly Ala Ala Ser Met Arg Cys Thr Pro Gln
                740                 745                 750

GGA GAC TGG AGC CCT GCA GCC CCC ACA TGT GAA GTG AAA TCC TGT GAT      2304
Gly Asp Trp Ser Pro Ala Ala Pro Thr Cys Glu Val Lys Ser Cys Asp
            755                 760                 765

GAC TTC ATG GGC CAA CTT CTT AAT GGC CGT GTG CTA TTT CCA GTA AAT      2352
Asp Phe Met Gly Gln Leu Leu Asn Gly Arg Val Leu Phe Pro Val Asn
770                 775                 780

CTC CAG CTT GGA GCA AAA GTG GAT TTT GTT TGT GAT GAA GGA TTT CAA      2400
Leu Gln Leu Gly Ala Lys Val Asp Phe Val Cys Asp Glu Gly Phe Gln
785                 790                 795                 800

TTA AAA GGC AGC TCT GCT AGT TAT TGT GTC TTG GCT GGA ATG GAA AGC      2448
Leu Lys Gly Ser Ser Ala Ser Tyr Cys Val Leu Ala Gly Met Glu Ser
                    805                 810                 815

CTT TGG AAT AGC AGT GTT CCA GTG TGT GAA CAA ATC TTT TGT CCA AGT      2496
Leu Trp Asn Ser Ser Val Pro Val Cys Glu Gln Ile Phe Cys Pro Ser
                820                 825                 830

CCT CCA GTT ATT CCT AAT GGG AGA CAC ACA GGA AAA CCT CTG GAA GTC      2544
Pro Pro Val Ile Pro Asn Gly Arg His Thr Gly Lys Pro Leu Glu Val
            835                 840                 845

TTT CCC TTT GGA AAA GCA GTA AAT TAC ACA TGC GAC CCC CAC CCA GAC      2592
Phe Pro Phe Gly Lys Ala Val Asn Tyr Thr Cys Asp Pro His Pro Asp
850                 855                 860

AGA GGG ACG AGC TTC GAC CTC ATT GGA GAG AGC ACC ATC CGC TGC ACA      2640
Arg Gly Thr Ser Phe Asp Leu Ile Gly Glu Ser Thr Ile Arg Cys Thr
865                 870                 875                 880

AGT GAC CCT CAA GGG AAT GGG GTT TGG AGC AGC CCT GCC CCT CGC TGT      2688
Ser Asp Pro Gln Gly Asn Gly Val Trp Ser Ser Pro Ala Pro Arg Cys
                    885                 890                 895

GGA ATT CTG GGT CAC TGT CAA GCC CCA GAT CAT TTT CTG TTT GCC AAG      2736
Gly Ile Leu Gly His Cys Gln Ala Pro Asp His Phe Leu Phe Ala Lys
                900                 905                 910

TTG AAA ACC CAA ACC AAT GCA TCT GAC TTT CCC ATT GGG ACA TCT TTA      2784
Leu Lys Thr Gln Thr Asn Ala Ser Asp Phe Pro Ile Gly Thr Ser Leu
            915                 920                 925

AAG TAC GAA TGC CGT CCT GAG TAC TAC GGG AGG CCA TTC TCT ATC ACA      2832
Lys Tyr Glu Cys Arg Pro Glu Tyr Tyr Gly Arg Pro Phe Ser Ile Thr
930                 935                 940

TGT CTA GAT AAC CTG GTC TGG TCA AGT CCC AAA GAT GTC TGT AAA CGT      2880
Cys Leu Asp Asn Leu Val Trp Ser Ser Pro Lys Asp Val Cys Lys Arg
945                 950                 955                 960

AAA TCA TGT AAA ACT CCT CCA GAT CCA GTG AAT GGC ATG GTG CAT GTG      2928
Lys Ser Cys Lys Thr Pro Pro Asp Pro Val Asn Gly Met Val His Val
                    965                 970                 975

ATC ACA GAC ATC CAG GTT GGA TCC AGA ATC AAC TAT TCT TGT ACT ACA      2976
Ile Thr Asp Ile Gln Val Gly Ser Arg Ile Asn Tyr Ser Cys Thr Thr
                980                 985                 990

GGG CAC CGA CTC ATT GGT CAC TCA TCT GCT GAA TGT ATC CTC TCA GGC      3024
Gly His Arg Leu Ile Gly His Ser Ser Ala Glu Cys Ile Leu Ser Gly
            995                 1000                1005

AAT ACT GCC CAT TGG AGC ACG AAG CCG CCA ATT TGT CAA CGA ATT CCT      3072
```

```
          Asn Thr Ala His Trp Ser Thr Lys Pro Pro Ile Cys Gln Arg Ile Pro
                   1010                1015                1020

TGT GGG CTA CCC CCA ACC ATC GCC AAT GGA GAT TTC ATT AGC ACC AAC         3120
Cys Gly Leu Pro Pro Thr Ile Ala Asn Gly Asp Phe Ile Ser Thr Asn
1025                1030                1035                1040

AGA GAG AAT TTT CAC TAT GGA TCA GTG GTG ACC TAC CGC TGC AAT CTT         3168
Arg Glu Asn Phe His Tyr Gly Ser Val Val Thr Tyr Arg Cys Asn Leu
                1045                1050                1055

GGA AGC AGA GGG AGA AAG GTG TTT GAG CTT GTG GGT GAG CCC TCC ATA         3216
Gly Ser Arg Gly Arg Lys Val Phe Glu Leu Val Gly Glu Pro Ser Ile
                1060                1065                1070

TAC TGC ACC AGC AAT GAC GAT CAA GTG GGC ATC TGG AGC GGC CCC GCC         3264
Tyr Cys Thr Ser Asn Asp Asp Gln Val Gly Ile Trp Ser Gly Pro Ala
                1075                1080                1085

CCT CAG TGC ATT ATA CCT AAC AAA TGC ACG CCT CCA AAT GTG GAA AAT         3312
Pro Gln Cys Ile Ile Pro Asn Lys Cys Thr Pro Pro Asn Val Glu Asn
        1090                1095                1100

GGA ATA TTG GTA TCT GAC AAC AGA AGC TTA TTT TCC TTA AAT GAA GTT         3360
Gly Ile Leu Val Ser Asp Asn Arg Ser Leu Phe Ser Leu Asn Glu Val
1105                1110                1115                1120

GTG GAG TTT AGG TGT CAG CCT GGC TTT GTC ATG AAA GGA CCC CGC CGT         3408
Val Glu Phe Arg Cys Gln Pro Gly Phe Val Met Lys Gly Pro Arg Arg
                1125                1130                1135

GTG AAG TGC CAG GCC CTG AAC AAA TGG GAG CCA GAG TTA CCA AGC TGC         3456
Val Lys Cys Gln Ala Leu Asn Lys Trp Glu Pro Glu Leu Pro Ser Cys
                1140                1145                1150

TCC AGG GTG TGT CAG CCG CCT CCA GAA ATC CTG CAT GGT GAG CAT ACC         3504
Ser Arg Val Cys Gln Pro Pro Pro Glu Ile Leu His Gly Glu His Thr
                1155                1160                1165

CCA AGC CAT CAG GAC AAC TTT TCA CCT GGG CAG GAA GTG TTC TAC AGC         3552
Pro Ser His Gln Asp Asn Phe Ser Pro Gly Gln Glu Val Phe Tyr Ser
        1170                1175                1180

TGT GAG CCT GGC TAT GAC CTC AGA GGG GCT GCG TCT CTG CAC TGC ACA         3600
Cys Glu Pro Gly Tyr Asp Leu Arg Gly Ala Ala Ser Leu His Cys Thr
1185                1190                1195                1200

CCC CAG GGA GAC TGG AGC CCT GAA GCC CCG AGA TGT GCA GTG AAA TCC         3648
Pro Gln Gly Asp Trp Ser Pro Glu Ala Pro Arg Cys Ala Val Lys Ser
                1205                1210                1215

TGT GAT GAC TTC TTG GGT CAA CTC CCT CAT GGC CGT GTG CTA TTT CCA         3696
Cys Asp Asp Phe Leu Gly Gln Leu Pro His Gly Arg Val Leu Phe Pro
                1220                1225                1230

CTT AAT CTC CAG CTT GGG GCA AAG GTG TCC TTT GTC TGT GAT GAA GGG         3744
Leu Asn Leu Gln Leu Gly Ala Lys Val Ser Phe Val Cys Asp Glu Gly
                1235                1240                1245

TTT CGC TTA AAG GGC AGT TCC GTT AGT CAT TGT GTC TTG GTT GGA ATG         3792
Phe Arg Leu Lys Gly Ser Ser Val Ser His Cys Val Leu Val Gly Met
        1250                1255                1260

AGA AGC CTT TGG AAT AAC AGT GTT CCT GTG TGT GAA CAT ATC TTT TGT         3840
Arg Ser Leu Trp Asn Asn Ser Val Pro Val Cys Glu His Ile Phe Cys
1265                1270                1275                1280

CCA AAT CCT CCA GCT ATC CTT AAT GGG AGA CAC ACA GGA ACT CCC TCT         3888
Pro Asn Pro Pro Ala Ile Leu Asn Gly Arg His Thr Gly Thr Pro Ser
                1285                1290                1295

GGA GAT ATT CCC TAT GGA AAA GAA ATA TCT TAC ACA TGT GAC CCC CAC         3936
Gly Asp Ile Pro Tyr Gly Lys Glu Ile Ser Tyr Thr Cys Asp Pro His
                1300                1305                1310

CCA GAC AGA GGG ATG ACC TTC AAC CTC ATT GGG GAG AGC ACC ATC CGC         3984
Pro Asp Arg Gly Met Thr Phe Asn Leu Ile Gly Glu Ser Thr Ile Arg
                1315                1320                1325
```

```
TGC ACA AGT GAC CCT CAT GGG AAT GGG GTT TGG AGC AGC CCT GCC CCT    4032
Cys Thr Ser Asp Pro His Gly Asn Gly Val Trp Ser Ser Pro Ala Pro
    1330            1335            1340

CGC TGT GAA CTT TCT GTT CGT GCT GGT CAC TGT AAA ACC CCA GAG CAG    4080
Arg Cys Glu Leu Ser Val Arg Ala Gly His Cys Lys Thr Pro Glu Gln
1345            1350            1355            1360

TTT CCA TTT GCC AGT CCT ACG ATC CCA ATT AAT GAC TTT GAG TTT CCA    4128
Phe Pro Phe Ala Ser Pro Thr Ile Pro Ile Asn Asp Phe Glu Phe Pro
            1365            1370            1375

GTC GGG ACA TCT TTG AAT TAT GAA TGC CGT CCT GGG TAT TTT GGG AAA    4176
Val Gly Thr Ser Leu Asn Tyr Glu Cys Arg Pro Gly Tyr Phe Gly Lys
        1380            1385            1390

ATG TTC TCT ATC TCC TGC CTA GAA AAC TTG GTC TGG TCA AGT GTT GAA    4224
Met Phe Ser Ile Ser Cys Leu Glu Asn Leu Val Trp Ser Ser Val Glu
    1395            1400            1405

GAC AAC TGT AGA CGA AAA TCA TGT GGA CCT CCA CCA GAA CCC TTC AAT    4272
Asp Asn Cys Arg Arg Lys Ser Cys Gly Pro Pro Pro Glu Pro Phe Asn
1410            1415            1420

GGA ATG GTG CAT ATA AAC ACA GAT ACA CAG TTT GGA TCA ACA GTT AAT    4320
Gly Met Val His Ile Asn Thr Asp Thr Gln Phe Gly Ser Thr Val Asn
1425            1430            1435            1440

TAT TCT TGT AAT GAA GGG TTT CGA CTC ATT GGT TCC CCA TCT ACT ACT    4368
Tyr Ser Cys Asn Glu Gly Phe Arg Leu Ile Gly Ser Pro Ser Thr Thr
            1445            1450            1455

TGT CTC GTC TCA GGC AAT AAT GTC ACA TGG GAT AAG AAG GCA CCT ATT    4416
Cys Leu Val Ser Gly Asn Asn Val Thr Trp Asp Lys Lys Ala Pro Ile
        1460            1465            1470

TGT GAG ATC ATA TCT TGT GAG CCA CCT CCA ACC ATA TCC AAT GGA GAC    4464
Cys Glu Ile Ile Ser Cys Glu Pro Pro Pro Thr Ile Ser Asn Gly Asp
    1475            1480            1485

TTC TAC AGC AAC AAT AGA ACA TCT TTT CAC AAT GGA ACG GTG GTA ACT    4512
Phe Tyr Ser Asn Asn Arg Thr Ser Phe His Asn Gly Thr Val Val Thr
1490            1495            1500

TAC CAG TGC CAC ACT GGA CCA GAT GGA GAA CAG CTG TTT GAG CTT GTG    4560
Tyr Gln Cys His Thr Gly Pro Asp Gly Glu Gln Leu Phe Glu Leu Val
1505            1510            1515            1520

GGA GAA CGG TCA ATA TAT TGC ACC AGC AAA GAT GAT CAA GTT GGT GTT    4608
Gly Glu Arg Ser Ile Tyr Cys Thr Ser Lys Asp Asp Gln Val Gly Val
            1525            1530            1535

TGG AGC AGC CCT CCC CCT CGG TGT ATT TCT ACT AAT AAA TGC ACA GCT    4656
Trp Ser Ser Pro Pro Pro Arg Cys Ile Ser Thr Asn Lys Cys Thr Ala
        1540            1545            1550

CCA GAA GTT GAA AAT GCA ATT AGA GTA CCA GGA AAC AGG AGT TTC TTT    4704
Pro Glu Val Glu Asn Ala Ile Arg Val Pro Gly Asn Arg Ser Phe Phe
    1555            1560            1565

TCC CTC ACT GAG ATC ATC AGA TTT AGA TGT CAG CCC GGG TTT GTC ATG    4752
Ser Leu Thr Glu Ile Ile Arg Phe Arg Cys Gln Pro Gly Phe Val Met
1570            1575            1580

GTA GGG TCC CAC ACT GTG CAG TGC CAG ACC AAT GGC AGA TGG GGG CCC    4800
Val Gly Ser His Thr Val Gln Cys Gln Thr Asn Gly Arg Trp Gly Pro
1585            1590            1595            1600

AAG CTG CCA CAC TGC TCC AGG GTG TGT CAG CCG CCT CCA GAA ATC CTG    4848
Lys Leu Pro His Cys Ser Arg Val Cys Gln Pro Pro Pro Glu Ile Leu
            1605            1610            1615

CAT GGT GAG CAT ACC CTA AGC CAT CAG GAC AAC TTT TCA CCT GGG CAG    4896
His Gly Glu His Thr Leu Ser His Gln Asp Asn Phe Ser Pro Gly Gln
        1620            1625            1630

GAA GTG TTC TAC AGC TGT GAG CCC AGC TAT GAC CTC AGA GGG GCT GCG    4944
Glu Val Phe Tyr Ser Cys Glu Pro Ser Tyr Asp Leu Arg Gly Ala Ala
    1635            1640            1645
```

-continued

```
TCT CTG CAC TGC ACG CCC CAG GGA GAC TGG AGC CCT GAA GCC CCT AGA        4992
Ser Leu His Cys Thr Pro Gln Gly Asp Trp Ser Pro Glu Ala Pro Arg
    1650                1655                1660

TGT ACA GTG AAA TCC TGT GAT GAC TTC CTG GGC CAA CTC CCT CAT GGC        5040
Cys Thr Val Lys Ser Cys Asp Asp Phe Leu Gly Gln Leu Pro His Gly
1665                1670                1675                1680

CGT GTG CTA CTT CCA CTT AAT CTC CAG CTT GGG GCA AAG GTG TCC TTT        5088
Arg Val Leu Leu Pro Leu Asn Leu Gln Leu Gly Ala Lys Val Ser Phe
                1685                1690                1695

GTT TGC GAT GAA GGG TTC CGA TTA AAA GGC AGG TCT GCT AGT CAT TGT        5136
Val Cys Asp Glu Gly Phe Arg Leu Lys Gly Arg Ser Ala Ser His Cys
            1700                1705                1710

GTC TTG GCT GGA ATG AAA GCC CTT TGG AAT AGC AGT GTT CCA GTG TGT        5184
Val Leu Ala Gly Met Lys Ala Leu Trp Asn Ser Ser Val Pro Val Cys
        1715                1720                1725

GAA CAA ATC TTT TGT CCA AAT CCT CCA GCT ATC CTT AAT GGG AGA CAC        5232
Glu Gln Ile Phe Cys Pro Asn Pro Pro Ala Ile Leu Asn Gly Arg His
    1730                1735                1740

ACA GGA ACT CCC TTT GGA GAT ATT CCC TAT GGA AAA GAA ATA TCT TAC        5280
Thr Gly Thr Pro Phe Gly Asp Ile Pro Tyr Gly Lys Glu Ile Ser Tyr
1745                1750                1755                1760

GCA TGC GAC ACC CAC CCA GAC AGA GGG ATG ACC TTC AAC CTC ATT GGG        5328
Ala Cys Asp Thr His Pro Asp Arg Gly Met Thr Phe Asn Leu Ile Gly
                1765                1770                1775

GAG AGC TCC ATC CGC TGC ACA AGT GAC CCT CAA GGG AAT GGG GTT TGG        5376
Glu Ser Ser Ile Arg Cys Thr Ser Asp Pro Gln Gly Asn Gly Val Trp
            1780                1785                1790

AGC AGC CCT GCC CCT CGC TGT GAA CTT TCT GTT CCT GCT GCC TGC CCA        5424
Ser Ser Pro Ala Pro Arg Cys Glu Leu Ser Val Pro Ala Ala Cys Pro
        1795                1800                1805

CAT CCA CCC AAG ATC CAA AAC GGG CAT TAC ATT GGA GGA CAC GTA TCT        5472
His Pro Pro Lys Ile Gln Asn Gly His Tyr Ile Gly Gly His Val Ser
    1810                1815                1820

CTA TAT CTT CCT GGG ATG ACA ATC AGC TAC ACT TGT GAC CCC GGC TAC        5520
Leu Tyr Leu Pro Gly Met Thr Ile Ser Tyr Thr Cys Asp Pro Gly Tyr
1825                1830                1835                1840

CTG TTA GTG GGA AAG GGC TTC ATT TTC TGT ACA GAC CAG GGA ATC TGG        5568
Leu Leu Val Gly Lys Gly Phe Ile Phe Cys Thr Asp Gln Gly Ile Trp
                1845                1850                1855

AGC CAA TTG GAT CAT TAT TGC AAA GAA GTA AAT TGT AGC TTC CCA CTG        5616
Ser Gln Leu Asp His Tyr Cys Lys Glu Val Asn Cys Ser Phe Pro Leu
            1860                1865                1870

TTT ATG AAT GGA ATC TCG AAG GAG TTA GAA ATG AAA AAA GTA TAT CAC        5664
Phe Met Asn Gly Ile Ser Lys Glu Leu Glu Met Lys Lys Val Tyr His
        1875                1880                1885

TAT GGA GAT TAT GTG ACT TTG AAG TGT GAA GAT GGG TAT ACT CTG GAA        5712
Tyr Gly Asp Tyr Val Thr Leu Lys Cys Glu Asp Gly Tyr Thr Leu Glu
    1890                1895                1900

GGC AGT CCC TGG AGC CAG TGC CAG GCG GAT GAC AGA TGG GAC CCT CCT        5760
Gly Ser Pro Trp Ser Gln Cys Gln Ala Asp Asp Arg Trp Asp Pro Pro
1905                1910                1915                1920

CTG GCC AAA TGT ACC TCT CGT GCA CAT GAT GCT CTC ATA GTT GGC ACT        5808
Leu Ala Lys Cys Thr Ser Arg Ala His Asp Ala Leu Ile Val Gly Thr
                1925                1930                1935

TTA TCT GGT ACG ATC TTC TTT ATT TTA CTC ATC ATT TTC CTC TCT TGG        5856
Leu Ser Gly Thr Ile Phe Phe Ile Leu Leu Ile Ile Phe Leu Ser Trp
            1940                1945                1950

ATA ATT CTA AAG CAC AGA AAA GGC AAT AAT GCA CAT GAA AAC CCT AAA        5904
Ile Ile Leu Lys His Arg Lys Gly Asn Asn Ala His Glu Asn Pro Lys
```

```
                             1955                 1960                 1965
GAA GTG GCT ATC CAT TTA CAT TCT CAA GGA GGC AGC AGC GTT CAT CCC       5952
Glu Val Ala Ile His Leu His Ser Gln Gly Gly Ser Ser Val His Pro
            1970                     1975                 1980

CGA ACT CTG CAA ACA AAT GAA GAA AAT AGC AGG GTC CTT CCT              5994
Arg Thr Leu Gln Thr Asn Glu Glu Asn Ser Arg Val Leu Pro
1985                    1990                1995

TGACAAAGTA CTATACAGCT GAAGAACATC TCGAATACAA TTTTGGTGGG AAAGGAGCCA    6054

ATTGATTTCA ACAGAATCAG ATCTGAGCTT CATAAAGTCT TTGAAGTGAC TTCACAGAGA    6114

CGCAGACATG TGCACTTGAA GATGCTGCCC CTTCCCTGGT ACCTAGCAAA GCTCCTGCCT    6174

CTTTGTGTGC GTCACTGTGA AACCCCCACC CTTCTGCCTC GTGCTAAACG CACACAGTAT    6234

CTAGTCAGGG GAAAAGACTG CATTTAGGAG ATAGAAAATA GTTTGGATTA CTTAAAGGAA    6294

TAAGGTGTTG CCTGGAATTT CTGGTTTGTA AGGTGGTCAC TGTTCTTTTT TAAAATATTT    6354

GTAATATGGA ATGGGCTCAG TAAGAAGAGC TTGGAAAATG CAGAAAGTTA TGAAAAATAA    6414

GTCACTTATA ATTATGCTAC CTACTGATAA CCACTCCTAA TATTTTGATT CATTTTCTGC    6474

CTATCTTCTT TCACATATGT GTTTTTTTAC ATACGTACTT TTCCCCCCTT AGTTTGTTTC    6534

CTTTTATTTT ATAGAGCAGA ACCCTAGTCT TTTAAACAGT TTAGAGTGAA ATATATGCTA    6594

TATCAGTTTT TACTTTCTCT AGGGAGAAAA ATTAATTTAC TAGAAAGGCA TGAAATGATC    6654

ATGGGAAGAG TGGTTAAGAC TACTGAAGAG AAATATTTGG AAAATAAGAT TTCGATATCT    6714

TCTTTTTTTT TGAGATGGAG TCTGGCTCTG TCTCCCAGGC TGGAGTGCAG TGGCGTAATC    6774

TCGGCTCACT GCAACGTCCG CCTCCCG                                        6801

(2) INFORMATION FOR SEQ ID NO:13:

(i) SEQUENCE CHARACTERISTICS:
        (A) LENGTH: 1998 amino acids
        (B) TYPE: amino acid
        (D) TOPOLOGY: linear (ii) MOLECULE TYPE: protein (xi) SEQUENCE DESCRIPTION: SEQ ID NO:13:

Gln Cys Asn Ala Pro Glu Trp Leu Pro Phe Ala Arg Pro Thr Asn Leu
  1               5                  10                  15

Thr Asp Glu Phe Glu Phe Pro Ile Gly Thr Tyr Leu Asn Tyr Glu Cys
                 20                  25                  30

Arg Pro Gly Tyr Ser Gly Arg Pro Phe Ser Ile Ile Cys Leu Lys Asn
             35                  40                  45

Ser Val Trp Thr Gly Ala Lys Asp Arg Cys Arg Arg Lys Ser Cys Arg
 50                  55                  60

Asn Pro Pro Asp Pro Val Asn Gly Met Val His Val Ile Lys Gly Ile
 65                  70                  75                  80

Gln Phe Gly Ser Gln Ile Lys Tyr Ser Cys Thr Lys Gly Tyr Arg Leu
                 85                  90                  95

Ile Gly Ser Ser Ser Ala Thr Cys Ile Ile Ser Gly Asp Thr Val Ile
            100                 105                 110

Trp Asp Asn Glu Thr Pro Ile Cys Asp Arg Ile Pro Cys Gly Leu Pro
            115                 120                 125

Pro Thr Ile Thr Asn Gly Asp Phe Ile Ser Thr Asn Arg Glu Asn Phe
            130                 135                 140

His Tyr Gly Ser Val Val Thr Tyr Arg Cys Asn Pro Gly Ser Gly Gly
145                 150                 155                 160
```

-continued

```
Arg Lys Val Phe Glu Leu Val Gly Glu Pro Ser Ile Tyr Cys Thr Ser
            165                 170                 175
Asn Asp Asp Gln Val Gly Ile Trp Ser Gly Ala Pro Gln Cys Ile
        180                 185                 190
Ile Pro Asn Lys Cys Thr Pro Pro Asn Val Glu Asn Gly Ile Leu Val
        195                 200                 205
Ser Asp Asn Arg Ser Leu Phe Ser Leu Asn Glu Val Val Glu Phe Arg
    210                 215                 220
Cys Gln Pro Gly Phe Val Met Lys Gly Pro Arg Arg Val Lys Cys Gln
225                 230                 235                 240
Ala Leu Asn Lys Trp Glu Pro Glu Leu Pro Ser Cys Ser Arg Val Cys
            245                 250                 255
Gln Pro Pro Pro Asp Val Leu His Ala Glu Arg Thr Gln Arg Asp Lys
            260                 265                 270
Asp Asn Phe Ser Pro Gly Gln Glu Val Phe Tyr Ser Cys Glu Pro Gly
        275                 280                 285
Tyr Asp Leu Arg Gly Ala Ala Ser Met Arg Cys Thr Pro Gln Gly Asp
    290                 295                 300
Trp Ser Pro Ala Ala Pro Thr Cys Glu Val Lys Ser Cys Asp Asp Phe
305                 310                 315                 320
Met Gly Gln Leu Leu Asn Gly Arg Val Leu Phe Pro Val Asn Leu Gln
            325                 330                 335
Leu Gly Ala Lys Val Asp Phe Val Cys Asp Glu Gly Phe Gln Leu Lys
            340                 345                 350
Gly Ser Ser Ala Ser Tyr Cys Val Leu Ala Gly Met Glu Ser Leu Trp
        355                 360                 365
Asn Ser Ser Val Pro Val Cys Glu Gln Ile Phe Cys Pro Ser Pro Pro
    370                 375                 380
Val Ile Pro Asn Gly Arg His Thr Gly Lys Pro Leu Glu Val Phe Pro
385                 390                 395                 400
Phe Gly Lys Ala Val Asn Tyr Thr Cys Asp Pro His Pro Asp Arg Gly
            405                 410                 415
Thr Ser Phe Asp Leu Ile Gly Glu Ser Thr Ile Arg Cys Thr Ser Asp
            420                 425                 430
Pro Gln Gly Asn Gly Val Trp Ser Ser Pro Ala Pro Arg Cys Gly Ile
        435                 440                 445
Leu Gly His Cys Gln Ala Pro Asp His Phe Leu Phe Ala Lys Leu Lys
    450                 455                 460
Thr Gln Thr Asn Ala Ser Asp Phe Pro Ile Gly Thr Ser Leu Lys Tyr
465                 470                 475                 480
Glu Cys Arg Pro Glu Tyr Tyr Gly Arg Pro Phe Ser Ile Thr Cys Leu
            485                 490                 495
Asp Asn Leu Val Trp Ser Ser Pro Lys Asp Val Cys Lys Arg Lys Ser
            500                 505                 510
Cys Lys Thr Pro Pro Asp Pro Val Asn Gly Met Val His Val Ile Thr
        515                 520                 525
Asp Ile Gln Val Gly Ser Arg Ile Asn Tyr Ser Cys Thr Thr Gly His
    530                 535                 540
Arg Leu Ile Gly His Ser Ser Ala Glu Cys Ile Leu Ser Gly Asn Ala
545                 550                 555                 560
Ala His Trp Ser Thr Lys Pro Pro Ile Cys Gln Arg Ile Pro Cys Gly
            565                 570                 575
```

-continued

```
Leu Pro Pro Thr Ile Ala Asn Gly Asp Phe Ile Ser Thr Asn Arg Glu
            580                 585                 590

Asn Phe His Tyr Gly Ser Val Thr Tyr Arg Cys Asn Pro Gly Ser
        595                 600                 605

Gly Gly Arg Lys Val Phe Glu Leu Val Gly Pro Ser Ile Tyr Cys
    610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
                645                 650                 655

Leu Val Ser Asp Asn Arg Ser Leu Phe Ser Leu Asn Glu Val Val Glu
            660                 665                 670

Phe Arg Cys Gln Pro Gly Phe Val Met Lys Gly Pro Arg Arg Val Lys
        675                 680                 685

Cys Gln Ala Leu Asn Lys Trp Glu Pro Glu Leu Pro Ser Cys Ser Arg
690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
                725                 730                 735

Pro Gly Tyr Asp Leu Arg Gly Ala Ala Ser Met Arg Cys Thr Pro Gln
            740                 745                 750

Gly Asp Trp Ser Pro Ala Ala Pro Thr Cys Glu Val Lys Ser Cys Asp
            755                 760                 765

Asp Phe Met Gly Gln Leu Leu Asn Gly Arg Val Leu Phe Pro Val Asn
770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser
                805                 810                 815

Leu Trp Asn Ser Ser Val Pro Val Cys Glu Gln Ile Phe Cys Pro Ser
            820                 825                 830

Pro Pro Val Ile Pro Asn Gly Arg His Thr Gly Lys Pro Leu Glu Val
            835                 840                 845

Phe Pro Phe Gly Lys Ala Val Asn Tyr Thr Cys Asp Pro His Pro Asp
        850                 855                 860

Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Ser Pro Ala Pro Arg Cys
                885                 890                 895

Gly Ile Leu Gly His Cys Gln Ala Pro Asp His Phe Leu Phe Ala Lys
            900                 905                 910

Leu Lys Thr Gln Thr Asn Ala Ser Asp Phe Pro Ile Gly Thr Ser Leu
        915                 920                 925

Lys Tyr Glu Cys Arg Pro Glu Tyr Tyr Gly Arg Pro Phe Ser Ile Thr
    930                 935                 940

Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
                965                 970                 975

Ile Thr Asp Ile Gln Val Gly Ser Arg Ile Asn Tyr Ser Cys Thr Thr
            980                 985                 990

Gly His Arg Leu Ile Gly His Ser Ser Ala Glu Cys Ile Leu Ser Gly
```

```
                995                 1000                1005
Asn Thr Ala His Trp Ser Thr Lys Pro Pro Ile Cys Gln Arg Ile Pro
    1010                1015                1020
Cys Gly Leu Pro Pro Thr Ile Ala Asn Gly Asp Phe Ile Ser Thr Asn
1025                1030                1035                1040
Arg Glu Asn Phe His Tyr Gly Ser Val Val Thr Tyr Arg Cys Asn Leu
                1045                1050                1055
Gly Ser Arg Gly Arg Lys Val Phe Glu Leu Val Gly Glu Pro Ser Ile
                1060                1065                1070
Tyr Cys Thr Ser Asn Asp Asp Gln Val Gly Ile Trp Ser Gly Pro Ala
            1075                1080                1085
Pro Gln Cys Ile Ile Pro Asn Lys Cys Thr Pro Pro Asn Val Glu Asn
            1090                1095                1100
Gly Ile Leu Val Ser Asp Asn Arg Ser Leu Phe Ser Leu Asn Glu Val
1105                1110                1115                1120
Val Glu Phe Arg Cys Gln Pro Gly Phe Val Met Lys Gly Pro Arg Arg
                1125                1130                1135
Val Lys Cys Gln Ala Leu Asn Lys Trp Glu Pro Glu Leu Pro Ser Cys
            1140                1145                1150
Ser Arg Val Cys Gln Pro Pro Pro Glu Ile Leu His Gly Glu His Thr
            1155                1160                1165
Pro Ser His Gln Asp Asn Phe Ser Pro Gly Gln Glu Val Phe Tyr Ser
        1170                1175                1180
Cys Glu Pro Gly Tyr Asp Leu Arg Gly Ala Ala Ser Leu His Cys Thr
1185                1190                1195                1200
Pro Gln Gly Asp Trp Ser Pro Glu Ala Pro Arg Cys Ala Val Lys Ser
                1205                1210                1215
Cys Asp Asp Phe Leu Gly Gln Leu Pro His Gly Arg Val Leu Phe Pro
            1220                1225                1230
Leu Asn Leu Gln Leu Gly Ala Lys Val Ser Phe Val Cys Asp Glu Gly
            1235                1240                1245
Phe Arg Leu Lys Gly Ser Ser Val Ser His Cys Val Leu Val Gly Met
        1250                1255                1260
Arg Ser Leu Trp Asn Asn Ser Val Pro Val Cys Glu His Ile Phe Cys
1265                1270                1275                1280
Pro Asn Pro Pro Ala Ile Leu Asn Gly Arg His Thr Gly Thr Pro Ser
                1285                1290                1295
Gly Asp Ile Pro Tyr Gly Lys Glu Ile Ser Tyr Thr Cys Asp Pro His
            1300                1305                1310
Pro Asp Arg Gly Met Thr Phe Asn Leu Ile Gly Glu Ser Thr Ile Arg
            1315                1320                1325
Cys Thr Ser Asp Pro His Gly Asn Gly Val Trp Ser Ser Pro Ala Pro
        1330                1335                1340
Arg Cys Glu Leu Ser Val Arg Ala Gly His Cys Lys Thr Pro Glu Gln
1345                1350                1355                1360
Phe Pro Phe Ala Ser Pro Thr Ile Pro Ile Asn Asp Phe Glu Phe Pro
            1365                1370                1375
Val Gly Thr Ser Leu Asn Tyr Glu Cys Arg Pro Gly Tyr Phe Gly Lys
            1380                1385                1390
Met Phe Ser Ile Ser Cys Leu Glu Asn Leu Val Trp Ser Ser Val Glu
        1395                1400                1405
Asp Asn Cys Arg Arg Lys Ser Cys Gly Pro Pro Pro Glu Pro Phe Asn
        1410                1415                1420
```

```
Gly Met Val His Ile Asn Thr Asp Thr Gln Phe Gly Ser Thr Val Asn
1425                1430                1435                1440

Tyr Ser Cys Asn Glu Gly Phe Arg Leu Ile Gly Ser Pro Ser Thr Thr
            1445                1450                1455

Cys Leu Val Ser Gly Asn Asn Val Thr Trp Asp Lys Lys Ala Pro Ile
            1460                1465                1470

Cys Glu Ile Ile Ser Cys Glu Pro Pro Thr Ile Ser Asn Gly Asp
    1475                1480                1485

Phe Tyr Ser Asn Asn Arg Thr Ser Phe His Asn Gly Thr Val Val Thr
    1490                1495                1500

Tyr Gln Cys His Thr Gly Pro Asp Gly Glu Gln Leu Phe Glu Leu Val
1505                1510                1515                1520

Gly Glu Arg Ser Ile Tyr Cys Thr Ser Lys Asp Asp Gln Val Gly Val
                1525                1530                1535

Trp Ser Ser Pro Pro Pro Arg Cys Ile Ser Thr Asn Lys Cys Thr Ala
            1540                1545                1550

Pro Glu Val Glu Asn Ala Ile Arg Val Pro Gly Asn Arg Ser Phe Phe
    1555                1560                1565

Ser Leu Thr Glu Ile Ile Arg Phe Arg Cys Gln Pro Gly Phe Val Met
    1570                1575                1580

Val Gly Ser His Thr Val Gln Cys Gln Thr Asn Gly Arg Trp Gly Pro
1585                1590                1595                1600

Lys Leu Pro His Cys Ser Arg Val Cys Gln Pro Pro Pro Glu Ile Leu
                1605                1610                1615

His Gly Glu His Thr Leu Ser His Gln Asp Asn Phe Ser Pro Gly Gln
                1620                1625                1630

Glu Val Phe Tyr Ser Cys Glu Pro Ser Tyr Asp Leu Arg Gly Ala Ala
    1635                1640                1645

Ser Leu His Cys Thr Pro Gln Gly Asp Trp Ser Pro Glu Ala Pro Arg
    1650                1655                1660

Cys Thr Val Lys Ser Cys Asp Asp Phe Leu Gly Gln Leu Pro His Gly
1665                1670                1675                1680

Arg Val Leu Leu Pro Leu Asn Leu Gln Leu Gly Ala Lys Val Ser Phe
                1685                1690                1695

Val Cys Asp Glu Gly Phe Arg Leu Lys Gly Arg Ser Ala Ser His Cys
    1700                1705                1710

Val Leu Ala Gly Met Lys Ala Leu Trp Asn Ser Ser Val Pro Val Cys
    1715                1720                1725

Glu Gln Ile Phe Cys Pro Asn Pro Pro Ala Ile Leu Asn Gly Arg His
    1730                1735                1740

Thr Gly Thr Pro Phe Gly Asp Ile Pro Tyr Gly Lys Glu Ile Ser Tyr
1745                1750                1755                1760

Ala Cys Asp Thr His Pro Asp Arg Gly Met Thr Phe Asn Leu Ile Gly
                1765                1770                1775

Glu Ser Ser Ile Arg Cys Thr Ser Asp Pro Gln Gly Asn Gly Val Trp
                1780                1785                1790

Ser Ser Pro Ala Pro Arg Cys Glu Leu Ser Val Pro Ala Ala Cys Pro
            1795                1800                1805

His Pro Pro Lys Ile Gln Asn Gly His Tyr Ile Gly Gly His Val Ser
    1810                1815                1820

Leu Tyr Leu Pro Gly Met Thr Ile Ser Tyr Thr Cys Asp Pro Gly Tyr
1825                1830                1835                1840
```

```
Leu Leu Val Gly Lys Gly Phe Ile Phe Cys Thr Asp Gln Gly Ile Trp
            1845            1850            1855

Ser Gln Leu Asp His Tyr Cys Lys Glu Val Asn Cys Ser Phe Pro Leu
            1860            1865            1870

Phe Met Asn Gly Ile Ser Lys Glu Leu Glu Met Lys Lys Val Tyr His
            1875            1880            1885

Tyr Gly Asp Tyr Val Thr Leu Lys Cys Glu Asp Gly Tyr Thr Leu Glu
            1890            1895            1900

Gly Ser Pro Trp Ser Gln Cys Gln Ala Asp Asp Arg Trp Asp Pro Pro
1905            1910            1915            1920

Leu Ala Lys Cys Thr Ser Arg Ala His Asp Ala Leu Ile Val Gly Thr
            1925            1930            1935

Leu Ser Gly Thr Ile Phe Phe Ile Leu Leu Ile Phe Leu Ser Trp
            1940            1945            1950

Ile Ile Leu Lys His Arg Lys Gly Asn Asn Ala His Glu Asn Pro Lys
            1955            1960            1965

Glu Val Ala Ile His Leu His Ser Gln Gly Gly Ser Ser Val His Pro
        1970            1975            1980

Arg Thr Leu Gln Thr Asn Glu Glu Asn Ser Arg Val Leu Pro
1985            1990            1995

(2) INFORMATION FOR SEQ ID NO:14:

(i) SEQUENCE CHARACTERISTICS:
        (A) LENGTH: 3036 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..3036

(xi) SEQUENCE DESCRIPTION: SEQ ID NO:14:

ATT TCT TGT GGC TCT CCT CCG CCT ATC CTA AAT GGC CGG ATT AGT TAT        48
Ile Ser Cys Gly Ser Pro Pro Pro Ile Leu Asn Gly Arg Ile Ser Tyr
 1               5                  10                  15

TAT TCT ACC CCC ATT GCT GTT GGT ACC GTG ATA AGG TAC AGT TGT TCA        96
Tyr Ser Thr Pro Ile Ala Val Gly Thr Val Ile Arg Tyr Ser Cys Ser
                20                  25                  30

GGT ACC TTC CGC CTC ATT GGA GAA AAA AGT CTA TTA TGC ATA ACT AAA       144
Gly Thr Phe Arg Leu Ile Gly Glu Lys Ser Leu Leu Cys Ile Thr Lys
            35                  40                  45

GAC AAA GTG GAT GGA ACC TGG GAT AAA CCT GCT CCT AAA TGT GAA TAT       192
Asp Lys Val Asp Gly Thr Trp Asp Lys Pro Ala Pro Lys Cys Glu Tyr
50                  55                  60

TTC AAT AAA TAT TCT TCT TGC CCT GAG CCC ATA GTA CCA GGA GGA TAC       240
Phe Asn Lys Tyr Ser Ser Cys Pro Glu Pro Ile Val Pro Gly Gly Tyr
65                  70                  75                  80

AAA ATT AGA GGC TCT ACA CCC TAC AGA CAT GGT GAT TCT GTG ACA TTT       288
Lys Ile Arg Gly Ser Thr Pro Tyr Arg His Gly Asp Ser Val Thr Phe
                85                  90                  95

GCC TGT AAA ACC AAC TTC TCC ATG AAC GGA AAC AAG TCT GTT TGG TGT       336
Ala Cys Lys Thr Asn Phe Ser Met Asn Gly Asn Lys Ser Val Trp Cys
               100                 105                 110

CAA GCA AAT AAT ATG TGG GGG CCG ACA CGA CTA CCA ACC TGT GTA AGT       384
Gln Ala Asn Asn Met Trp Gly Pro Thr Arg Leu Pro Thr Cys Val Ser
           115                 120                 125
```

-continued

| | | |
|---|---|---|
| GTT TTC CCT CTC GAG TGT CCA GCA CTT CCT ATG ATC CAC AAT GGA CAT<br>Val Phe Pro Leu Glu Cys Pro Ala Leu Pro Met Ile His Asn Gly His<br>130                135               140 | | 432 |
| CAC ACA AGT GAG AAT GTT GGC TCC ATT GCT CCA GGA TTG TCT GTG ACT<br>His Thr Ser Glu Asn Val Gly Ser Ile Ala Pro Gly Leu Ser Val Thr<br>145               150               155              160 | | 480 |
| TAC AGC TGT GAA TCT GGT TAC TTG CTT GTT GGA GAA AAG ATC ATT AAC<br>Tyr Ser Cys Glu Ser Gly Tyr Leu Leu Val Gly Glu Lys Ile Ile Asn<br>             165               170              175 | | 528 |
| TGT TTG TCT TCG GGA AAA TGG AGT GCT GTC CCC CCA ACA TGT GAA GAG<br>Cys Leu Ser Ser Gly Lys Trp Ser Ala Val Pro Pro Thr Cys Glu Glu<br>          180               185              190 | | 576 |
| GCA CGC TGT AAA TCT CTA GGA CGA TTT CCC AAT GGG AAG GTA AAG GAG<br>Ala Arg Cys Lys Ser Leu Gly Arg Phe Pro Asn Gly Lys Val Lys Glu<br>             195               200              205 | | 624 |
| CCT CCA ATT CTC CGG GTT GGT GTA ACT GCA AAC TTT TTC TGT GAT GAA<br>Pro Pro Ile Leu Arg Val Gly Val Thr Ala Asn Phe Phe Cys Asp Glu<br>210              215              220 | | 672 |
| GGG TAT CGA CTG CAA GGC CCA CCT TCT AGT CGG TGT GTA ATT GCT GGA<br>Gly Tyr Arg Leu Gln Gly Pro Pro Ser Ser Arg Cys Val Ile Ala Gly<br>225             230             235            240 | | 720 |
| CAG GGA GTT GCT TGG ACC AAA ATG CCA GTA TGT GAA GAA ATT TTT TGC<br>Gln Gly Val Ala Trp Thr Lys Met Pro Val Cys Glu Glu Ile Phe Cys<br>          245              250             255 | | 768 |
| CCA TCA CCT CCC CCT ATT CTC AAT GGA AGA CAT ATA GGC AAC TCA CTA<br>Pro Ser Pro Pro Pro Ile Leu Asn Gly Arg His Ile Gly Asn Ser Leu<br>            260             265             270 | | 816 |
| GCA AAT GTC TCA TAT GGA AGC ATA GTC ACT TAC ACT TGT GAC CCG GAC<br>Ala Asn Val Ser Tyr Gly Ser Ile Val Thr Tyr Thr Cys Asp Pro Asp<br>         275              280             285 | | 864 |
| CCA GAG GAA GGA GTG AAC TTC ATC CTT ATT GGA GAG AGC ACT CTC CGT<br>Pro Glu Glu Gly Val Asn Phe Ile Leu Ile Gly Glu Ser Thr Leu Arg<br>290            295             300 | | 912 |
| TGT ACA GTT GAT AGT CAG AAG ACT GGG ACC TGG AGT GGC CCT GCC CCA<br>Cys Thr Val Asp Ser Gln Lys Thr Gly Thr Trp Ser Gly Pro Ala Pro<br>305            310             315            320 | | 960 |
| CGC TGT GAA CTT TCT ACT TCT GCG GTT CAG TGT CCA CAT CCC CAG ATC<br>Arg Cys Glu Leu Ser Thr Ser Ala Val Gln Cys Pro His Pro Gln Ile<br>           325             330             335 | | 1008 |
| CTA AGA GGC CGA ATG GTA TCT GGG CAG AAA GAT CGA TAT ACC TAT AAC<br>Leu Arg Gly Arg Met Val Ser Gly Gln Lys Asp Arg Tyr Thr Tyr Asn<br>           340             345             350 | | 1056 |
| GAC ACT GTG ATA TTT GCT TGC ATG TTT GGC TTC ACC TTG AAG GGC AGC<br>Asp Thr Val Ile Phe Ala Cys Met Phe Gly Phe Thr Leu Lys Gly Ser<br>         355              360             365 | | 1104 |
| AAG CAA ATC CGA TGC AAT GCC CAA GGC ACA TGG GAG CCA TCT GCA CCA<br>Lys Gln Ile Arg Cys Asn Ala Gln Gly Thr Trp Glu Pro Ser Ala Pro<br>370            375             380 | | 1152 |
| GTC TGT GAA AAG GAA TGC CAG GCC CCT CCT AAC ATC CTC AAT GGG CAA<br>Val Cys Glu Lys Glu Cys Gln Ala Pro Pro Asn Ile Leu Asn Gly Gln<br>385            390             395            400 | | 1200 |
| AAG GAA GAT AGA CAC ATG GTC CGC TTT GAC CCT GGA ACA TCT ATA AAA<br>Lys Glu Asp Arg His Met Val Arg Phe Asp Pro Gly Thr Ser Ile Lys<br>           405             410             415 | | 1248 |
| TAT AGC TGT AAC CCT GGC TAT GTG CTG GTG GGA GAA GAA TCC ATA CAG<br>Tyr Ser Cys Asn Pro Gly Tyr Val Leu Val Gly Glu Glu Ser Ile Gln<br>         420              425             430 | | 1296 |
| TGT ACC TCT GAG GTG TGG ACA CCC CCT GTA CCC CAA TGC AAA GTG GCA<br>Cys Thr Ser Glu Val Trp Thr Pro Pro Val Pro Gln Cys Lys Val Ala<br>         435              440             445 | | 1344 |

```
GCG TGT GAA GCT ACA GGA AGG CAA CTC TTG ACA AAA CCC CAG CAC CAA    1392
Ala Cys Glu Ala Thr Gly Arg Gln Leu Leu Thr Lys Pro Gln His Gln
    450                 455                 460

TTT GTT AGA CCA GAT GTC AAC TCT TCT TGT GGT GAA GGG TAC AAG TTA    1440
Phe Val Arg Pro Asp Val Asn Ser Ser Cys Gly Glu Gly Tyr Lys Leu
465                 470                 475                 480

AGT GGG AGT GTT TAT CAG GAG TGT CAA GGC ACA ATT CCT TGG TTT ATG    1488
Ser Gly Ser Val Tyr Gln Glu Cys Gln Gly Thr Ile Pro Trp Phe Met
                485                 490                 495

GAG ATT CGT CTT TGT AAA GAA ATC ACC TGC CCA CCA CCC CCT GTT ATC    1536
Glu Ile Arg Leu Cys Lys Glu Ile Thr Cys Pro Pro Pro Pro Val Ile
            500                 505                 510

TAC AAT GGG GCA CAC ACC GGG AGT TCC TTA GAA GAT TTT CCA TAT GGA    1584
Tyr Asn Gly Ala His Thr Gly Ser Ser Leu Glu Asp Phe Pro Tyr Gly
        515                 520                 525

ACC ACG GTC ACT TAC ACA TGT AAC CCT GGG CCA GAA AGA GGA GTG GAA    1632
Thr Thr Val Thr Tyr Thr Cys Asn Pro Gly Pro Glu Arg Gly Val Glu
    530                 535                 540

TTC AGC CTC ATT GGA GAG AGC ACC ATC CGT TGT ACA AGC AAT GAT CAA    1680
Phe Ser Leu Ile Gly Glu Ser Thr Ile Arg Cys Thr Ser Asn Asp Gln
545                 550                 555                 560

GAA AGA GGC ACC TGG AGT GGC CCT GCT CCC CTG TGT AAA CTT TCC CTC    1728
Glu Arg Gly Thr Trp Ser Gly Pro Ala Pro Leu Cys Lys Leu Ser Leu
                565                 570                 575

CTT GCT GTC CAG TGC TCA CAT GTC CAT ATT GCA AAT GGA TAC AAG ATA    1776
Leu Ala Val Gln Cys Ser His Val His Ile Ala Asn Gly Tyr Lys Ile
            580                 585                 590

TCT GGC AAG GAA GCC CCA TAT TTC TAC AAT GAC ACT GTG ACA TTC AAG    1824
Ser Gly Lys Glu Ala Pro Tyr Phe Tyr Asn Asp Thr Val Thr Phe Lys
        595                 600                 605

TGT TAT AGT GGA TTT ACT TTG AAG GGC AGT AGT CAG ATT CGT TGC AAA    1872
Cys Tyr Ser Gly Phe Thr Leu Lys Gly Ser Ser Gln Ile Arg Cys Lys
    610                 615                 620

GCT GAT AAC ACC TGG GAT CCT GAA ATA CCA GTT TGT GAA AAA GAA ACA    1920
Ala Asp Asn Thr Trp Asp Pro Glu Ile Pro Val Cys Glu Lys Glu Thr
625                 630                 635                 640

TGC CAG CAT GTG AGA CAG AGT CTT CAA GAA CTT CCA GCT GGT TCA CGT    1968
Cys Gln His Val Arg Gln Ser Leu Gln Glu Leu Pro Ala Gly Ser Arg
                645                 650                 655

GTG GAG CTA GTT AAT ACG TCC TGC CAA GAT GGG TAC CAG TTG ACT GGA    2016
Val Glu Leu Val Asn Thr Ser Cys Gln Asp Gly Tyr Gln Leu Thr Gly
            660                 665                 670

CAT GCT TAT CAG ATG TGT CAA GAT GCT GAA AAT GGA ATT TGG TTC AAA    2064
His Ala Tyr Gln Met Cys Gln Asp Ala Glu Asn Gly Ile Trp Phe Lys
        675                 680                 685

AAG ATT CCA CTT TGT AAA GTT ATT CAC TGT CAC CCT CCA CCA GTG ATT    2112
Lys Ile Pro Leu Cys Lys Val Ile His Cys His Pro Pro Pro Val Ile
    690                 695                 700

GTC AAT GGG AAG CAC ACA GGC ATG ATG GCA GAA AAC TTT CTA TAT GGA    2160
Val Asn Gly Lys His Thr Gly Met Met Ala Glu Asn Phe Leu Tyr Gly
705                 710                 715                 720

AAT GAA GTC TCT TAT GAA TGT GAC CAA GGA TTC TAT CTC CTG GGA GAG    2208
Asn Glu Val Ser Tyr Glu Cys Asp Gln Gly Phe Tyr Leu Leu Gly Glu
                725                 730                 735

AAA AAA TTG CAG TGC AGA AGT GAT TCT AAA GGA CAT GGA TCT TGG AGC    2256
Lys Lys Leu Gln Cys Arg Ser Asp Ser Lys Gly His Gly Ser Trp Ser
            740                 745                 750

GGG CCT TCC CCA CAG TGC TTA CGA TCT CCT CCT GTG ACT CGC TGC CCT    2304
Gly Pro Ser Pro Gln Cys Leu Arg Ser Pro Pro Val Thr Arg Cys Pro
```

```
                755            760            765
AAT CCA GAA GTC AAA CAT GGG TAC AAG CTC AAT AAA ACA CAT TCT GCA      2352
Asn Pro Glu Val Lys His Gly Tyr Lys Leu Asn Lys Thr His Ser Ala
        770                775                780

TAT TCC CAC AAT GAC ATA GTG TAT GTT GAC TGC AAT CCT GGC TTC ATC      2400
Tyr Ser His Asn Asp Ile Val Tyr Val Asp Cys Asn Pro Gly Phe Ile
785                790                795                800

ATG AAT GGT AGT CGC GTG ATT AGG TGT CAT ACT GAT AAC ACA TGG GTG      2448
Met Asn Gly Ser Arg Val Ile Arg Cys His Thr Asp Asn Thr Trp Val
            805                810                815

CCA GGT GTG CCA ACT TGT ATC AAA AAA GCC TTC ATA GGG TGT CCA CCT      2496
Pro Gly Val Pro Thr Cys Ile Lys Lys Ala Phe Ile Gly Cys Pro Pro
                820                825                830

CCG CCT AAG ACC CCT AAC GGG AAC CAT ACT GGT GGA AAC ATA GCT CGA      2544
Pro Pro Lys Thr Pro Asn Gly Asn His Thr Gly Gly Asn Ile Ala Arg
                    835                840                845

TTT TCT CCT GGA ATG TCA ATC CTG TAC AGC TGT GAC CAA GGC TAC CTG      2592
Phe Ser Pro Gly Met Ser Ile Leu Tyr Ser Cys Asp Gln Gly Tyr Leu
        850                855                860

CTG GTG GGA GAG GCA CTC CTT CTT TGC ACA CAT GAG GGA ACC TGG AGC      2640
Leu Val Gly Glu Ala Leu Leu Leu Cys Thr His Glu Gly Thr Trp Ser
865                870                875                880

CAA CCT GCC CCT CAT TGT AAA GAG GTA AAC TGT AGC TCA CCA GCA GAT      2688
Gln Pro Ala Pro His Cys Lys Glu Val Asn Cys Ser Ser Pro Ala Asp
            885                890                895

ATG GAT GGA ATC CAG AAA GGG CTG GAA CCA AGG AAA ATG TAT CAG TAT      2736
Met Asp Gly Ile Gln Lys Gly Leu Glu Pro Arg Lys Met Tyr Gln Tyr
                900                905                910

GGA GCT GTT GTA ACT CTG GAG TGT GAA GAT GGG TAT ATG CTG GAA GGC      2784
Gly Ala Val Val Thr Leu Glu Cys Glu Asp Gly Tyr Met Leu Glu Gly
                    915                920                925

AGT CCC CAG AGC CAG TGC CAA TCG GAT CAC CAA TGG AAC CCT CCC CTG      2832
Ser Pro Gln Ser Gln Cys Gln Ser Asp His Gln Trp Asn Pro Pro Leu
        930                935                940

GCG GTT TGC AGA TCC CGT TCA CTT GCT CCT GTC CTT TGT GGT ATT GCT      2880
Ala Val Cys Arg Ser Arg Ser Leu Ala Pro Val Leu Cys Gly Ile Ala
945                950                955                960

GCA GGT TTG ATA CTT CTT ACC TTC TTG ATT GTC GTT ACC TTA TAC GTG      2928
Ala Gly Leu Ile Leu Leu Thr Phe Leu Ile Val Val Thr Leu Tyr Val
            965                970                975

ATA TCA AAA CAC AGA GCA CGC AAT TAT TAT ACA GAT ACA AGC CAG AAA      2976
Ile Ser Lys His Arg Ala Arg Asn Tyr Tyr Thr Asp Thr Ser Gln Lys
                980                985                990

GAA GCT TTT CAT TTA GAA GCA CGA GAA GTA TAT TCT GTT GAT CCA TAC      3024
Glu Ala Phe His Leu Glu Ala Arg Glu Val Tyr Ser Val Asp Pro Tyr
                    995                1000               1005

AAC CCA GCC AGC                                                      3036
Asn Pro Ala Ser
    1010
```

(2) INFORMATION FOR SEQ ID NO:15:

(i) SEQUENCE CHARACTERISTICS:
        (A) LENGTH: 1012 amino acids
        (B) TYPE: amino acid
        (D) TOPOLOGY: linear (ii) MOLECULE TYPE: protein (xi) SEQUENCE DESCRIPTION: SEQ ID NO:15:

Ile Ser Cys Gly Ser Pro Pro Ile Leu Asn Gly Arg Ile Ser Tyr

-continued

```
              1               5              10              15
         Tyr Ser Thr Pro Ile Ala Val Gly Thr Val Ile Arg Tyr Ser Cys Ser
                         20                      25                      30
         Gly Thr Phe Arg Leu Ile Gly Glu Lys Ser Leu Leu Cys Ile Thr Lys
                         35                      40                      45
         Asp Lys Val Asp Gly Thr Trp Asp Lys Pro Ala Pro Lys Cys Glu Tyr
                         50                      55                      60
         Phe Asn Lys Tyr Ser Ser Cys Pro Glu Pro Ile Val Pro Gly Gly Tyr
         65                      70                      75                      80
         Lys Ile Arg Gly Ser Thr Pro Tyr Arg His Gly Asp Ser Val Thr Phe
                         85                      90                      95
         Ala Cys Lys Thr Asn Phe Ser Met Asn Gly Asn Lys Ser Val Trp Cys
                         100                     105                     110
         Gln Ala Asn Asn Met Trp Gly Pro Thr Arg Leu Pro Thr Cys Val Ser
                         115                     120                     125
         Val Phe Pro Leu Glu Cys Pro Ala Leu Pro Met Ile His Asn Gly His
                         130                     135                     140
         His Thr Ser Glu Asn Val Gly Ser Ile Ala Pro Gly Leu Ser Val Thr
         145                     150                     155                     160
         Tyr Ser Cys Glu Ser Gly Tyr Leu Leu Val Gly Glu Lys Ile Ile Asn
                         165                     170                     175
         Cys Leu Ser Ser Gly Lys Trp Ser Ala Val Pro Pro Thr Cys Glu Glu
                         180                     185                     190
         Ala Arg Cys Lys Ser Leu Gly Arg Phe Pro Asn Gly Lys Val Lys Glu
                         195                     200                     205
         Pro Pro Ile Leu Arg Val Gly Val Thr Ala Asn Phe Phe Cys Asp Glu
                         210                     215                     220
         Gly Tyr Arg Leu Gln Gly Pro Pro Ser Ser Arg Cys Val Ile Ala Gly
         225                     230                     235                     240
         Gln Gly Val Ala Trp Thr Lys Met Pro Val Cys Glu Glu Ile Phe Cys
                         245                     250                     255
         Pro Ser Pro Pro Pro Ile Leu Asn Gly Arg His Ile Gly Asn Ser Leu
                         260                     265                     270
         Ala Asn Val Ser Tyr Gly Ser Ile Val Thr Tyr Thr Cys Asp Pro Asp
                         275                     280                     285
         Pro Glu Glu Gly Val Asn Phe Ile Leu Ile Gly Glu Ser Thr Leu Arg
                         290                     295                     300
         Cys Thr Val Asp Ser Gln Lys Thr Gly Thr Trp Ser Gly Pro Ala Pro
         305                     310                     315                     320
         Arg Cys Glu Leu Ser Thr Ser Ala Val Gln Cys Pro His Pro Gln Ile
                         325                     330                     335
         Leu Arg Gly Arg Met Val Ser Gly Gln Lys Asp Arg Tyr Thr Tyr Asn
                         340                     345                     350
         Asp Thr Val Ile Phe Ala Cys Met Phe Gly Phe Thr Leu Lys Gly Ser
                         355                     360                     365
         Lys Gln Ile Arg Cys Asn Ala Gln Gly Thr Trp Glu Pro Ser Ala Pro
                         370                     375                     380
         Val Cys Glu Lys Glu Cys Gln Ala Pro Pro Asn Ile Leu Asn Gly Gln
         385                     390                     395                     400
         Lys Glu Asp Arg His Met Val Arg Phe Asp Pro Gly Thr Ser Ile Lys
                         405                     410                     415
         Tyr Ser Cys Asn Pro Gly Tyr Val Leu Val Gly Glu Glu Ser Ile Gln
                         420                     425                     430
```

-continued

```
Cys Thr Ser Glu Val Trp Thr Pro Pro Val Pro Gln Cys Lys Val Ala
        435                 440                 445
Ala Cys Glu Ala Thr Gly Arg Gln Leu Leu Thr Lys Pro Gln His Gln
450                 455                 460
Phe Val Arg Pro Asp Val Asn Ser Ser Cys Gly Glu Gly Tyr Lys Leu
465                 470                 475                 480
Ser Gly Ser Val Tyr Gln Glu Cys Gln Gly Thr Ile Pro Trp Phe Met
                485                 490                 495
Glu Ile Arg Leu Cys Lys Glu Ile Thr Cys Pro Pro Pro Val Ile
            500                 505                 510
Tyr Asn Gly Ala His Thr Gly Ser Ser Leu Glu Asp Phe Pro Tyr Gly
            515                 520                 525
Thr Thr Val Thr Tyr Thr Cys Asn Pro Gly Pro Glu Arg Gly Val Glu
        530                 535                 540
Phe Ser Leu Ile Gly Glu Ser Thr Ile Arg Cys Thr Ser Asn Asp Gln
545                 550                 555                 560
Glu Arg Gly Thr Trp Ser Gly Pro Ala Pro Leu Cys Lys Leu Ser Leu
                565                 570                 575
Leu Ala Val Gln Cys Ser His Val His Ile Ala Asn Gly Tyr Lys Ile
            580                 585                 590
Ser Gly Lys Glu Ala Pro Tyr Phe Tyr Asn Asp Thr Val Thr Phe Lys
        595                 600                 605
Cys Tyr Ser Gly Phe Thr Leu Lys Gly Ser Ser Gln Ile Arg Cys Lys
        610                 615                 620
Ala Asp Asn Thr Trp Asp Pro Glu Ile Pro Val Cys Glu Lys Glu Thr
625                 630                 635                 640
Cys Gln His Val Arg Gln Ser Leu Gln Glu Leu Pro Ala Gly Ser Arg
                645                 650                 655
Val Glu Leu Val Asn Thr Ser Cys Gln Asp Gly Tyr Gln Leu Thr Gly
            660                 665                 670
His Ala Tyr Gln Met Cys Gln Asp Ala Glu Asn Gly Ile Trp Phe Lys
        675                 680                 685
Lys Ile Pro Leu Cys Lys Val Ile His Cys His Pro Pro Pro Val Ile
        690                 695                 700
Val Asn Gly Lys His Thr Gly Met Met Ala Glu Asn Phe Leu Tyr Gly
705                 710                 715                 720
Asn Glu Val Ser Tyr Glu Cys Asp Gln Gly Phe Tyr Leu Leu Gly Glu
                725                 730                 735
Lys Lys Leu Gln Cys Arg Ser Asp Ser Lys Gly His Gly Ser Trp Ser
            740                 745                 750
Gly Pro Ser Pro Gln Cys Leu Arg Ser Pro Val Thr Arg Cys Pro
        755                 760                 765
Asn Pro Glu Val Lys His Gly Tyr Lys Leu Asn Lys Thr His Ser Ala
        770                 775                 780
Tyr Ser His Asn Asp Ile Val Tyr Val Asp Cys Asn Pro Gly Phe Ile
785                 790                 795                 800
Met Asn Gly Ser Arg Val Ile Arg Cys His Thr Asp Asn Thr Trp Val
                805                 810                 815
Pro Gly Val Pro Thr Cys Ile Lys Lys Ala Phe Ile Gly Cys Pro Pro
            820                 825                 830
Pro Pro Lys Thr Pro Asn Gly Asn His Thr Gly Gly Asn Ile Ala Arg
        835                 840                 845
```

```
Phe Ser Pro Gly Met Ser Ile Leu Tyr Ser Cys Asp Gln Gly Tyr Leu
    850                 855                 860

Leu Val Gly Glu Ala Leu Leu Cys Thr His Glu Gly Thr Trp Ser
865                 870                 875                 880

Gln Pro Ala Pro His Cys Lys Glu Val Asn Cys Ser Ser Pro Ala Asp
                    885                 890                 895

Met Asp Gly Ile Gln Lys Gly Leu Glu Pro Arg Lys Met Tyr Gln Tyr
                900                 905                 910

Gly Ala Val Val Thr Leu Glu Cys Glu Asp Gly Tyr Met Leu Glu Gly
                915                 920                 925

Ser Pro Gln Ser Gln Cys Gln Ser Asp His Gln Trp Asn Pro Pro Leu
    930                 935                 940

Ala Val Cys Arg Ser Arg Ser Leu Ala Pro Val Leu Cys Gly Ile Ala
945                 950                 955                 960

Ala Gly Leu Ile Leu Leu Thr Phe Leu Ile Val Thr Leu Tyr Val
                965                 970                 975

Ile Ser Lys His Arg Ala Arg Asn Tyr Tyr Thr Asp Thr Ser Gln Lys
                980                 985                 990

Glu Ala Phe His Leu Glu Ala Arg Glu Val Tyr Ser Val Asp Pro Tyr
                995                 1000                1005

Asn Pro Ala Ser
    1010
```

(2) INFORMATION FOR SEQ ID NO:16:

(i) SEQUENCE CHARACTERISTICS:
        (A) LENGTH: 1930 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..1041

(xi) SEQUENCE DESCRIPTION: SEQ ID NO:16:

```
GAC TGT GGC CTT CCC CCA GAT GTA CCT AAT GCC CAG CCA GCT TTG GAA     48
Asp Cys Gly Leu Pro Pro Asp Val Pro Asn Ala Gln Pro Ala Leu Glu
  1               5                  10                  15

GGC CGT ACA AGT TTT CCC GAG GAT ACT GTA ATA ACG TAC AAA TGT GAA     96
Gly Arg Thr Ser Phe Pro Glu Asp Thr Val Ile Thr Tyr Lys Cys Glu
                 20                  25                  30

GAA AGC TTT GTG AAA ATT CCT GGC GAG AAG GAC TCA GTG ACC TGC CTT    144
Glu Ser Phe Val Lys Ile Pro Gly Glu Lys Asp Ser Val Thr Cys Leu
         35                  40                  45

AAG GGC ATG CAA TGG TCA GAT ATT GAA GAG TTC TGC AAT CGT AGC TGC    192
Lys Gly Met Gln Trp Ser Asp Ile Glu Glu Phe Cys Asn Arg Ser Cys
     50                  55                  60

GAG GTG CCA ACA AGG CTA AAT TCT GCA TCC CTC AAA CAG CCT TAT ATC    240
Glu Val Pro Thr Arg Leu Asn Ser Ala Ser Leu Lys Gln Pro Tyr Ile
 65                  70                  75                  80

ACT CAG AAT TAT TTT CCA GTC GGT ACT GTT GTG GAA TAT GAG TGC CGT    288
Thr Gln Asn Tyr Phe Pro Val Gly Thr Val Val Glu Tyr Glu Cys Arg
                 85                  90                  95

CCA GGT TAC AGA AGA GAA CCT TCT CTA TCA CCA AAA CTA ACT TGC CTT    336
Pro Gly Tyr Arg Arg Glu Pro Ser Leu Ser Pro Lys Leu Thr Cys Leu
                100                 105                 110

CAG AAT TTA AAA TGG TCC ACA GCA GTC GAA TTT TGT AAA AAG AAA TCA    384
```

```
        Gln Asn Leu Lys Trp Ser Thr Ala Val Glu Phe Cys Lys Lys Ser
                    115                 120                 125

TGC CCT AAT CCG GGA GAA ATA CGA AAT GGT CAG ATT GAT GTA CCA GGT        432
Cys Pro Asn Pro Gly Glu Ile Arg Asn Gly Gln Ile Asp Val Pro Gly
    130                 135                 140

GGC ATA TTA TTT GGT GCA ACC ATC TCC TTC TCA TGT AAC ACA GGG TAC        480
Gly Ile Leu Phe Gly Ala Thr Ile Ser Phe Ser Cys Asn Thr Gly Tyr
145                 150                 155                 160

AAA TTA TTT GGC TCG ACT TCT AGT TTT TGT CTT ATT TCA GGC AGC TCT        528
Lys Leu Phe Gly Ser Thr Ser Ser Phe Cys Leu Ile Ser Gly Ser Ser
                165                 170                 175

GTC CAG TGG AGT GAC CCG TTG CCA GAG TGC AGA GAA ATT TAT TGT CCA        576
Val Gln Trp Ser Asp Pro Leu Pro Glu Cys Arg Glu Ile Tyr Cys Pro
            180                 185                 190

GCA CCA CCA CAA ATT GAC AAT GGA ATA ATT CAA GGG GAA CGT GAC CAT        624
Ala Pro Pro Gln Ile Asp Asn Gly Ile Ile Gln Gly Glu Arg Asp His
        195                 200                 205

TAT GGA TAT AGA CAG TCT GTA ACG TAT GCA TGT AAT AAA GGA TTC ACC        672
Tyr Gly Tyr Arg Gln Ser Val Thr Tyr Ala Cys Asn Lys Gly Phe Thr
    210                 215                 220

ATG ATT GGA GAG CAC TCT ATT TAT TGT ACT GTG AAT AAT GAT GAA GGA        720
Met Ile Gly Glu His Ser Ile Tyr Cys Thr Val Asn Asn Asp Glu Gly
225                 230                 235                 240

GAG TGG AGT GGC CCA CCA CCT GAA TGC AGA GGA AAA TCT CTA ACT TCC        768
Glu Trp Ser Gly Pro Pro Pro Glu Cys Arg Gly Lys Ser Leu Thr Ser
                245                 250                 255

AAG GTC CCA CCA ACA GTT CAG AAA CCT ACC ACA GTA AAT GTT CCA ACT        816
Lys Val Pro Pro Thr Val Gln Lys Pro Thr Thr Val Asn Val Pro Thr
            260                 265                 270

ACA GAA GTC TCA CCA ACT TCT CAG AAA ACC ACC ACA AAA ACC ACC ACA        864
Thr Glu Val Ser Pro Thr Ser Gln Lys Thr Thr Thr Lys Thr Thr Thr
        275                 280                 285

CCA AAT GCT CAA GCA ACA CGG AGT ACA CCT GTT TCC AGG ACA ACC AAG        912
Pro Asn Ala Gln Ala Thr Arg Ser Thr Pro Val Ser Arg Thr Thr Lys
    290                 295                 300

CAT TTT CAT GAA ACA ACC CCA AAT AAA GGA AGT GGA ACC ACT TCA GGT        960
His Phe His Glu Thr Thr Pro Asn Lys Gly Ser Gly Thr Thr Ser Gly
305                 310                 315                 320

ACT ACC CGT CTT CTA TCT GGG CAC ACG TGT TTC ACG TTG ACA GGT TTG       1008
Thr Thr Arg Leu Leu Ser Gly His Thr Cys Phe Thr Leu Thr Gly Leu
                325                 330                 335

CTT GGG ACG CTA GTA ACC ATG GGC TTG CTG ACT TAGCCAAAGA AGAGTTAAGA     1061
Leu Gly Thr Leu Val Thr Met Gly Leu Leu Thr
            340                 345

AGAAAATACA CACAAGTATA CAGACTGTTC CTAGTTTCTT AGACTTATCT GCATATTGGA    1121

TAAAATAAAT GCAATTGTGC TCTTCATTTA GGATGCTTTC ATTGTCTTTA AGATGTGTTA    1181

GGAATGTCAA CAGAGCAAGG AGAAAAAAGG CAGTCCTGGA ATCACATTCT AGCACACCT     1241

GCGCCTCTTG AAAATAGAAC AACTTGCAGA ATTGAGAGTG ATTCCTTTCC TAAAAGTGTA    1301

AGAAAGCATA GAGATTTGTT CGTATTAAGA ATGGGATCAC GAGGAAAAGA GAAGGAAAGT    1361

GATTTTTTTC CACAAGATCT GAAATGATAT TTCCACTTAT AAAGGAAATA AAAAATGAAA    1421

AACATTATTT GGATATCAAA AGCAAATAAA AACCCAATTC AGTCTCTTCT AAGCAAAATT    1481

GCTAAAGAGA GATGACCACA TTATAAAGTA ATCTTTGGCT AAGGCATTTT CATCTTTCCT    1541

TCGGTTGGCA AAATATTTTA AAGGTAAAAC ATGCTGGTGA ACCAGGGTGT TGATGGTGAT    1601

AAGGGAGGAA TATAGAATGA AAGACTGAAT CTTCCTTTGT TGCACAAATA GAGTTTGGAA    1661
```

-continued

```
AAAGCCTGTG AAAGGTGTCT TCTTTGACTT AATGTCTTTA AAAGTATCCA GAGATACTAC    1721

AATATTAACA TAAGAAAAGA TTATATATTA TTTCTGAATC GAGATGTCCA TAGTCAAATT    1781

TGTAAATCTT ATTCTTTTGT AATATTTATT TATATTTATT TATGACAGTG AACATTCTGA    1841

TTTTACATGT AAAACAAGAA AAGTTGAAGA AGATATGTGA AGAAAAATGT ATTTTTCCTA    1901

AATAGAAATA AATGATCCCA TTTTTTGGT                                      1930
```

(2) INFORMATION FOR SEQ ID NO:17:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Cys Gly Leu Pro Pro Asp Val Pro Asn Ala Gln Pro Ala Leu Glu
 1               5                  10                  15

Gly Arg Thr Ser Phe Pro Glu Asp Thr Val Ile Thr Tyr Lys Cys Glu
            20                  25                  30

Glu Ser Phe Val Lys Ile Pro Gly Glu Lys Asp Ser Val Thr Cys Leu
        35                  40                  45

Lys Gly Met Gln Trp Ser Asp Ile Glu Glu Phe Cys Asn Arg Ser Cys
    50                  55                  60

Glu Val Pro Thr Arg Leu Asn Ser Ala Ser Leu Lys Gln Pro Tyr Ile
65                  70                  75                  80

Thr Gln Asn Tyr Phe Pro Val Gly Thr Val Val Glu Tyr Glu Cys Arg
                85                  90                  95

Pro Gly Tyr Arg Arg Glu Pro Ser Leu Ser Pro Lys Leu Thr Cys Leu
            100                 105                 110

Gln Asn Leu Lys Trp Ser Thr Ala Val Glu Phe Cys Lys Lys Lys Ser
        115                 120                 125

Cys Pro Asn Pro Gly Glu Ile Arg Asn Gly Gln Ile Asp Val Pro Gly
    130                 135                 140

Gly Ile Leu Phe Gly Ala Thr Ile Ser Phe Ser Cys Asn Thr Gly Tyr
145                 150                 155                 160

Lys Leu Phe Gly Ser Thr Ser Ser Phe Cys Leu Ile Ser Gly Ser Ser
                165                 170                 175

Val Gln Trp Ser Asp Pro Leu Pro Glu Cys Arg Glu Ile Tyr Cys Pro
            180                 185                 190

Ala Pro Pro Gln Ile Asp Asn Gly Ile Ile Gln Gly Glu Arg Asp His
        195                 200                 205

Tyr Gly Tyr Arg Gln Ser Val Thr Tyr Ala Cys Asn Lys Gly Phe Thr
    210                 215                 220

Met Ile Gly Glu His Ser Ile Tyr Cys Thr Val Asn Asn Asp Glu Gly
225                 230                 235                 240

Glu Trp Ser Gly Pro Pro Glu Cys Arg Gly Lys Ser Leu Thr Ser
                245                 250                 255

Lys Val Pro Pro Thr Val Gln Lys Pro Thr Thr Val Asn Val Pro Thr
            260                 265                 270

Thr Glu Val Ser Pro Thr Ser Gln Lys Thr Thr Thr Lys Thr Thr Thr
        275                 280                 285

Pro Asn Ala Gln Ala Thr Arg Ser Thr Pro Val Ser Arg Thr Thr Lys
    290                 295                 300
```

```
His Phe His Glu Thr Thr Pro Asn Lys Gly Ser Gly Thr Thr Ser Gly
305                 310                 315                 320

Thr Thr Arg Leu Leu Ser Gly His Thr Cys Phe Thr Leu Thr Gly Leu
            325                 330                 335

Leu Gly Thr Leu Val Thr Met Gly Leu Leu Thr
            340                 345
```

(2) INFORMATION FOR SEQ ID NO:18:

(i) SEQUENCE CHARACTERISTICS:
        (A) LENGTH: 1050 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..1050

(xi) SEQUENCE DESCRIPTION: SEQ ID NO:18:

```
TGT GAG GAG CCA CCA ACA TTT GAA GCT ATG GAG CTC ATT GGT AAA CCA         48
Cys Glu Glu Pro Pro Thr Phe Glu Ala Met Glu Leu Ile Gly Lys Pro
 1               5                  10                  15

AAA CCC TAC TAT GAG ATT GGT GAA CGA GTA GAT TAT AAG TGT AAA AAA         96
Lys Pro Tyr Tyr Glu Ile Gly Glu Arg Val Asp Tyr Lys Cys Lys Lys
             20                  25                  30

GGA TAC TTC TAT ATA CCT CCT CTT GCC ACC CAT ACT ATT TGT GAT CGG        144
Gly Tyr Phe Tyr Ile Pro Pro Leu Ala Thr His Thr Ile Cys Asp Arg
         35                  40                  45

AAT CAT ACA TGG CTA CCT GTC TCA GAT GAC GCC TGT TAT AGA GAA ACA        192
Asn His Thr Trp Leu Pro Val Ser Asp Asp Ala Cys Tyr Arg Glu Thr
     50                  55                  60

TGT CCA TAT ATA CGG GAT CCT TTA AAT GGC CAA GCA GTC CCT GCA AAT        240
Cys Pro Tyr Ile Arg Asp Pro Leu Asn Gly Gln Ala Val Pro Ala Asn
 65                  70                  75                  80

GGG ACT TAC GAG TTT GGT TAT CAG ATG CAC TTT ATT TGT AAT GAG GGT        288
Gly Thr Tyr Glu Phe Gly Tyr Gln Met His Phe Ile Cys Asn Glu Gly
                 85                  90                  95

TAT TAC TTA ATT GGT GAA GAA ATT CTA TAT TGT GAA CTT AAA GGA TCA        336
Tyr Tyr Leu Ile Gly Glu Glu Ile Leu Tyr Cys Glu Leu Lys Gly Ser
            100                 105                 110

GTA GCA ATT TGG AGC GGT AAG CCC CCA ATA TGT GAA AAG GTT TTG TGT        384
Val Ala Ile Trp Ser Gly Lys Pro Pro Ile Cys Glu Lys Val Leu Cys
        115                 120                 125

ACA CCA CCT CCA AAA ATA AAA AAT GGA AAA CAC ACC TTT AGT GAA GTA        432
Thr Pro Pro Pro Lys Ile Lys Asn Gly Lys His Thr Phe Ser Glu Val
130                 135                 140

GAA GTA TTT GAG TAT CTT GAT GCA GTA ACT TAT AGT TGT GAT CCT GCA        480
Glu Val Phe Glu Tyr Leu Asp Ala Val Thr Tyr Ser Cys Asp Pro Ala
145                 150                 155                 160

CCT GGA CCA GAT CCA TTT TCA CTT ATT GGA GAG AGC ACG ATT TAT TGT        528
Pro Gly Pro Asp Pro Phe Ser Leu Ile Gly Glu Ser Thr Ile Tyr Cys
                165                 170                 175

GGT GAC AAT TCA GTG TGG AGT CGT GCT GCT CCA GAG TGT AAA GTG GTC        576
Gly Asp Asn Ser Val Trp Ser Arg Ala Ala Pro Glu Cys Lys Val Val
            180                 185                 190

AAA TGT CGA TTT CCA GTA GTC GAA AAT GGA AAA CAG ATA TCA GGA TTT        624
Lys Cys Arg Phe Pro Val Val Glu Asn Gly Lys Gln Ile Ser Gly Phe
        195                 200                 205

GGA AAA AAA TTT TAC TAC AAA GCA ACA GTT ATG TTT GAA TGC GAT AAG        672
```

-continued

```
            Gly Lys Lys Phe Tyr Tyr Lys Ala Thr Val Met Phe Glu Cys Asp Lys
                210                 215                 220

GGT TTT TAC CTC GAT GGC AGC GAC ACA ATT GTC TGT GAC AGT AAC AGT              720
Gly Phe Tyr Leu Asp Gly Ser Asp Thr Ile Val Cys Asp Ser Asn Ser
225                 230                 235                 240

ACT TGG GAT CCC CCA GTT CCA AAG TGT CTT AAA GTG TCG ACT TCT TCC              768
Thr Trp Asp Pro Pro Val Pro Lys Cys Leu Lys Val Ser Thr Ser Ser
                245                 250                 255

ACT ACA AAA TCT CCA GCG TCC AGT GCC TCA GGT CCT AGG CCT ACT TAC              816
Thr Thr Lys Ser Pro Ala Ser Ser Ala Ser Gly Pro Arg Pro Thr Tyr
        260                 265                 270

AAG CCT CCA GTC TCA AAT TAT CCA GGA TAT CCT AAA CCT GAG GAA GGA              864
Lys Pro Pro Val Ser Asn Tyr Pro Gly Tyr Pro Lys Pro Glu Glu Gly
            275                 280                 285

ATA CTT GAC AGT TTG GAT GTT TGG GTC ATT GCT GTG ATT GTT ATT GCC              912
Ile Leu Asp Ser Leu Asp Val Trp Val Ile Ala Val Ile Val Ile Ala
        290                 295                 300

ATA GTT GTT GGA GTT GCA GTA ATT TGT GTT GTC CCG TAC AGA TAT CTT              960
Ile Val Val Gly Val Ala Val Ile Cys Val Val Pro Tyr Arg Tyr Leu
305                 310                 315                 320

CAA AGG AGG AAG AAG AAA GGG AAA GCA GAT GGT GGA GCT GAA TAT GCC             1008
Gln Arg Arg Lys Lys Lys Gly Lys Ala Asp Gly Gly Ala Glu Tyr Ala
                325                 330                 335

ACT TAC CAG ACT AAA TCA ACC ACT CCA GCA GAG CAG AGA GGC                     1050
Thr Tyr Gln Thr Lys Ser Thr Thr Pro Ala Glu Gln Arg Gly
            340                 345                 350
```

(2) INFORMATION FOR SEQ ID NO:19:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO:19:

```
Cys Glu Glu Pro Pro Thr Phe Glu Ala Met Glu Leu Ile Gly Lys Pro
1               5                   10                  15

Lys Pro Tyr Tyr Glu Ile Gly Glu Arg Val Asp Tyr Lys Cys Lys Lys
            20                  25                  30

Gly Tyr Phe Tyr Ile Pro Pro Leu Ala Thr His Thr Ile Cys Asp Arg
        35                  40                  45

Asn His Thr Trp Leu Pro Val Ser Asp Ala Cys Tyr Arg Glu Thr
    50                  55                  60

Cys Pro Tyr Ile Arg Asp Pro Leu Asn Gly Gln Ala Val Pro Ala Asn
65                  70                  75                  80

Gly Thr Tyr Glu Phe Gly Tyr Gln Met His Phe Ile Cys Asn Glu Gly
                85                  90                  95

Tyr Tyr Leu Ile Gly Glu Glu Ile Leu Tyr Cys Glu Leu Lys Gly Ser
            100                 105                 110

Val Ala Ile Trp Ser Gly Lys Pro Pro Ile Cys Glu Lys Val Leu Cys
        115                 120                 125

Thr Pro Pro Pro Lys Ile Lys Asn Gly Lys His Thr Phe Ser Glu Val
    130                 135                 140

Glu Val Phe Glu Tyr Leu Asp Ala Val Thr Tyr Ser Cys Asp Pro Ala
145                 150                 155                 160

Pro Gly Pro Asp Pro Phe Ser Leu Ile Gly Glu Ser Thr Ile Tyr Cys
                165                 170                 175
```

-continued

```
Gly Asp Asn Ser Val Trp Ser Arg Ala Ala Pro Glu Cys Lys Val Val
            180                 185                 190

Lys Cys Arg Phe Pro Val Val Glu Asn Gly Lys Gln Ile Ser Gly Phe
        195             200                 205

Gly Lys Lys Phe Tyr Tyr Lys Ala Thr Val Met Phe Glu Cys Asp Lys
    210             215                 220

Gly Phe Tyr Leu Asp Gly Ser Asp Thr Ile Val Cys Asp Ser Asn Ser
225                 230                 235                 240

Thr Trp Asp Pro Pro Val Pro Lys Cys Leu Lys Val Ser Thr Ser Ser
            245                 250                 255

Thr Thr Lys Ser Pro Ala Ser Ser Ala Ser Gly Pro Arg Pro Thr Tyr
            260             265                 270

Lys Pro Pro Val Ser Asn Tyr Pro Gly Tyr Pro Lys Pro Glu Glu Gly
        275                 280                 285

Ile Leu Asp Ser Leu Asp Val Trp Val Ile Ala Val Ile Val Ile Ala
    290                 295                 300

Ile Val Val Gly Val Ala Val Ile Cys Val Val Pro Tyr Arg Tyr Leu
305             310                 315                 320

Gln Arg Arg Lys Lys Lys Gly Lys Ala Asp Gly Gly Ala Glu Tyr Ala
            325                 330                 335

Thr Tyr Gln Thr Lys Ser Thr Thr Pro Ala Glu Gln Arg Gly
            340                 345                 350
```

MODIFIED RCA PROTEINS

This is a continuation-in-part of U.S. Ser. No. 07/695,514 "Modified Complement System Regulators" filed May 3, 1991, by John P. Atkinson, Dennis Hourcade, and Malgorzata Krych now abandoned.

BACKGROUND OF THE INVENTION

The invention relates to modified and/or shortened forms of complement regulators derived from regulatory proteins of complement activation (RCA), especially CR1.

The complement system serves to aid in the removal of foreign substances and of immune complexes from animal hosts. This system and its regulation is reviewed by Hourcade, D., et al., *Advances in Immunol* (1989) 45:381–416. Briefly, the complement system generates, either by a "classical pathway" or an "alternative pathway," C3b which binds to target immune complexes or foreign substances and marks them for destruction or clearance. C3b is generated from its precursor C3 by the proteolytic enzymes collectively designated "C3 convertase." One form of C3 convertase is generated in the classical pathway by the association of the proteins C4b and C2a. The other form is generated in the alternative pathway by association of C3b and Bb. Both C3 convertases can associate with an additional C3b subunit to form the C5 convertases, C3bBbC3b and C4bC2aC3b, both of which are active in the production of the C5–C9 membrane attack complex which can cause cell lysis, and the production of C5a, a major proinflammatory agent.

Both C3b, and less directly, C4b, are agonists in the complement system. This is shown in the diagram in FIG. 1.

The complement system is regulated via a number of interrelated mechanisms. There are two general mechanisms for inhibition of the destructive components of the complement system. The first mechanism is generally reversible, facilitating the dissociation of the C3 convertases—i.e., C3b from Bb and C4b from C2a. Facilitation of dissociation is sometimes known as decay acceleration. The dissociation may also involve reversible binding of the antagonist proteins to C3b or C4b components, thus preventing their reassociation. The other mechanism, which is an irreversible inactivation process, results from proteolytic cleavage of the C3 convertase components C3b or C4b by the serine protease factor I. This proteolytic cleavage occurs only in the presence of a cofactor. Both general regulatory mechanisms, the facilitation of dissociation of C3b and C4b and the inactivation of C3b and C4b through cleavage by factor I, also apply to the inhibition of the alternative pathway C5 convertase (C3bBbC3b) and the classical pathway C5 convertase (C4bC2aC3b).

The proteins encoded by a region of the genome which is designated the "regulators of complement activation" (RCA) gene cluster are involved in both of the foregoing mechanisms. Currently, it is known that at least six complement proteins are encoded by this region. These are summarized in Table 1.

TABLE 1

RCA Proteins: Functional Profil

| Name | Primary Ligand(s) | Decay Acceleration (Dissociation) | Cofactor Activity |
| --- | --- | --- | --- |
| CR1 | C3b/C4b | + | + |
| MCP | C3b/C4b | − | + |
| DAF | C3b/C4b | + | − |
|  | C3 Convertases |  |  |
| C4bp | C4b | + | + |
| Factor H | C3b | + | + |
| CR2 | C3dg | − | ND |

These proteins share certain structural similarities which are further described below.

The reversible binding to C4b or C3b to dissociate the C3 convertases is effected by two plasma proteins designated C4 binding protein (C4bp) and factor H, and by two membrane proteins designated decay acceleration factor (DAF) and complement receptor 1 (CR1). Reversible binding to C4b is effected by C4bp, DAF and CR1 while reversible binding to C3b is effected by factor H, DAF and CR1.

The irreversible inactivation of the C3 convertases resulting from proteolytic cleavage of convertase components C3b or C4b by the enzyme factor I can occur by virtue of cofactor activity effected by the above-mentioned factor H and C4bp in the plasma and by CR1 and membrane cofactor protein (MCP) at the cell surface. Cofactor activity for cleavage of C3b is effected by factor H, CR1 and MCP while cofactor activity for cleavage of C4b is effected by C4bp, CR1 and MCP. It is also possible that the sixth protein, complement receptor 2 (CR2), has this cofactor activity at the cell surface.

In summary, of the six proteins encoded by the RCA gene cluster, factor H, C4bp, and CR1 have both reversible dissociation activity and irreversible cofactor activity; DAF has only reversible dissociation activity, and MCP and possibly CR2 have only irreversible cofactor activities. CR1, DAF and MCP interact with both C3b and C4b; C4bp interacts primarily with C4b, and factor H interacts primarily with C3b.

The cDNAs corresponding to CR1, CR2, DAF, MCP, C4bp, and factor H have all been obtained and sequenced. Evaluation of these comparative sequences has lead to the alignment set forth in FIG. 2A which shows the organization of the RCA proteins into short consensus repeat ("SCR") containing and non-SCR-containing regions with the N-terminal ends at the left. In this figure, TM refers to transmembrane domain, C to cytoplasmic domain, 0 to 0-linked glycosylation domain, G to glycolipid anchor, U to domain with unknown significance and D to a disulfide bridge-containing domain.

There is considerable uniformity among the RCA family of proteins. All of them are composed of 60–70 amino acid repeating units commonly designated "short consensus repeats" (SCRs). Each SCR shares a number of invariant or highly conserved amino acid residues with other SCRs in the same protein or SCRs in other family members. Those members of the family which are membrane bound also have at their C termini either transmembrane regions and intracellular regions or a glycolipid anchor.

The SCRs form the extracellular portions of those members of the family which are membrane-bound and almost all of the protein structure in the secreted members. Two covalently-crosslinked cysteine pairs establish two loops within each SCR. The smallest family members are DAF and MCP; each contains four SCRs followed by an 0-linked glycosylation region. DAF is terminated with a glycolipid anchor while MCP ends with an extracytoplasmic segment of unknown significance, a transmembrane region and an intracellular domain. Of the secreted members of the family, factor H contains twenty SCRs, while the native form of C4bp is an association of seven subunits of eight SCRs (the C4bp alpha chains) and one subunit of three SCRs (the C4bp beta chain). Both C4bp chains conclude with non-SCR domains that interconnect the chains through disulfide linkages. CR2 contains sixteen SCRs, a transmembrane region and an intracellular domain. The most common polymorphic form of CR1 contains four repeating units of seven similar SCRs (long homologous repeats or LHRS) numbered 1–28, followed by an additional two SCRs designated 29 and 30, a transmembrane region and an intracellular region.

Klickstein, L. B., et al., *J. Exy. Med.* (1988) 168:1699–1717, described the identification of distinct C3b and C4b recognition sites in CR1 using deletion mutagenesis. They concluded that a singled primary C4b binding site is located in SCR 1–2 (Sequence ID Nos. 1 and 3), while two major C3b binding sites are located in SCR 8–9 (Sequence ID Nos. 2 and 4), and SCR 15–16. C3b cofactor activity was localized to SCR 8–9 and SCR 15–16. More recently it has been shown the CR1 active site containing SCR 8–9 extends to SCR 10, and by analogy, the active site that contains SCR 15–16 (which is only one amino acid different than SCR 8–9) must extend to SCR 17. (Kalli, et al., *J. Exp. Med.* 174, 1451–1460 (1991); Makrides, et al., *J. Biol. Chem.* 267, 24754–24761 (1992)). The CR1 active site containing SCR 1–2 extends to SCR 3 and/or 4, as reported by Makrides, et al., (1992).

The murine C4bp binding site, and presumably the C4b cofactor and C4bC2a decay acceleration active sites, was reported to extend from SCRs 1–3 in the alpha chain by Ogata, et al., *J. Immunology* 150, 2273–2280 (1993).

The factor H binding site, and probably the C3b cofactor and C3bBb decay acceleration active sites, lies within the first five SCRs. The CR2 binding site for C3b proteolytic products extends through the first two SCRs, Kalli, et al., *J. Immunology* 147: 509–594 (1991); Carel, et al., *J. Biol. Chem.* 265: 12293–12299 (1990).

The MCP active sites extend through all four SCRs: SCRs 2–4 are required for C3b and C4b cofactor activity. SCR 1 appears unnecessary for C3b cofactor activity and binding but appears necessary for efficient C4b cofactor activity and binding, as reported by Adams, et al., *J. Immunology* 147:3005–3011 (1991). The DAF active sites extend through SCRs 2–4, as reported by Coyne, et al., *J. Immunology* 149: 2906–2913 (1992).

Hourcade, D., et al., *J. Exp. Med.* 168:1255–1270 (1988), described a cDNA clone designated CR1–4 that encodes the first eight and one-half amino terminal SCRs of CR1. This cDNA was transfected into COS cells which resulted in the synthesis of a secreted truncated form of CR1 with a molecular weight of 78 kd (Krych, N. et al., *Proc. Natl. Acad. Sci. USA* 88:4353–4357 (1991). This shortened form of the protein, as shown herein below, binds mainly C4b. This shortened form has now been determined to have C4b cofactor activity, as described herein.

The multiple binding sites of CR1 can cooperate in their interactions with C3b-containing targets. In vitro, CR1 binds C3—C3b dimers much more tightly than C3b monomers because binding to dimers can occur simultaneously at two sites in the same CR1 molecule, as reported by Wong and Farrell, *J. Immunol.* (1991) 146:656; Ross and Medof *Adv. Immunol.* (1985) 37:217). Deletion of one of the two primary C3b binding sites can reduce the binding of CR1 to C3—C3b by a factor of ten, as reported by Wong and Farrell, *J. Immunol.* (1991) 146:656. It is likely that the primary C4b binding site also cooperates with the primary C3b binding sites in interactions with targets that contain both C3b and C4b. These effects have an important consequence in vivo: CR1 has a higher affinity for targets densely coated with C3b and with targets densely coated with C3b plus C4b.

The C5 convertases, which are important in the stimulation of inflammation and in lysis of some target cells, are composed of multiple CR1 ligands: The classical C5 convertase contains C3b and C4b (C4bC3bC2a) while the alternative pathway C5 convertase contains two C3b proteins (C3bC3bBb). Inactivation of the C5 convertases by CR1 can also involve cooperation between more than one CR1 binding site. Wong and Farrell. *J. Immunol.* (1991) 146:656 showed that more than one CR1 C3b binding site may be essential for effective inhibition of alternative pathway C3 and C5 convertases.

The proteins encoded by the RCA gene cluster can be prepared recombinantly and used in diagnosis and therapy for the regulation of the complement system. The problems of transplantation of xenografts are reviewed by Platt, J. L., et al., in *Immunology Today* (1990) 11:450–457. Evidence has accumulated that the immediate hyperacute rejection of discordant xenografts is caused by recipient complement activity. Transgenic animals expressing human complement regulators (such as DAF or MCP) on cell surfaces could be an abundant source of organs that would be protected from hyperacute rejection in human recipients. A soluble complement inhibitor could also play a role in protecting xenografts from complement-mediated rejection.

The ability of a recombinant soluble form of CR1 to inhibit inflammation in the reversed passive Arthus reaction in rats was described by Yeh, C. G., et al.,*J. Immunol* (1991) 146:250–256. This soluble CR1 was obtained from Chinese hamster ovary (CHO) cells expressing a CR1 genetic construct which had been mutated to remove the transmembrane and cytoplasmic domains. The ability of a similar soluble CR1, produced recombinantly in CHO cells, to inhibit post-ischemic myocardial inflammation and necrosis in rats was reported by Weissman, H. F., et al., *Science* (1990) 249:146–151.

Proteins related to the RCA proteins have also been shown to be produced by viruses, presumably as a mechanism whereby infection by the virus can be facilitated, as reported by Kotwaal, J., et al., *Nature* (1988) 335:176–178; McNearney, T. A., *J Exp Med* (1987) 16:1525–1535.

Complete inhibition of the complement system on a long-term basis is not likely to be desirable in most individuals. In some cases of autoimmune disease, inhibition of the classical pathway alone may be sufficient. In the case of the xenograft transplants, however, stringent inhibition of both pathways may be important. Similar stringency may be required for other applications. Accordingly, alternative modulators of the complement system with regulatable binding activities would be desirable.

It is therefore an object of the present invention to provide modified complement regulators which can be administered in soluble form for treatment of inflammatory disorders or to reduce an individuals ability to reject foreign materials.

It is a further object of the present invention to provide modified complement regulators which are shorter and more easily and economically produced than the more complex naturally occurring proteins.

It is another object of the present invention to provide complement regulators which combine the activities of different complement regulators to provide enhanced capability of inhibiting complement proteins specifically and systemically, both in the classical and alternative pathways.

SUMMARY OF THE INVENTION

Analogs of RCA-encoded proteins which are modified full-length or truncated forms of these regulatory proteins are described and demonstrated to inhibit complement. These analogs include RCA proteins having site-specific mutations, RCA protein hybrids which contain one or more SCRs from more than one RCA protein, modifications of RCA recombinants in which SCRs are arranged in different orders, and truncated versions of RCA proteins containing as few three SCRs. The modified proteins retain complement inhibitory activity, which may be altered in specificity, affinity, or mechanism.

The modified proteins are demonstrated by the ΔSCR11, subst1 mutation of CR1–4(8,9) which carries only three complete SCRs (amino acids 1–194, SCR 1–3) and has C3b activity; the 1ar, 5r, 8br mutation of CR1–4(8,9) which has accentuated C3b and C4b activities; a three SCR form composed of the first 194 amino acids of 1ar, 5r, 8br; mutants 10, 10, 10, 11, 11c, 8a, 6b, 14, and 15, which are mutations of CR1–4 with enhanced activities; and CR1–4 stop7, CR1–4(8,9) stop7, and 1ar, 5r, 8br stop 7, which are all shorter (7 SCR) forms of their respective parent proteins (CR1–4, CR1–4(8,9) and 1ar, 5r, 8br, respectively).

These analogs are useful in controlling the complement system, and thus may be useful in the treatment of autoimmune diseases, the suppression of rejection of transplants, in diagnosis and the reduction in tissue damage associated with myocardial infarctions and cerebral vascular accidents. They may also play a role in the diagnosis of conditions associated with complement activation and immune complex formation.

BRIEF DESCRIPTION OF THE DRAWINGS

FIG. 1 is a schematic of the classical and alternate complement pathways.

FIGS. 2A and 2B compare the amino acid sequences of SCR-1 and SCR-8 (FIG. 2A) and SCR-2 and SCR-9 (FIG. 2B) of full-length CR1, indicating the substitutions made in SCR-1 and SCR-2 based on the amino acid residue present in corresponding SCR, as described in Examples 2 and 3 and Table 2.

FIGS. 3A and 3B compare the amino acid sequences of SCR-1 and SCR8 (Sequence ID Nos. 1 and 2, respectively) (FIG. 3A) and SCR-2 and SCR-9 (Sequence ID Nos. 3 and 4 respectively) (FIG. 3B) of full-length CR1. The amino acid sequences of SCR 15–16 are identical to those of SCR 8–9, with the exception of a T at position 110. The enumeration is consistent with that of Hourcade et al., *J. Exp. Med.* (1988) 168:1255–1270, with the first amino acid (Q) of the mature receptor designated as amino acid 1. The corresponding position in CR1 SCR-8 is similarly designated.

DETAILED DESCRIPTION OF THE INVENTION

Described herein is a family of RCA protein analogs which can be used to modulate the complement system. The analogues can be used to alter the binding specificity of the members of this protein family in both membrane-bound and soluble forms.

As used herein, "RCA proteins" refers to proteins encoded by the gene cluster at the genetic region lq32, which encodes six known proteins effective in complement regulation: factor H, C4bp, CR1, CR2, DAF and MCP. In addition, apparent coding regions similar to the amino terminal coding region of the CR1 gene and the MCP gene have been located in this cluster, although it is unclear whether these sequences are expressed (Hourcade, D., et al., *J. Biol. Chem.* 265:974–980 (1990); Hourcade, D., et al., *Genomics* 12:289–300 (1992)). The term "RCA proteins" also refers to a group of proteins which include short consensus repeats (SCR) which are homologous to SCR in CR1, CR2, MCP. DAF, factor H, and C4bp.

The modified proteins described herein are collectively referred to as "modified RCA proteins". These include truncated, hybrid and recombined forms of the RCA proteins. "Truncated" proteins are shorter versions of the RCA proteins, typically modified so as to remove the C-terminal regions which effect membrane binding or secretion and sometimes modified further by deletion of one or more SCRs. "Hybrid" proteins are RCA proteins that are composed of portions, i.e., the SCRs, of one RCA protein combined with SCRs of one or more other RCA proteins. "Recombined" forms are those wherein the SCRs of an RCA protein are rearranged in a new order. Also included are proteins having site specific substitutions and deletions of one or more amino acids. "Modified RCA proteins" include proteins which result from combinations of these changes.

CR1 contains 30 SCR, followed by transmembrane and cytoplasmic regions. CR2 contains 16 SCR, followed by transmembrane and cytoplasmic regions. DAF and MCP each contain four SCR, followed by glycolipid anchor regions. The C4 binding protein is a more complex protein, having seven alpha subunits and one beta subunit. The alpha subunit consists of eight SCR and the beta subunit consists of three SCR. Factor H consists of twenty SCR.

In some embodiments, modifications are made using corresponding SCRs of the protein as sites for alteration. By "corresponding SCR" is meant the most highly homologous SCR as judged by the amino acid sequences of the protein. Exon structure can in some cases facilitate this assignment. As noted above, SCRs 1–3 of CR1 correspond to SCRs 2–4 of DAF. SCRs 1–3 of factor H, CR1, C4bp and MCP are corresponding sequences among these proteins. CR1 is organized into a series of long homologous repeats (LHRS) containing 7 SCRs so that CR1 SCRs 1–7 correspond to CR1 SCRs 8–14; 15–21; and 22–28. CR2 is organized into a series of long homologous repeats of 4 SCRs in length. SCRs 1–2 of CR1 correspond to SCRs 3–4, SCRs 7–8, SCRs 11–12 and SCRs 15–16 of CR2.

These proteins are characterized by C4b-binding activity, C3b-binding activity, C4b cofactor activity, and C3b cofactor activity. In general, it takes two to three SCRs for each activity. Activities which are biologically important include decay acceleration or dissociation, C3b cofactor activity and C4b cofactor activity. Cofactor activity requires binding but binding alone may not be sufficient for cofactor activity.

It is generally accepted that CR1 C4b binding and cofactor activity requires SCRs 1, 2 and 3, 8, 9, and 10, or 15, 16, and 17, which are corresponding regions of the protein. C3b binding and cofactor activity requires SCRs 8, 9, and 10, or 15, 16, and 17, which are corresponding regions of the protein. MCP C4b binding and cofactor activity requires SCRs 1, 2, 3, and 4. MCP C3b binding requires SCRs 3 and 4; cofactor activity requires SCRs 2, 3, and 4. C4bp C4b binding and cofactor activity requires SCRs 1, 2, and 3. DAF decay accelerating activity requires SCRs 2, 3, and 4. Factor H C3b binding activity is mediated by the first five SCRs.

Based on these discoveries, it is possible to design a more potent soluble complement inhibitor by modifying corresponding regions to increase affinity for C4b and C3b or to design soluble complement inhibitors that specifically inhibit one part of the complement system. These modifications can be in the form of specific substitutions of amino acids that alter C3b or C4b binding within corresponding SCRs of CR1 or other RCA proteins, or substitution of SCRs from one protein into another.

Substitution of SCR Regions from on Regulatory Protein into a Second Regulatory Protein.

The identification of the amino acid sequences essential (or refractory) to binding to C4b and C3b and C4b and C3b cofactor activity permits transposition of similar sequences into corresponding regions of the same protein or corresponding regions of other family members or alteration of sequences which bind C3b and C4b so as to alter their affinities. Corresponding regions have been identified by degree of amino acid sequence homology.

In the case of CR1, four corresponding regions of interest are SCRs 1–3, SCRs 8–10, SCRs 15–17 and SCRs 22–24. The SCR portions 2–4 for DAF correspond to 1–3, 8–10, 15–17 and 22–24 for CR1. Substitution of portions of DAF with homologous CR1 sequences provides forms of DAF with cofactor activity and/or binding activity, such as is exhibited by CR1. Similarly, substitutions of portions of MCP with homologous sequences provides forms of MCP with increased binding affinity and cofactor activity and/or increased dissociation activity.

Specific Amino Acid Substitutions

Addition of Binding Sites

Specific amino acids are selected for substitution based on studies that elucidate their roles in complement regulation in specific active sites. Substitution can be employed in order to alter the activity of additional RCA active sites in the same or other proteins. In this manner, binding and cofactor sites can be added to SCRs not normally contributing directly to binding capacity.

The standard one letter abbreviations for amino acids are used herein.

For example, the C3b and C4b binding and f 4 cofactor sequence in CR1, N-A-A-H-W-S-T-K-P-P-I-C-Q (amino acids 49–61 of Sequence ID No. 4) can be transferred to corresponding locations or to locations referenced to conserved amino acids in alternative SCRs to confer C3b binding. Conversely, the homologous sequence in SCR-2 of CR1, i.e., D-T-V-W-D-N-E-T-P-I-C-D (amino acids 49–61 of Sequence ID No. 3) can be transferred by substitution to other locations in C3b-binding SCRs in order to decrease C3b and C4b binding and cofactor activity. The C4b binding regions are shown to be associated with three separate critical locations in SCR-1 and SCR-2 of CR1 in the proximity of amino acids 35, 64–65, and 92–94. Alterations in amino acid sequences of the corresponding SCRs in CR1 or in additional RCA family members or their truncated, hybrid, or recombined forms in these positions alter C4b binding and cofactor activities and in at least one case alter C3b binding and cofactor activities.

Substitution of Similar Amino Acids

Structurally similar amino acids can be substituted in such transfers for some of the specified amino acids. Structurally similar amino acids include: (I,L,V); (F,Y); (K,R); (Q,N); (D,E); and (G,A).

Deletion of Amino Acids

It also may be advantageous to delete amino acids from specific active sites in order to alter or enhance complement regulatory activity.

Construction of Truncated Forms

In some embodiments, it will be advantageous to delete a specific activity by deletion of a region known to have a particular activity. It may also be desirable to delete the region of the protein which anchors the naturally occurring protein to the cell surface, for example, the transmembrane and cytoplasmic regions or the glycolipid anchor region.

Modifications which Enhance Cofactor Activity

In general, either C3b or C4b cofactor activity can be enhanced by substitutions which increase the binding activity of the other factor, i.e., to increase C4b cofactor activity, amino acids are substituted into the modified protein which increase C3b binding and vice versa. This is demonstrated in the examples, specifically by the mutants shown in Table 2. An example of a single amino acid substitution that enhances both C4b cofactor activity and C3b cofactor activity is CR1 mutant 6b: changing the G at 79 to D increases C4b cofactor, as well as C3b binding and cofactor activity.

Preparation of the Analogs

The modified proteins described herein are most conveniently prepared using recombinant techniques, although in some cases they can be prepared by enzymatic cleavage, for example, to yield truncated or soluble forms of the naturally occurring proteins. The genes encoding the various members of the RCA protein family are of known sequence and are published.

cDNA encoding CR1 has been described by Klickstein, L. B., et al., *J. Exp. Med.* (1987) 165:1095, Klickstein, L. B., et al., *J. Exp. Med.* (1988) 168:1699; Hourcade, D., et al., *J. Exp. Med.* (1988) 168:1255, the teachings of which are incorporated by reference. Sequence ID No. 12 is the nucleotide sequence and Sequence ID No. 13 is the amino acid sequence for CR1. Sequence ID No. 14 is the nucleotide sequence and Sequence ID No. 15 is the amino acid sequence for CR2. Sequence ID No. 16 is the nucleotide sequence and Sequence ID No. 17 is the amino acid sequence for DAF. Sequence ID No. 18 is the nucleotide sequence and Sequence ID No. 19 is the amino acid sequence for MCP.

The cDNA encoding CR2 has been described by Moore, M. D., et al., *Proc. Natl. Acad. Sci. USA* (1987) 84:9194, and by Weiss, J. J., et al., *J. Exp. Med.* (1988) 167:1047, the teachings of which are incorporated by reference.

The cDNA encoding DAF has been described by Caras, I. W., et al., *Nature* (1987) 325:545, and by Medof, M. E., et al., *Proc. Natl. Acad. Sci. USA* (1987) 84:2007, the teachings of which are incorporated by reference.

The cDNA encoding MCP has been described by Lublin, D.M., et al., *J. Exp. Med.* (1988) 168:181, the teachings of which are incorporated by reference.

The cDNa encoding the C4bp alpha chain has been described by Chung, L. P, et al., *Biochem. J.* (1985) 230:133, and the cDNA encoding the C4bp beta chain has been described by Hillarp, A., and Dahlback, B., *Proc. Natl. Acad. Sci. USA* (1990) 87:1183, the teachings of which are incorporated by reference.

The cDNA encoding factor H has been described by Ripoche, J., et al., *Biochem. J.* (1988) 249:593, the teachings of which are incorporated by reference.

Since the cDNAs encoding these proteins are known and the amino acid sequences have been deduced, comparison of corresponding regions of the various proteins of the member families has been possible. In addition, the availability of the cDNA sequence makes possible the preparation of genetic constructs encoding truncated forms and other modified forms of the proteins using standard site-directed mutagenesis techniques, such as those described by Kunkel, T. A., et al., *Methods Enzymol* (1987) 154:367–382.

Accordingly, the first step in the preparation of the analogs requires identification of the corresponding region of the target protein through sequence homology and site-directed mutagenesis in this region of the gene to alter C4b or C3b binding properties.

After the gene encoding the analog is prepared, the modified gene is expressed using standard recombinant techniques. The gene sequence is ligated into a suitable expression vector under the control of sequences known to be appropriate to the desired host. Production of recombinant proteins in microbial systems such as *E. coli, B. subtilis*, various strains of yeasts, and other fungi, such as *Aspergillus*, is well known. It may be advantageous to produce the desired analogs in cells of higher organisms as well, such as the standard BPV/C127 system, the Baculovirus/insect cell system, CHO cells, COS cells, and other mammalian cells, or in transgenic animals. Standard expression systems in various cell lines are well known and standard in the art.

Transgenic animals can be constructed for several species. The gene is placed under the control of a suitable promoter, for example, the metallothionine promoter or a tissue specific promoter, and the gene microinjected into an embryo, which is then implanted into a surrogate mother. Production in transgenic animals is important in the context of preparing transplants for use in other species.

Construction of Transgenic Animals.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo, Cold Spring Harbor Laboratory, Cold Spring Harbor, NY (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods

Introduction of cDNA into ES cells:

Methods for the culturing of ES cells and the, subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the gene of interest or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid sequence and 1 mg of pSV2neo DNA (Southern and Berg, *J. Mol. Appl. Gen.* 1:327–341 (1982)) precipitated in the presence of 50 mg lipofectin in a final volume of 100 $\mu$l. The cells are fed with selection medium containing 10% fetal bovine serum in DMEM supplemented with an antibiotic such as G418 (between 200 and 500 $\mu$g/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 μm.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals.

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

Purification of Analogs

The analogs recombinantly produced in culture or animals can be purified from the cell culture using standard purification techniques such as chromatography, for example, immunoaffinity or ion-exchange chromatography, and electrophoresis, generally using the same procedures as have been published for use in purifying the naturally occurring material.

While recombinant production of the analogs is the most convenient and practical method of preparing the proteins, it may also be desirable to synthesize the analogs using protein synthesis techniques, such as standard solid-phase peptide synthesis technology. This approach may be suitable in particular in the case of truncated forms of the RCA protein family having modified amino acid sequences, especially in view of the discovery that proteins containing as few as three SCRs have useful biological activity.

Assay Systems

The analogs are tested for the desired biological activities among those characteristic of the RCA family using in vitro or in vivo assays. In vitro systems such as those described by Wong and Farrell (*J. Immunol.* (1991) 146:656) can be used to measure effects on the complement pathways. In vivo and general biological effects can be assessed as described by Weisman, et al. (*Science* (1990) 249:146); or Yeh, et al. (*J. Immunol.* (1991) 146:250), the teachings of which are incorporated by reference.

Binding Assays.

Affinity chromatography columns were prepared as described by Krych, et al., *Proc. Natl. Acad. Sci. USA* 88, 4353–4357. Binding assays were performed using 100 ml of iC3-Sepharose (iC3-S) or C4b-Sepharose (C4b-S) and 1.8 ml of medium containing of the mutant protein. Media were diluted to desired concentrations of NaCl. After 1 hr on a rotator at room temperature, samples were centrifuged, media removed and bound protein eluted from the Sepharose using 400 mM NaCl with 1% NP-40. Eluted proteins were quantitated by ELISA, using two monoclonal anti-CR1 antibodies, 3D9 and E11 (Hogg, et al., *Eur. J. Immunol.* 14, 236–240 (1984), O'Shea, et al., *J. Immunol.* 134, 2580–2587 (1985)). Since neither monoclonal antibody reacts with CR1 SCRs-1, 2, 8 or 9, all of the mutants derived, from either CR1–4 or CR1–4(8,9) could be quantitated: using this assay. For each mutant protein at least three binding assays from different transfections were performed.

Assay for Cofactor Activity

C3 and C4 were purified according to the method of Dykman, et al., *Proc. Natl. Acad. Sci. USA* 80, 1698–1702 (1983), Dykman, et al., *J. Exp. Med.* 157, 2160–2165 (1983) or purchased (Quidel, San Diego, Calif.), converted to C3b and C4b and labelled with $^{125}I$ using Iodogen coated beads (Pierce). Cofactor assays were performed using 200 ng of labelled C3b or C4b, 60 ng of factor I (Quidel) and media with mutant proteins. Amounts of the cofactor proteins were estimated in ELISA assay based on a standard curve of secreted CR1 (sCR1, Weisman, et al., *Science* 249, 146–151 (1990)). To test for cleavage of C3b, samples containing approximately 6 pg of the mutant proteins were incubated for 1 hr at 37° C. To test for cleavage of C4b, samples were incubated for up to 16 hrs at 37° C. After incubation, samples were reduced by boiling in the buffer containing 2% SDS and 5% beta-mercaptoethanol in 0.25% TRIS, pH 6.8 and electrophoresed on a 4–20% SDS-PAG (Integrated Separations) or on a 10% self-made gel. After drying the gels were autoradiographed at –70° C. using an intensifying screen.

Preparation and Administration of Pharmaceutical Compositions

The most potent analogs based on the in vitro assays are tested in vivo. In general, the in vitro assays are accepted as highly correlated with the corresponding in vivo activity. The appropriate dosages are determined by comparing the in vitro activity of the naturally occurring protein with that of the analog, comparing the in vitro activity of the naturally occurring protein with the in vivo activity of the naturally occurring protein, then calculating the expected in vivo activity of the analog, adjusting for any measured differences in half-life.

Complement activation can account for substantial tissue damage in a wide variety of autoimmune/immune complex mediated syndromes such as systemic lupus erythematosus, rheumatoid arthritis, hemolytic anemias, myasthenia gravis and others. Inhibition of the complement system is a desirable therapeutic intervention in these cases. In some instances, specific inhibition of the classical pathway alone by RCA analogs could be preferred since long-term inhibition of the alternative pathway could lead to side effects.

Inhibition of complement activation could also be desirable in cases that involve tissue damage brought about by vascular injury such as myocardial infarction, cerebral vascular accidents or acute shock lung syndrome. In these cases, the complement system may contribute to the destruction of partially damaged tissue as in reperfusion injury. Highly stringent inhibition of complement for relatively brief periods might be preferred in these instances and soluble RCA analogs designed for higher potency may prove especially useful.

Complement inhibition may also prove important in the prevention of xenograft rejection. Organs derived from animals transgenic for human DAF or MCP may be protected at least in part from complement-mediated hyperacute rejection by the expression of transgenic DAF or MCP on the cell surfaces of the xenograft. Animals transgenic for RCA analogs designed for higher potency may provide more successful xenografts. Soluble RCA analogs may also prove useful in protecting the transplant in the recipient.

Soluble analogs having decreased activity may also be useful as competitive inhibitors of the natural inhibitors, in cases where an increased complement mediated response is desirable or where an individual has a disorder in which their immunity is compromised by overproduction of the natural inhibitors.

The analogs can be administered locally or systemically in pharmaceutically acceptable carries such as saline, phosphate buffered saline, or a controlled release formulation. The dosage level and mode of administration of the analogs depend on the nature of the analog, the nature of the condition to be treated, and the history of the individual patient. Systemic administration is generally required, which may be by injection or by transmucosal or transdermal delivery. Administration by injection may be intravenous, intramuscular, intraperitoneal or subcutaneous. Formulations for injection are generally biocompatible solutions of the active ingredient such as Hank's solution or Ringer's solution. Formulations for transdermal or transmucosal administration generally include penetrants such as fusidic acid or bile salts in combination with detergents or surface-active agents. The formulations can then be manufactured as aerosols, suppositories, or patches. Oral administration is generally not favored for protein or peptide active ingredients; however, if suitably formulated so as to be protected from the digestive enzymes, oral administration can also be employed.

Suitable formulations for a desired mode of administration can be found in *Remington's Pharmaceutical Sciences*, latest edition, Mack Publishing Co., Easton, Pa. The dosage levels and precise formulations are obtainable by routine optimization procedures as is generally known in the art.

Diagnostic Applications

The analogs which are capable of binding C3b and/or C4b are useful as diagnostic tools in assessing the presence, absence or amount of C3b or C4b or C3b/C4b-bearing immune complexes in biological fluids. Such assays take advantage of the ability of the analog specifically to bind C3b and/or C4b and can be conducted in a variety of formats as is generally known. Formats for specific binding partner assays include direct and competitive formats, sandwich assays, and agglutination assays. Complexation between members of the specific binding pair can be conducted in solution or on a solid phase and can be detected using a variety of labeling techniques including fluorescence, radioisotopes, chromophores, and visible particles.

Typical reagent kits useful in assays for C3b and/or C4b and/or C3b/C4b-bearing immune complexes include the analog specifically binding to the analyte, optionally coupled to a solid support and additional labeling reagents useful in the assay. For example, one of many formats for the assay might include treating the sample to be tested with a solid support to which is coupled the analog as a specific binding partner, washing the support which has been treated with sample suspected of containing analyte, and then treating the washed support with anti-C3b or anti-C4b antibody labeled with an enzyme such as horseradish peroxidase. The presence of labeled enzyme on a support then is detected by addition of a substrate solution which results in the development of a color in the presence of the enzyme.

The present invention will be further understood by reference to the following non-limiting examples.

EXAMPLE 1

Binding Specificity of Truncated CR1

The cDNA which encodes the first 543 amino acids of mature CR1 (SCR 1–8 and ½ of SCR-9) was transfected into COS cells to obtain a secreted protein designated CR1-4.

Two mouse monoclonal anti-CR1 antibodies were used to determine the immunoreactivity of CR1-4, and as a method to assay for this protein. Antibody E11 (Hogg, N., et al., *Eur. J. Immunol.* (1984) 14:236–243), and 3D9 (O'Shea, J. J., et al., *J. Immunol.* (1985) 134:2580–2587), recognized CR1 and bound to the recombinantly produced CR1-4.

Binding to C4b or to C3b was tested using either C4b or iC3 (C3 containing a broken thioester bond analogous in reactivity and function to C3b) bound to a Sepharose™ support as described by Dykman, T., et al., *Proc. Natl. Acad. Sci. USA* (1983) 80:1698–1702, and Cole, J. L., et al., *Proc. Natl. Acad. Sci. USA* (1985) 82:859–863. Binding to these solid-supported substrates was verified by testing with an ELISA for CR1.

The C4b derivatized support was able to bind CR1-4. Most efficient binding occurred at between 12.5 and 25 mM salt.

Solubilized C4b inhibited binding of the CR1-4 protein to C4b-derivatized support but soluble iC3 did not inhibit this binding. This confirms that CR1-4 binds primarily C4b but not iC3 (C3b).

EXAMPLE 2

Construction of CR1-4 Analogs

Various mutated forms of CR1-4 were constructed and tested for binding activity to C4b and iC3 as described above in Example 1. Table 2 shows the analogs constructed and the binding and cofactor activities of the analogs. In Table 2, the modifications are shown by the number of the amino acid and the conversion effected. The numbers correspond to those set forth in FIGS. 2A and 2B and FIGS. 3A and 3B which set forth the amino sequences of SCR-1 (Sequence ID No. 1), SCR-2, (Sequence ID No. 3) SCR-8 (Sequence ID No. 2) and SCR-9 (Sequence ID No. 4) in CR1.

The combined changes shown in truncated forms should be predictive of the activity of a modified full length protein. There is strong evidence available that establishes three primary binding and cofactor sites in the major polymorphic form (30 SCRs) of CR1. One site interacts almost exclusively with C4b (SCRs 1–4) while the other two sites, nearly identical in amino acid sequence, interact with both C4b and C3b (SCRs 8–11 and SCRs 15–18) [Klickstein, L. B., et al., *J. Exp. Med.* 168: 1699–1717 (1988); Kalli, et al., *J. Exp. Med.* 174: 1451–1460 (1991); Makrides, S. C., et al., *J. Biol. Chem.* 267: 24754–24761 (1992)].

Electron microscope analysis of CR1 suggests that CR1 is a semi-rigid rod composed of individual globular domains (the SCRs). Thus, CR1 is pictured as an elongated protein bearing well-separated active sites. These sites may not work cooperatively. A comparison of several polymorphic forms, containing the first site (SCRs 1–4) and one, two and three copies of the second site, demonstrated little difference among them in cofactor and decay acceleration assays, as reported by Seya, T., et al., *J. Immunology* 135: 2661 (1985). Indeed, after the filing of the application to which this claims priority, it was shown that modified membrane forms of CR1 bearing a single active site alone (SCR 1–4 or SCR 15–18) could protect CHO cells from human complement-mediated lysis (Makrides, S. C., et al., *J. Biol. Chem.* 267: 24754–24761 (1992)). This provides evidence that a simple CR1 form with a single active site could be biologically active, and that modifications that improve the activity of each primary site in the constructs could be incorporated together in a multiple-site CR1 form, yielding an improved regulator.

TABLE 2

CR1-4 Mutants

| Designation | Description[a] | C4b-binding | C3b-binding | C4b cofactor activity | C3b cofactor activity |
|---|---|---|---|---|---|
| CR1-4 | original peptide | +++ | + | ++ | + |
| ΔSCR-1 | amino acids 1–60 deleted | – | – | ND | ND |
| ΔSCR-2 | amino acids 61–122 deleted | – | – | ND | ND |
| ΔSCR-3 | amino acids 123–194 deleted | ND | ND | – | – |
| CR1-4 | stop 7 truncated after amino acid 449 | ND | + | ++ | + |
| 1 | 35: G→E (amino acid 35 of Sequence ID Nos. 1 and 2, respectively); 37: S→Y (amino acid 37 of Sequence ID Nos. 1 and 2, respectively) | + | + | – | ++ |
| 1a | 35: G→E (amino acid 35 of Sequence ID Nos. 1 and 2, respectively) | + | + | + | + |
| 1b | 37: S→Y (amino acid 37 of Sequence ID Nos. 1 and 2 respectively) | ++ | ++ | + | + |
| 2 | 44, 47, 49: I . . . K . . . S→T . . . D . . . L (amino acids 44, 47 and 49 of Sequence ID Nos. 1 and 2, respectively) | +++ | + | ++ | + |
| 3 | 52→54: T-G-A→S-S-P (amino acids 52–54 of Sequence ID Nos. 1 and 2, respectively) | +++ | + | ++ | + |
| 4 | 57, 59: R . . . R→V . . . K (amino acids 57, 59 of Sequence ID Nos. 1 and 2, respectively) | +++ | + | ++ | + |
| 5 | 64, 65: R-N→K-T (amino acids 4, 5 of Sequence ID Nos. 3 and 4, respectively) | + | + | – | + |
| 5a | 64: R→K (amino acid 4 of Sequence ID No. 3 and 4, respectively) | +/– | – | ND | ND |
| 5b | 65: N→T (amino acid 5 of Sequence ID Nos. 3 and 4, respectively) | +/– | – | ND | ND |
| 6 | 78, 79: K-G→T-D (amino acids 18, 19 of Sequence ID Nos. 3 and 4, respectively) | +++ | + | ++ | + |
| 6b | 79: G→D (amino acid 19 of Sequence ID Nos. 3 and 4, respectively) | +++ | +++ | +++ | +++ |
| 1b, 6b | 37, 79: S→Y; G→D (amino acid 37 of Sequence ID Nos. 1 and 2, and amino acid 19 of Sequence ID Nos. 3 and 4, respectively) | +++ | ++ | + | + |
| 7 | 85, 87: Q . . . K→R . . . N (amino acids 25, 27 of Sequence ID Nos. 3 and 4) | +++ | + | ++ | + |
| 8 | 92, 94: K . . . Y→T . . . H (amino acids 32 and 34 of Sequence ID Nos. 3 and 4 respectively) | + | + | – | + |
| 8a | 92: K→T (amino acid 32 of Sequence ID Nos. 3 and 4 respectively) | +++ | + | +++ | ++ |
| 8b | 94: Y→H (amino acid 34 of Sequence ID Nos. 3 and 4 respectively) | + | + | – | + |
| 9 | 99, 103: S . . . T→H . . . E (amino acids 38 and 43 of Sequence ID Nos. 3 and 4 respectively) | +++ | + | ++ | + |
| 10 | 109–112: D-T-V-I→N-A-A-H (amino acids 49–52 of Sequence ID Nos. 3 and 4 respectively) | ++++ | ++ | +++ | ++ |
| 10, 11 | 109–112: D-T-V-I→N-A-A-H; 114–117, 121: D-N-E-T . . . D→S-T-K-P . . . Q (amino acids 49–52 of Sequence ID Nos. 3 and 4 respectively); amino acids 54–61 of Sequence ID Nos. 3 and 4 respectively) | +++ | +++ | +++ | +++ |
| 11 | 114–117, 121: D-N-E-T . . . . D→S-T-K-P . . . Q (amino acids 54–61 of Sequence ID Nos. 3 and 4 respectively) | +++ | ++ | ++ | + |
| 11a | 114: D→S (amino acid 54 of Sequence ID Nos. 3 and 4 respectively) | +++ | + | ND | ND |
| 11b | 115: N→T (amino acid 55 of Sequence ID Nos. 3 and 4 respectively) | +++ | + | ND | ND |
| 11c | 116: E→K (amino acid 56 of Sequence ID Nos. 3 and 4 respectively) | ++++ | ++ | +++ | +++ |
| 11d | 117: T-P (amino acid 57 of Sequence ID Nos. 3 and 4, respectively) | +++ | + | ND | ND |
| 11c, d | 116, 117: E-T→K-P (amino acids 56 and 57 of Sequence ID Nos. 3 and 4 respectively) | ++++ | ++ | +++ | +++ |
| 11e | 121: D→Q (amino acid 61 of Sequence ID Nos. 3 and 4 respectively) | +++ | + | ND | ND |
| 11ΔSCR1 | 1–60 deleted, 114–117, 121: D-N-E-T . . . D→S-T-K-P . . . Q (amino acids 54–61 of Sequence ID Nos. 3 and 4 respectively) | ++ | ++ | ++ | ++ |
| 12 | 1, 3: Q . . . N→H . . . Q (amino acids 1–3 of Sequence ID Nos. 1 and 2, respectively) | + | + | ++ | + |
| 13 | 6–9: E-W-L-P→D-H-F-L (amino acids of 6–9 of Sequence ID Nos. 1 and 2, respectively) | + | + | ++ | + |
| 14 | 12–16, 18–21: R-P-T-N-L . . . D-E-F-E→K-L-K-T-Q . . . N-A-S-D (amino acids 12–16 and 18–21 of Sequence ID Nos. 1 and 2, respectively) | ++++ | ++ | +++ | +++ |
| 15 | 27, 29: Y . . . N→S . . . K (amino acids 27 and 29 of Sequence ID Nos. 1 and 2, respectively) | ++++ | ++ | +++ | +++ |

ND Not determined.
. . . intervening amino acids which were not changed.

As shown in Table 2, deletion of either SCR-1 or SCR-2 results in loss of C4b-binding activity; thus both regions are required for binding to C4b. Binding to C3b is conferred by insertion of the SCR-9 sequence S-T-K-P-(P-I-C)-Q (amino acids 54–61 of Sequence ID No. 4) into SCR-2 (Sequence ID No. 3); however, deletion of SCR-1 (Sequence ID No. 1) partially eliminates binding to C3b in this analog. Thus, efficient binding to C3b requires not only the relevant sequence in SCR-2 (Sequence ID No. 3), but an additional portion of SCR-1 (Sequence ID No. 1). The ability to bind C3b conferred by altering the sequence in SCR-2 (Sequence ID No. 3) does not affect binding to C4b.

As also shown by Table 2, it is possible to weaken or destroy binding to C4b by altering amino acids 35, 64–65 or 94. It is possible to strengthen C4b binding by altering amino acid 92.

These results indicate that by manipulation of C3b and C4b binding sites in CR1 the affinity and specificity of CR1–4 can be altered. Similar alterations may be made to corresponding regions in additional members of the RCA protein family.

EXAMPLE 3

Construction of a More Potent Soluble CR1 Analog

A stringent inhibitor of the complement system has applications where higher potency is required. In this example, the sCR1 sequence is used as starting material for a family of analogs of higher inhibitory capacity for both classical and alternative pathways. Other CR1 truncated, full-length, recombined or hybrid forms or CR1 could also be used.

As noted above, the sCR1 protein contains four corresponding regions: SCRs 1–2 (Sequence ID No. 1 and 3 respectively), SCRs 8–9 (Sequence ID No. 2 and 4 respectively), SCRs 15–16 and SCRs 22–23. The primary C4b-binding site is within SCRs 1–2 (Sequence ID No. 1 and 3 respectively), and the two primary C3b-binding sites are in SCRs 8–9 (Sequence ID No. 2 and 4 respectively) and SCRs 15–16. SCRs 22–23 has no reported binding activity although it is highly homologous in amino acid sequence to the other three corresponding regions.

One or more substitutions are introduced into the corresponding positions of soluble CR1 SCRs 1–2, 8–9, 15–16, and 22–23. Specific substitutions designed to increase C3b and C4b cofactor activity and binding activity are selected from the following:

| positions | substitution |
| --- | --- |
| 35 | G (amino acid 35 of Sequence ID No. 1) |
| 64–65 | R-N (amino acids 4–5 of Sequence ID No. 3) |
| 94 | Y (amino acid 34 of Sequence ID No. 3) |
| 109–112 | N-A-A-H (amino acids 49–52 of Sequence ID No. 4) |
| 114–121 | S-T-K-P-P-I-C-Q (amino acids 54–61 of Sequence ID No. 4) |
| 109–121 | N-A-A-H-W-S-T-K-P-P-I-C-Q (amino acids 49–61 of Sequence ID No. 4) |
| 92 | T (amino acid 32 of Sequence ID No. 4) |
| 79 | D (amino acid 19 of Sequence ID No. 4) |
| 12–16 | K-L-K-T-Q (amino acids 12–16 of Sequence ID No. 2) |
| 18–21 | N-A-S-D (amino acids 18–21 of Sequence ID No. 2) |
| 12–21 | K-L-K-T-Q-T-N-A-S-D (amino acids 12–21 of Sequence ID No. 2) |
| 27–29 | S-L-K (amino acids 27–29 of Sequence ID No. 2) |

In some cases, some of these amino acids may already be present in the corresponding position. In some cases structurally similar amino acids may be substituted instead of those substituted above.

The use of these substitutions at some or all four corresponding positions will yield a full length soluble CR1 form with more potent active sites, and with an additional active site at SCR 22–24.

Substitutions described above were introduced into the four corresponding regions of interest in order to increase the affinity of sCR1 for its C3b and C4b-containing targets. These modifications were designed to increase the use of existing coenzyme and dissociation functions and potentially to establish new coenzyme and dissociation functions. The introduction of amino acid sequences significant to C3b binding into the C4b binding region presumably would not interfere substantially with C4b activities since such a substitution in CR1–4 did not detectably alter the C4b binding properties of CR1–4. The introduction of amino acids significant to C4b-binding into C3b-binding regions presumably would not interfere substantially with C3b binding activities since substantial C3b-binding occurs in CR1–4 mutant 11, in which many amino acids specific to SCRs 1–2, including those significant in C4b binding, are already present.

Specific substitutions as shown in FIGS. 2A and 2B and FIGS. 3A and 3B designed to increase affinity to C4b were described in Example 3: SCRs 1–2 (Sequence ID No. 1 and 3 respectively), the primary C4b-binding site of CR1, modified by replacement of K (amino acid 32 of Sequence ID No. 3) at position 92 with T (amino acid 32 of Sequence ID No. 4); SCRs 8–9 (Sequence ID Nos. 2 and 4) and the identical SCRs 15–16 modified by replacement of E (amino acid 35 of Sequence ID No. 2) at a position corresponding to 35 by G (amino acid 35 of Sequence ID No. 1) (or A), H (amino acid 34 of Sequence ID No. 4) at a position corresponding to 94 by Y (amino acid 34 of Sequence ID No. 3) (or F), K (amino acid 4 of Sequence ID No. 4) at a position corresponding to 64 by R (amino acid 4 of Sequence ID No. 3) and T (amino acid 5 of Sequence ID No. 4) at a position corresponding to 65 by N (amino acid 5 of Sequence ID No. 3) (or Q). SCRs 22–23 were also modified by replacement of G at a position corresponding to 64 by R (amino acid 4 of Sequence ID No. 3) (or K) (amino acid 4 of Sequence ID No. 4), P at a position corresponding to 65 with N (amino acid 5 of Sequence ID No. 3) (or Q), E at a position corresponding to 92 with and T (amino acid 32 of Sequence ID No. 4) at a position corresponding to 94 with Y (amino acid 34 of Sequence ID No. 3).

Together, these modifications result in higher affinity for C4b and may also result in the establishment of new coenzyme or dissociation functions or the improvement in the capacity of the coenzyme and dissociation functions present on the sCR1 starting material.

As described in previous examples, substitution of a short stretch of amino acids into SCRs 1–2 (Sequence ID Nos. 1 and 3) of CR1–4 by corresponding amino acids of SCRs 8–9 (amino acid 34 of Sequence ID No. 3) confers C3b binding capacity to CR1–4. Replacement of D-N-E-T-P-I-C-D (amino acid 54–61 of Sequence ID No. 3) at position 114–121 in SCR1 SCRs 1–2 by S-T-K-P-P-I-C-Q (amino acid 54–61 of Sequence ID No. 4) increases the affinity of SCR1 for C3b. Further, replacement of D-K-K-A-P-I-C-D (Sequence ID No. 5) at positions 114–121 in SCRs 22–23 by S-T-K-P-P-I-C-Q (amino acid 54–61 of Sequence ID No. 4) increases the affinity of sCR1 for C3b. Some structurally similar amino acids may also be substituted in the sequence.

A more potent complement inhibitor, in general, provides increased C4b-binding and increased C3b-binding. This is achieved by introducing all the modifications set forth above.

EXAMPLE 4

Construction of Truncated CR1 Mutants Having Increased Activity

More than 25 mutants were assayed for cofactor activity at several different salt concentrations. The assay was done as described in Adams, E. M., Brown, M. C., Nunge, M., Krych, M., and Atkinson, J. P. (1991) *J. Immunology*, 147: 3005–3011.

A number of mutations of the active sites in SCRs 1–3, the site that normally interacts with C4b and not C3b, which improve on the natural activity of this site, both for C4b and C3b cofactor activity. At least one mutant in the active sites in SCR 8–11, which is apparently the more potent natural active site, that improves on the cofactor activity of this site for both C3b and C4b was also detected.

In summary, specific CR1 proteins that have both C3b and C4b cofactor activity and are in some ways an improvement on the full length soluble CR1 have now been identified. These constructs are less than one-fourth (seven SCR constructs) to a third the size of soluble CR1 (sCR1) and have both C4b binding and cofactor activity as well as C3b binding and cofactor activity. Constructs including as few as three SCRs appear to have C3b cofactor activity, indicative of C3b binding activity. In some cases the data indicates that the modified active site appears to be more potent than the natural active sites.

These forms and their activities are shown in Table 3:

TABLE 3

Activities of CR1-4(8, 9) Mutants.

| Designation | Description | C4b-binding | C3b-binding | C4b cofactor activity | C3b cofactor activity |
|---|---|---|---|---|---|
| CR1-4 (8, 9) | * | ++++ | ++++ | ++++ | ++++ |
| ΔSGR10 | deletion of amino acids 123–194 | ND ND | ND ND | – – | – – |
| ΔSCR11, subst1 | ** | ND | ND | ND | ++++ |
| CR1-4 (8, 9) | stop 7 truncated after amino acid 449 | ND | ++++ | ++++ | ++++ |
| 1br | 37: Y→S (amino acid 37 of Sequence ID Nos. 2 and 1, respectively) | ++++ | +++ | ++++ | ++ |
| 2r | 44, 47, 49: T . . . D . . . L→I . . . K . . . S (amino acids 44, 47 and 49 of Sequence ID Nos. 2 and 1, respectively) | ++++ | +++ | ++++ | +++ |
| 3r | 52–54, 57, 59: S-S-P . . . V . . . K→T-G-A . . . R . . . R (amino acids 52–54, 57, 59 of Sequence ID Nos. 2 and 1, respectively) | +++ | ++ | ++++ | ++++ |
| 6r | 78–79, 82: T-D . . . V→K-G . . . F (amino acids 18–19, 22 of Sequence ID Nos. 4 and 3, respectively) | ++ | ++++ | ++++ | ++++ |
| 7r | 85, 87: R . . . N→Q . . . K (amino acids 25, 27 of Sequence ID Nos. 4 and 3, respectively) | ++++ | +++ | ++++ | ++++ |
| 8r | 92, 94: T . . . H→K . . . Y (amino acids 32–34 of Sequence ID Nos. 4 and 3, respectively) | ++++ | ++++ | ++++ | ++++ |
| 9r | 99, 103, 106: H . . . E . . . L→S . . . T . . . I (amino acids 39, 43 and 46 of Sequence ID Nos. 4 and 3, respectively) | ++++ | ++++ | +++ | ++++ |
| 10r | 109–112: N-A-A-H→D-T-V-I (amino acids 49–52 of Sequence ID Nos. 4 and 3, respectively) | +++ | ++ | ++ | ++ |
| 10br | 110: A→T (amino acid 50 of Sequence ID Nos. 4 and 3, respectively) | ++++ | ++++ | ++++ | ++++ |
| 10cr | 111: A-V (amino acid 51 of Sequence ID Nos. 4 and 3, respectively) | ++++ | ++++ | ++++ | ++++ |
| 10dr | 112: H→I (amino acid 52 of Sequence ID Nos. 4 and 3, respectively) | ++++ | ++++ | ++++ | ++++ |
| 10ar | 109: N→D (amino acid 49 of Sequence ID Nos. 4 and 3, respectively) | ++ | ++ | + | ++ |
| 11r | 114–117, 121: S-T-K-P . . . Q→D-N-E-T . . . D (amino acids 54–57, 61 of Sequence ID Nos. 4 and 3, respectively) | +++ | ++ | +++ | + |
| 11ar | 114: S→D (amino acid 54 of Sequence ID Nos. 4 and 3, respectively) | ++++ | ++++ | ++++ | ++++ |
| 11br | 115: T→N (amino acid 55 of Sequence ID Nos. 4 and 3, respectively) | ++++ | ++++ | ++++ | ++++ |
| 11er | 121: Q→D (amino acid 61 of Sequence ID Nos. 4 and 3, respectively) | ++++ | ++++ | ++++ | ++++ |
| 11cr | 116: K→E (amino acid 56 of Sequence ID Nos. 4 and 3, respectively) | +++ | +++ | + | + |
| 11dr | 117: P→T (amino acid 57 of Sequence ID Nos. 4 and 3, respectively) | +++ | +++ | ++++ | ++++ |
| 10, 11r | 109–112, 114–117, 121: N-A-A-H . . . S-T-K-P . . . Q→D-T-V-I . . . D-N-E-T . . . D (amino acids 49–52, 54–57, 61 of Sequence ID Nos. 4 and 3, respectively) | + | + | ++ | – |
| 12r | 1, 3: H . . . Q→Q . . . N (amino acids 1 and 3 of Sequence ID Nos. 2 and 1, respectively) | ++++ | ++++ | ++++ | ++++ |
| 13r | 6-9: D-H-F-L→E-W-L-P (amino acids 6–9 of Sequence ID Nos. 2 and 1, respectively) | ++++ | ++++ | ++++ | ++++ |
| 14r | 12–16, 18–21: K-L-K-T-Q . . . N-A-S-D→R-P-T-N-L . . . D-E-F-E (amino acids 12–16, 18–21 of Sequence ID Nos. 2 and 1, respectively) | +++ | +++ | ++++ | +++ |
| 15r | 27, 29: S . . . K→Y . . . N (amino acids 27 and 29 of Sequence ID Nos. 2 and 1, respectively) | +++ | ++++ | ++++ | +++ |
| 1ar, 5r, 8br | 35, 64–65, 94: E . . . K-T . . . H→G . . . R-N . . . Y (amino acid 35 of Sequence ID Nos. 2 and 1, amino acids 4–5 and 34 of Sequence ID Nos. 4 and 3, respectively) | +++++ | +++++ | +++++ | +++++ |

\* CR1-4 with its first 122 amino acids (SCR1-2) replaced with CR1 amino acids 497–618 (SCR 8-9), as enumerated by Klickstein, L. B., J. Exp. Med. 168:1699–1717.
\*\* CR1-4 (8, 9) with deletion of 194–253; substitution of amino acids 271–543 with: T-R-T-T-F-H-L-G-R-K-C-S-T-A-V-S-P-A-T-T-S-E-G-L-R-L-C-A-A-H-P-R-E-T-G-A-L-Q-P-P-H-V-K (Sequence ID No. 11)

EXAMPLE 5

DAF Analogs

The membrane-bound complement regulator DAF facilitates the dissociation of C3b and C4b-containing convertases but does not bind C3b or C4b, nor does it serve as cofactor for factor I-mediated proteolytic inactivation of C3b or C4b. It would be desirable, under certain situations, to increase the complement regulatory activity of DAF or of truncated, recombined or hybrid forms of DAF.

Based on amino sequence homology, DAF SCRs 2–3 corresponds to the CR1 active regions. Homology between DAF SCRs 2–3 and CR1 SCRs 1–2 is 40% while homology between DAF SCRs 2–3 and CR1 SCRs 8–9 is 39%. Since there are several unmatched amino acids in these alignments, the position numbers of DAF do not precisely match those of CR1.

One or more substitutions are introduced into the DAF SCRs 2–3. Specific substitutions designed to confer C3b and C4b cofactor activity and binding activity are selected from the following:

DAF position(s) enumerated as in Lublin and Atkinson, *Ann. Rev. Immunol.* 9:431 (1991):

| DAF position | DAF sequence | Substitution |
|---|---|---|
| 180–187 | S-D-P-L-P-E-C-R (Sequence ID No. 6) | S-T-K-P-P-I-C-Q (amino acids 54–61 of Sequence ID No. 4) |
| 175–178 | S-S-V-Q (Sequence ID No. 7) | N-A-A-H (amino acids 49–52 of Sequence ID No. 4) |
| 175–187 | S-D-P-L-P-E-C-R-S-S-V-Q (Sequence ID No. 8) | S-T-K-P-P-I-C-Q-N-A-A-H (Sequence ID No. 9) |
| 130 | P | R |
| 145 | G | D |
| 77–84 | Q-P-Y-I-T-Q-N-Y (Sequence ID No. 10) | K-L-K-T-Q-T-N-A-S-D (amino acids 12–21 of Sequence ID No. 2) |
| 90–92 | V-V-E | S-L-K (amino acids 27–29 of Sequence ID No. 2) |

Replacement of S-D-P-L-P-E-C-R (Sequence ID No. 6) at DAF position 180–187 (using the enumeration in Lublin and Atkinson, *Ann. Rev. Immunol.* (1989) 7:35–58) with S-T-K-P-P-I-C-O (amino acid 54–61 of Sequence ID No. 4) increases the affinity of DAF for C3b. Replacement of S-D-P-L-P-E-C (amino acid 1–7 of Sequence ID No. 6) with S-T-K-P-P-I-C-Q (amino acid 54–61 of Sequence ID No. 4) leaves R at the end of this segment, since R is found in the corresponding positions of CR1 SCR 1–2 (Sequence ID Nos. 1 and 3) and CR1 SCR 8–9 (Sequence ID Nos. 2 and 4). Some structurally similar amino acids can be substituted in the S-T-K-P-P-I-C-Q (amino acid 54–61 of Sequence ID No. 4) sequence.

Replacement of P at DAF position 130 with R increases the affinity of DAF for C4b. All other amino acids found important in C4b interactions in CR1 are already present in DAF SCRs 2–3.

These substitutions, by increasing the affinity of DAF for C3b and, possibly, C4b, enhance the respective 5 inhibitory effects of DAF on complement activation.

EXAMPLE 6

Analogs of Factor H

Factor H is a plasma protein consisting solely of 20 SCRs. Factor H exhibits C3b binding and C3b cofactor and dissociation capacity but no apparent ability to inactivate or bind C4b. Since factor H has already evolved as a plasma protein, it could be advantageous to use it as the starting material for soluble RCA analogs. Although the active sites of factor H are not precisely known, a proteolytic fragment composed of the first 5.5 SCRs of factor H exhibits C3b-binding and cofactor activity (Alsenz et al., *Biochem. J.* (1984) 389).

To increase the affinity of factor H for C3b binding, N-A-A-H-W-S-T-K-P-P-I-C-Q (amino acid 49–61 of Sequence ID No. 4) is introduced into several of the SCRs, none bearing a close correspondence to CR1 SCR 8–9. In one embodiment, the first six SCRs are left unmodified, thus retaining the original active site(s), and the remaining fourteen SCRs are modified by substitution of the N-A-A-H-W-S-T-K-P-P-I-C-Q (amino acid 49–61 of Sequence ID No. 4) into the position(s) homologous to CR1. Some structurally similar amino acids can substitute in-the N-A-A-H-W-S-T-K-P-P-I-C-Q (amino acid 49–61 of Sequence ID No. 4) sequence. Homologous positions are readily identified because the W that precedes this C3b binding segment is found in most SCRs: in all factor H SCRs except SCR 10 and SCR 20 while the C within the C3b binding segment is found in all the known SCRs. While not all substitutions will necessarily confer added binding activity, since these factor H SCRs are less homologous to the CR1 SCR 1–2 and CR1 SCR 8–9 regions. However, at least some modified H SCRs gain C3b-binding capacity, resulting in a factor H analog with much higher affinity for C3b. As discussed above, higher affinity would lead to the greater use of the active sites already present in the first six H SCRs.

Modifications and variations of the present invention will be obvious to those skilled in the art from the foregoing detailed description. These modifications and variations are intended to come within the scope of the following claims.

We claim:

1. A modified form of a regulator of complement activation protein (RCA protein) wherein the RCA protein is selected from the group consisting of complement receptor 1, decay accelerating factor, membrane cofactor protein, C4 binding protein, factor H, and these RCA proteins wherein the carboxy terminus of the RCA protein is removed to allow the protein to be secreted, wherein the modified form is selected from the group consisting of:

a) a hybrid RCA protein comprising short consensus repeats (SCRs) derived from two, different of the RCA proteins, b) a recombined RCA protein wherein the SCRs of the RCA protein are rearranged, and c) a truncated RCA protein consisting of three SCRs, wherein the modified form of the RCA protein binds C3b, C4b or C3b and C4b.

2. The modified form of the RCA protein of claim 1 wherein the RCA protein is complement receptor 1.

3. The modified form of an RCA protein of claim 1 wherein the RCA protein is decay accelerating factor.

4. The modified form of the RCA protein of claim 1 wherein the RCA protein is factor H.

5. A modified form of an RCA protein wherein the RCA protein is selected from the group consisting of complement receptor 1, complement receptor 2, decay accelerating factor, membrane cofactor protein, C4 binding protein, factor H, and these RCA proteins wherein the carboxy terminus of the RCA protein is removed to allow the protein to be secreted, wherein the modified form contains amino acid substitutions in the SCRs which correspond to amino acid substitutions in the SCRs of complement receptor 1 (SEQ ID No: 13) selected from the group consisting of:

CR1–4 with its first 122 amino acids (SCR1–2) (Sequence ID Nos 1 and 3) replaced with CR1 amino acids 497–618 (SCR 8–9) (Sequence ID Nos. 2 and 4) and CR1–4(8,9) with deletion of 194–253; and substitution of amino acids 271–543 with T-R-T-T-F-H-L-G-R-K-C-S-T-A-V-S-P-A-T-T-S-E-G-L-R-L-C-A-A-H-P-R-E-T-G-A-L-Q-P-P-H-V-K (Sequence ID No. 11), or these amino acid sequences where any I is replaced with either L or V, any L is replaced with either I or V, any V is replaced with I, L, or F, any F is replaced with V, any K is replaced with R, any R is replaced with K, any Q is replaced with N, any N is replaced with Q, any D is replaced with E, any E is replaced with D, any G is replaced with A, or any A is replaced with G.

6. A modified form of decay accelerating factor wherein one or more substitutions are introduced into the region of the protein corresponding to decay accelerating factor SCRs 2–3 as shown in Sequence ID No. 17 selected from the group consisting of 180–187: S-T-K-P-P-I-C-Q (amino acids 54–61 of Sequence ID No. 4); 175–178: N-A-A-H (amino acids 49–52 of Sequence ID No. 4); 175–187: S-T-K-P-P-I-C-Q-N-A-A-H (Sequence ID No. 9); 130: R (amino acid 4 of Sequence ID No. 3); 145: D (amino acid 19 of Sequence ID No. 4); 77–84: K-L-K-T-Q-T-N-A-S-D (amino acids 12–21 of Sequence ID No. 2); 90–92: S-L-K (amino acids 27–29 of Sequence ID No. 2), and these amino acid sequences where I is replaced with either L or V, L is replaced with either I or V, V is replaced with I, L or F, F is replaced with V, K is replaced with R, R is replaced with K, Q is replaced with N, N is replaced with Q, D is replaced with E, E is replaced with D, G is replaced with A, or A is replaced with G.

7. The modified form of the RCA protein of claim 1 wherein the modified form of the RCA protein is factor H comprising sequences conferring on the modified form of the RCA protein an activity selected from the group consisting of C3b binding activity, C3b cofactor activity, C4b binding activity, and C4b cofactor activity, wherein the sequences are derived from a protein selected from the group consisting of complement receptor 1, membrane cofactor protein, C4 binding protein, and factor H.

8. The modified form of the RCA protein of claim 1 wherein the hybrid RCA protein comprises SCRs derived from an RCA protein selected from the group consisting of complement receptor 1, decay accelerating factor, membrane cofactor protein, C4 binding protein, and factor H.

9. The modified form of the RCA protein of claim 1 wherein the modified form of the RCA protein includes SCRs 2, 3 and 4 of DAF and has C3b cofactor activity, C4b cofactor activity and decay accelerating activity.

10. A modified form of the RCA protein of claim 1 wherein the truncated RCA protein consists of three SCRs and has two complement regulatory activities.

11. The modified form of the RCA protein of claim 1, 3 or 8, further comprising a pharmaceutically acceptable carrier.

12. A method for making a modified form of an RCA protein wherein the RCA protein is selected from the group consisting of complement receptor 1, decay accelerating factor, membrane cofactor protein, C4 binding protein, factor H, and these RCA proteins wherein the carboxy terminus of the RCA protein is removed to allow the protein to be secreted, wherein the modified form is selected from the group consisting of:
 a) a hybrid RCA protein comprising SCRs derived from two, different of the RCA proteins,
 b) a recombined RCA protein wherein the three SCRs of the RCA proteins are rearranged, and
 c) a truncated RCA protein consisting of three SCRs,
wherein the modified form of the RCA protein binds C3b, C4b, or C3b and C4b,
 the method comprising expressing a DNA sequence encoding the modified form of the RCA protein in a host cell.

13. The method of claim 12 wherein the RCA protein is complement receptor 1.

14. The method of claim 12 wherein the RCA protein is decay accelerating factor.

15. The method of claim 12 wherein the RCA protein is factor H.

16. A method for making a modified form of an RCA protein wherein the RCA protein is selected from the group consisting of complement receptor 1, complement receptor 2, decay accelerating factor, membrane cofactor protein, C4 binding protein, factor H, and these proteins wherein the carboxy terminus of the RCA protein is removed to allow the protein to be secreted, wherein the modified form of an RCA protein contains amino acid substitutions in the SCRs which correspond to amino acid substitutions in the SCRs of complement receptor 1 (SEQ ID No: 13) select from the group consisting of:
 CR1–4 with its first 122 amino acids (SCR1–2) (Sequence ID Nos. 1 and 3) replaced with CR1 amino acids 497–618 (SCR 8–9) (Sequence ID Nos. 2 and 4) and CR1–4(8.9) with deletion of 194–253; substitution of amino acids 271–543 with: T-R-T-T-F-H-L-G-R-K-C-S-T-A-V-S-P-A-T-T-S-E-G-L-R-L-C-A-A-H-P-R-E-T-G-A-L-Q-P-P-H-V-K (Sequence ID No. 11), and these amino acid sequences where any I is replaced with either L or V, any L is replaced with either I or V, any V is replaced with I, L, or F, any F is replaced with V, any K is replaced with R, any R is replaced with K, any Q is replaced with N, any N is replaced with Q, any D is replaced with E, any E is replaced with D, any G is replaced with A, or any A is replaced with G, the method comprising expressing a DNA encoding the modified form of the RCA protein in a host cell.

17. A method for making a modified form of an RCA protein wherein the RCA protein is selected from the group consisting of complement receptor 1, complement receptor 2, decay accelerating factor, membrane cofactor protein, C4 binding protein, factor H, and these proteins wherein the carboxy terminus of the RCA protein is removed to allow the protein to be secreted, wherein the modified form of an RCA protein contains amino acid substitutions in the SCRs which corresond to amino acid substitutions in the SCRs of complement receptor 1 (SEQ ID No: 13) selected from the group consisting of:
 79: D (amino acid 19 of Sequence ID No. 4); 37, 79: Y, D (amino acid 37 of Sequence ID No. 2 and amino acid 19 of Sequence ID No. 4); 92: T (amino acid 32 of Sequence ID No. 4); 92–94: K . . . Y (amino acids 32–34 of Sequence ID NO. 3); 99, 103, 106: S . . . T . . . I (amino acids 39, 43 and 46 of Sequence ID No. 3); 109–112: D-T-V-I (amino acids 49–52 of Sequence ID No. 3); 110: T (amino acid 50 of Sequence ID No.3); 111: V (amino acids 51 of Sequence ID No. 3); 112: I (amino acid 52 of Sequence ID No. 3); 1, 3; Q . . . N (amino acids 1, 3 of Sequence ID No. 1); 6–9: E-W-L-P (amino acids 6–9 of Sequence ID No. 1); 12–16, 18–21: K-L-K-T-Q . . . , N-A-S-D (amino acids 12–21 of Sequence ID No. 2); 27, 29: S . . . K (amino acids 27, 29 of Sequence ID No. 2); 37: S (amino acid 37 of Sequence ID No. 1): 44, 47, 49: I . . . K . . . S (amino acids 44, 47, 49 of Sequence ID No. 1); 52–54, 57, 59: TG-A . . . R . . . R (amino acids 52–54, 57, 59 of Sequence ID No. 1); 78–79, 82: K-G . . . F (amino acids 18–19, 22 of Sequence ID No. 3); 85, 87: Q . . . K (amino acids 25, 27 of Sequence ID No. 3); 12–16, 18–21: R-P-T-N-L . . . D-E-F-E (amino acids 12–21 of Sequence ID No. 1); 27, 29: Y . . . N (amino acids 27, 29 of Sequence ID No. 1); 35, 64–65, 94: G . . . R-N . . . Y (amino acid 35 of Sequence ID No. 1, amino acids 4–5, 34 of Sequence ID No. 3), and these amino acid sequences where any I is replaced with either L or V, any L is replaced with either I or V, any V is replaced with I, L, or F, any F is replaced with V, any K is replaced with R, any R is replaced with K, any Q is replaced with N, any N is replaced with Q, any D is replaced with E, any E is replaced with D, any G is replaced with A, or any A is replaced with G, the method comprising expressing a DNA encoding the modified form of the RCA protein in a host cell.

18. A method for making a modified form of decay accelerating factor wherein one or more substitutions are introduced into the region of the protein corresponding to decay accelerating factor SCRs 2–3 as shown in Sequence ID No. 17 selected front the group consisting of
 180–187: S-T-K-P-P-I-C-Q (amino acids 54–61 of Sequence ID No. 4); 175–178: N-A-A-H (amino acids 49–52 of Sequence ID No. 4); 175–187: S-T-K-P-P-I-C-Q-N-A-A-H (Sequence ID No. 9); 130: R (amino acid 4 of Sequence ID No. 3); 145: D (amino acid 19 of Sequence ID No. 4); 77–84: K-L-K-T-Q-T-N-A-S-D (amino acids 12–21 of Sequence ID No. 2); 90–92: S-L-K (amino acids 27–29 of Sequence ID No. 2), and these amino acid sequences where any I is replaced with either L or V, any L is replaced with either I or V, any V is replaced with I, L, or F, any F is replaced with V, any K is replaced with R, any R is replaced with K, any Q is replaced with N, any N is replaced with Q, any D is replaced with E, any E is replaced with D, any G is replaced with A, or any A is replaced with G, the method comprising expressing a DNA encoding the modified form of decay accelerating factor in a host cell.

19. The method of claim 12 wherein the RCA protein is factor H comprising sequences conferring on the protein an activity selected from the group consisting of C3b binding activity, C3b cofactor activity, C4b binding activity, and C4b cofactor activity, wherein the sequences are derived from an RCA protein selected from the group consisting of complement receptor 1, membrane cofactor protein, C4 binding protein, and factor H.

20. The method of claim 12 wherein the DNA sequence encodes a hybrid RCA protein comprising SCRs derived from an RCA protein selected from the group consisting of complement receptor 1, decay accelerating factor, membrane cofactor protein, C4 binding protein and factor H, including in reading frame a DNA encoding at least one SCR derived from a different RCA protein selected from the group consisting of complement receptor 1, decay accelerating factor, membrane cofactor protein, C4 binding protein, and factor H.

21. The method of claim 12 wherein the modified form of the RCA protein includes SCRs 2, 3 and 4 of DAF and has C3b cofactor activity, C4b cofactor activity and decay accelerating activity.

22. The method of claim 12 wherein the modified form of the RCA protein is a truncated RCA protein consisting of three SCRs and having two complement regulatory activities.

23. The method of claim 12 further comprising isolating the modified form of the RCA protein and mixing with the isolated modified form of an RCA protein a pharmaceutically acceptable carrier.

24. A DNA sequence which encodes a modified form of the RCA protein of claim 1, 3, or 8.

25. The DNA sequence of claim 24 inserted into an expression vector operably linked to control sequences compatible with a host cell, which expression vector is capable, when transformed into the host cell, of expressing a DNA encoding the modified form of the RCA protein.

26. A method for enhancing the C4b or C3b cofactor activity of an RCA protein, wherein the protein has either C3b or C4b cofactor activity, comprising adding sequences to the protein conferring binding of the other ligand, either C4b or C3b, wherein the sequences are present in a protein selected from the group of naturally occurring complement receptor 1, decay accelerating factor, membrane cofactor protein, C4 binding protein, and factor H.

* * * * *

UNITED STATES PATENT AND TRADEMARK OFFICE
CERTIFICATE OF CORRECTION

PATENT NO. : 6,897,290 B1
DATED : May 24, 2005
INVENTOR(S) : John P. Atkinson, Dennis Hourcade and Malgorzata Krych It is certified that error appears in the above-identified patent and that said Letters Patent is hereby corrected as shown below:

Column 75,
Line 58, delete "(8.9)" and insert -- (8,9) --.

Column 76,
Line 27, delete ", N-A-S-D" and insert -- N-A-S-D --.
Line 54, delete "front" and insert -- from --.

Signed and Sealed this

Sixteenth Day of August, 2005

JON W. DUDAS
*Director of the United States Patent and Trademark Office*